(12) United States Patent
Garcia-Garcia et al.

(10) Patent No.: US 10,519,430 B2
(45) Date of Patent: Dec. 31, 2019

(54) BIFIDOBACTERIUM LONGUM

(71) Applicant: Alimentary Health Ltd., Cork (IE)

(72) Inventors: Jose Carlos Garcia-Garcia, Cincinnati, OH (US); Michael John Janusz, West Chester, OH (US); Barry Kiely, Cork (IE); Eileen Frances Murphy, Cork (IE); Liam O'Mahony, Cork (IE)

(73) Assignee: Alimentary Health Ltd., Cork (IE)

( * ) Notice: Subject to any disclaimer, the term of this patent is extended or adjusted under 35 U.S.C. 154(b) by 0 days.

(21) Appl. No.: 16/266,372

(22) Filed: Feb. 4, 2019

(65) Prior Publication Data

US 2019/0153408 A1    May 23, 2019

Related U.S. Application Data

(63) Continuation of application No. 15/247,997, filed on Aug. 26, 2016, now Pat. No. 10,233,433.

(30) Foreign Application Priority Data

Aug. 27, 2015 (EP) ..................................... 15182695

(51) Int. Cl.
| | | |
|---|---|---|
| *A61K 35/745* | (2015.01) | |
| *A61K 35/74* | (2015.01) | |
| *A23L 33/135* | (2016.01) | |
| *A23C 9/12* | (2006.01) | |
| *C12N 9/12* | (2006.01) | |

(52) U.S. Cl.
CPC .............. *C12N 9/12* (2013.01); *A23C 9/1203* (2013.01); *A23L 33/135* (2016.08); *A61K 35/74* (2013.01); *A61K 35/745* (2013.01); *C12Y 207/10002* (2013.01); *A23V 2002/00* (2013.01); *A23Y 2300/55* (2013.01)

(58) Field of Classification Search
CPC . A23C 9/1203; A23L 33/135; A23V 2002/00; A23Y 2300/55; A61K 35/74; A61K 35/745; C12N 9/12; C12Y 207/10002
See application file for complete search history.

(56) References Cited

U.S. PATENT DOCUMENTS

| | | |
|---|---|---|
| 7,195,906 B2 | 3/2007 | Collins et al. |
| 7,923,000 B2 | 4/2011 | Chen et al. |
| 8,168,170 B2 | 5/2012 | Myatt |
| 8,216,563 B2 | 7/2012 | Chen et al. |
| 8,357,794 B2 | 1/2013 | Grant et al. |
| 8,926,952 B2 | 1/2015 | Trejo et al. |
| 2008/0145341 A1 | 6/2008 | Myatt et al. |
| 2009/0196921 A1 | 8/2009 | Ebel et al. |
| 2010/0183559 A1 | 7/2010 | Van Sinderen et al. |
| 2016/0228476 A1 | 8/2016 | Cutcliffe et al. |

FOREIGN PATENT DOCUMENTS

| | | |
|---|---|---|
| WO | WO2003010299 A1 | 2/2003 |
| WO | WO2008117267 A2 | 10/2008 |

OTHER PUBLICATIONS

International Search Report and Written Opinion for PCT/US2016/048853 dated Nov. 18, 2016.
Routray, Winny et al. "Scientific and Technical Aspects of Yogurt Aroma and Taste: A Review", Comprehensive Reviews in Food Science and Food Safety 10: 208-220, 2011.
Wu, Ming-Hsiu et al., "Exopolysaccharide activities from probiotic bifidobacteriurn: Immunomodulatory effects (on J774A.1 macrophages) and antimicrobial properties" International Journal of Food Microbiology, vol. 144, No. 1, Nov. 15, 2010, pp. 104-110.
All Office Actions from U.S. Appl. No. 15/247,997, filed Aug. 26, 2016.

*Primary Examiner* — Sarvamangala Devi
*Assistant Examiner* — S. Devi
(74) *Attorney, Agent, or Firm* — Bookoff McAndrews, PLLC

(57) ABSTRACT

A formulation comprising an ingestible carrier and an isolated strain of *Bifidobacterium longum*.

5 Claims, 6 Drawing Sheets

Specification includes a Sequence Listing.

BIFIDOBACTERIUM LONGUM

FIELD OF THE INVENTION

The invention relates to the genome of a probiotic bifidobacteria strain, proteins encoded by the genome and exopolysaccharides produced by the proteins. Bifidobacteria are one of several predominant culturable bacteria present in human colonic microflora.

BACKGROUND OF THE INVENTION

Bifidobacteria are considered to be probiotics as they are living organisms which exert healthy effects beyond basic nutrition when ingested in sufficient numbers. A high level of ingested bifidobacteria must reach their site of action in order to exert a probiotic effect. A minimum level of approximately $10^6$-$10^7$ viable bifidobacteria per gram intestinal contents has been suggested (Bouhnik, Y., Lait 1993). There are reports in the literature which show that in vivo studies completed in adults and in infants indicate that some strains of bifidobacteria are capable of surviving passage through the gastrointestinal tract. Significant differences have been observed between the abilities of different bifidobacteria strains to tolerate acid and bile salts, indicating that survival is an important criterion for the selection of potential probiotic strains.

Ingestion of bifidobacteria can improve gastrointestinal transit and may prevent or assist in the treatment of illnesses which may be caused by deficient or compromised microflora such as gastrointestinal tract (GIT) infections, constipation, irritable bowel syndrome (IBS), inflammatory bowel disease (IBD)—Crohn's disease and ulcerative colitis, food allergies, antibiotic-induced diarrhoea, cardiovascular disease, and certain cancers (e.g. colorectal cancer).

Because of their perceived health-promoting activities, bifidobacteria have in recent years enjoyed an increased amount of scientific scrutiny, which included the full genomic sequencing of a number of strains (reviewed by Liu et al., 2005). These genomic sequences will provide the genetic platforms that allow the study of the molecular mechanisms by which these micro organisms interact with their human host and elicit their probiotic function.

SUMMARY OF THE INVENTION

According to the invention there is provided an isolated and purified *Bifidobacterium longum* strain, wherein the strain:
  a) expresses an exopolysaccharide containing 6-deoxy tabs; and
  b) comprises nucleic acid sequence SEQ ID NO. 86 or nucleic acid sequences with at least 95% sequence homology thereto that codes for protein-tyrosine-phosphatase.

Excluded are the following strains:
35624 (NCIMB 41003)
BL1207 (PTA-9608);
AH121A (NCIMB 41675);
AH1714 (NCIMB 41676); and
AH1206 (NCIMB 41382)

In one embodiment the *Bifidobacterium longum* strain comprises:
  nucleic acid SEQ. ID NO. 86 or a nucleic acid sequence with at least 95% sequence homology thereto;
  nucleic acid SEQ. ID NO. 62 or a nucleic acid sequence with at least 95% sequence homology thereto that codes for priming glcosyltransferase; and
  at least one selected from the group comprising nucleic acid, SEQ ID No. 65, SEQ ID No. 66, SEQ ID No. 69, SEQ ID No. 72, SEQ ID No. 74 or nucleic acid sequences with at least 95% sequence homology thereto that codes for glcosyltransferase.

The strain may comprise at least two selected from the group comprising nucleic acid SEQ ID No. 65, SEQ ID No. 66, SEQ ID No. 69, SEQ ID No. 72, SEQ ID No. 74 or nucleic acid sequences with at least 95% sequence homology thereto.

The strain may comprise at least three selected from the group comprising nucleic acid SEQ ID No. 65, SEQ ID No. 66, SEQ ID No. 69, SEQ ID No. 72, SEQ ID No. 74 or nucleic acid sequences with at least 95% sequence homology thereto.

The strain may comprise at least four selected from the group comprising nucleic acid SEQ ID No. 65, SEQ ID No. 66, SEQ ID No. 69, SEQ ID No. 72, SEQ ID No. 74 or nucleic acid sequences with at least 95% sequence homology thereto.

The strain may comprise nucleic acid SEQ ID No. 65, SEQ ID No. 66, SEQ ID No. 69, SEQ ID No. 72, and SEQ ID No. 74 or nucleic acid sequences with at least 95% sequence homology thereto.

The strain may comprise at least one selected from the group comprising nucleic acid SEQ ID No. 71, SEQ ID No. 76 or nucleic acid sequences with at least 95% sequence homology thereto that codes for acyltransferase.

The strain may comprise nucleic acid SEQ ID No. 71 and SEQ ID No. 76 or nucleic acid sequences with at least 95% sequence homology thereto that codes for acyltransferase.

The invention also provides *Bifidobacterium longum* strain AH0097 having NCIMB accession number 41712 or mutants or variants thereof.

The invention also provides *Bifidobacterium longum* strain AH1172 having NCIMB accession number 41714 or mutants or variants thereof.

The mutant may be a genetically modified mutant.

The variant may be a naturally occurring variant of *Bifidobacterium*.

The *Bifidobacterium* strain may be probiotic.

In some cases the strain is in the form of a biologically pure culture.

Also provided is an isolated strain of *Bifidobacterium longum* AH0097 (NCIMB 41712).

Also provided is an isolated strain of *Bifidobacterium longum* AH1172 (NCIMB 41714).

The strain may be in the form of viable cells or in the form of non-viable cells.

In one case the *Bifidobacterium* strain is isolated from human faeces.

The isolated and purified *Bifidobacterium longum* strain may be in the form of a bacterial broth.

The isolated and purified *Bifidobacterium longum* strain may be in the form of a freeze-dried powder.

The invention also provides a formulation comprising an isolated strain of *Bifidobacterium longum* of the invention.

The formulation may comprise an ingestable carrier.

The ingestable carrier may be a pharmaceutically acceptable carrier.

The ingestable carrier may be a food product

The food product may be selected from the group comprising acidified milk, yoghurt, frozen yoghurt, milk powder, milk concentrate, cheese spread, dressing and beverage.

The formulation may be in the form of a fermented food product.

The formulation may be in the form of a fermented milk product.

In one embodiment the carrier does not occur in nature.

The formulation may be the form of a capsule, a tablet, a pellet, or a powder.

In some cases the strain is present in the formulation at more than $10^6$ CFU per gram of ingestable carrier.

The invention also provides the use of a *Bifidobacterium longum* strain as a probiotic strain.

According to another aspect, the invention provides a method for identifying an exopolysaccharide expressing *Bifidobacterium longum* strain comprising the steps of:

a) obtaining a sample comprising bacteria;
b) extracting nucleic acid from the sample;
c) amplifying the extracted nucleic acid in the presence of at least two primers derived from a nucleic acid sequence selected from the group comprising: SEQ ID No 62 to SEQ ID No 86 or a nucleic acid sequence with at least 95% sequence homology thereto
d) identifying a bacterial strain that expresses an exopolysaccharide.

In one case the primer comprises at least 10 consecutive bases from a nucleic acid sequence selected from the group comprising: SEQ ID No. 62 to SEQ ID No. 86.

The primer may comprise a nucleic acid sequence selected from the group comprising: SEQ ID No. 12 to SEQ ID No. 61 or a nucleic acid sequence with at least 95% sequence homology thereto.

The step of identifying a bacterial strain that expresses an exopolysaccharide may comprise growing the bacterial strain on a Congo red agar plate.

In one case the sample is a mammalian sample.

The sample may be a human derived sample.

In one case the sample is a fecal sample.

Also provided is a *Bifidobacterium longum* strain identified by a method of the invention.

The invention also provides a method for the prophylaxis and/or treatment of undesirable inflammatory activity comprising administering a strain of the invention or a formulation of the invention.

The undesirable inflammatory activity may be undesirable gastrointestinal inflammatory activity such as inflammatory bowel disease eg. Crohns disease or ulcerative colitis, irritable bowel syndrome; pouchitis; or post infection colitis.

Also provided is a method for the prophylaxis and/or treatment of gastrointestinal cancer(s) comprising administering a strain of the invention or a formulation of the invention.

Also provided is a method for the prophylaxis and/or treatment of systemic disease such as rheumatoid arthritis comprising administering a strain of the invention or a formulation of the invention.

Also provided is a method for the prophylaxis and/or treatment of autoimmune disorders due to undesirable inflammatory activity comprising administering a strain of the invention or a formulation of the invention.

Also provided is a method for the prophylaxis of cancer comprising administering a strain of the invention or a formulation of the invention.

The invention also provides a method for the prophylaxis and/or treatment of diarrhoeal disease due to undesirable inflammatory activity, such as *Clostridium difficile* associated diarrhoea, Rotavirus associated diarrhoea or post infective diarrhoea or diarrhoeal disease due to an infectious agent, such as *E. coli* comprising administering a strain of the invention or a formulation of the invention.

Also provided is a method for the prevention and/or treatment of inflammatory disorders, immunodeficiency, inflammatory bowel disease, irritable bowel syndrome, cancer (particularly of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and/or acne vulgaris comprising administering a strain of the invention or a formulation of the invention.

A *Bifidobacterium longum* strain in accordance with an embodiment of the invention may express or produce EPS at a yield of between about 1 mg/L to about 1000 mg/L of bacterial culture depending on growth conditions.

BRIEF DESCRIPTION OF THE DRAWINGS

The invention will be more clearly understood from the following description thereof given by way of example only with reference to the accompanying drawings in which.

DETAILED DESCRIPTION OF THE INVENTION

Figure 1:
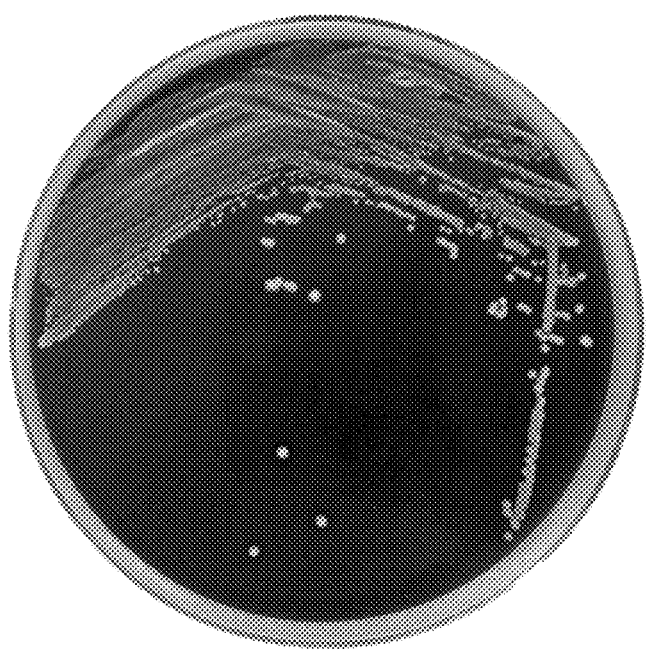
FIG. 1 is a photograph of *B. longum* NCIMB 41712 (AH0097) grown on a Congo Red Agar plate.

A deposit of *Bifidobacterium longum* 35624 was made at the National Collections of Industrial and Marine Bacteria Limited (NCIMB) Ferguson Building, Craibstone Estate, Bucksburn, Aberdeen, AB21 9YA, Scotland, UK on Jan. 13, 1999 and accorded the accession number NCIMB 41003.

A deposit of *Bifidobacterium longum* strain AH0097 was made at the National Collections of Industrial and Marine Bacteria Limited (NCIMB) Ferguson Building, Craibstone Estate, Bucksburn, Aberdeen, AB21 9YA, Scotland, UK on May 6, 2010 and accorded the accession number NCIMB 41712.

A deposit of *Bifidobacterium longum* strain AH1172 was made at the National Collections of Industrial and Marine Bacteria Limited (NCIMB) Ferguson Building, Craibstone Estate, Bucksburn, Aberdeen, AB21 9YA, Scotland, UK on May 6, 2010 and accorded the accession number NCIMB 41714.

Given the size of the isolated polynucleotide it would not be uncommon for a point mutation or some other form of mutation to be present in the sequence. As such we encompass variants of SEQ ID No. 1 in the disclosure. As used herein, the term "variants", means strains of Bifidobacteria that have a sequence identity of at least 99.5% or more with SEQ ID No. 1.

As used herein, the term "sequence homology" encompasses sequence homology at a nucleic acid and/or an amino acid (protein) level. Sequence homology is indicated as the overall percentage of identity across the nucleic acid and/or amino acid sequence. The sequence homology may be determined using standard techniques known to those skilled in the art. For example sequence homology may be determined using the on-line homology algorithm "BLAST" program. A sequence may have at least at least 95% or at least 96% or at least 97% or at least 98% or at least 99% sequence homology with the nucleic acid sequences described herein or the amino acid (protein) encoded thereby.

The present invention is based on the whole genome sequence of *Bifidobacterium longum* NCIMB 41003 (35624™). The genome sequence is listed in SEQ ID No. 1 of the attached sequence listing and comprises 2,264,056 base pairs. Analysis of the genome sequence identified 1,734 genes having the open reading frames as set out in Table 1 below.

TABLE 1

Open reading frames of the genome of 35624.

| Gene ID | Start | End | Strand | Predicted Function |
|---|---|---|---|---|
| B624_0001 | 1 | 1500 | + | chromosomal replication initiator protein DnaA |
| B624_0002 | 2239 | 3360 | + | DNA polymerase III, beta subunit |
| B624_0003 | 3442 | 4626 | + | recF protein |
| B624_0004 | 4626 | 5093 | + | hypothetical protein |
| B624_0005 | 5277 | 7364 | + | DNA gyrase, B subunit |
| B624_0006 | 7435 | 10083 | + | DNA gyrase, A subunit |
| B624_0007 | 10156 | 10719 | + | hypothetical protein |
| B624_0008 | 11406 | 12116 | + | hypothetical protein |
| B624_0009 | 12116 | 13699 | + | Pectinesterase |
| B624_0010 | 14103 | 15446 | − | NADP-specific glutamate dehydrogenase |
| B624_0011 | 15768 | 16199 | − | AsnC-type transcriptional regulator |
| B624_0012 | 16405 | 17736 | + | aspartate aminotransferase |
| B624_0013 | 17757 | 18746 | − | hypothetical protein |
| B624_0014 | 19007 | 19600 | + | hypothetical protein |
| B624_0015 | 19617 | 20462 | + | hypothetical protein |
| B624_0016 | 20579 | 20821 | + | hypothetical protein |
| B624_0017 | 21403 | 21735 | − | transposase |
| B624_0018 | 22130 | 23497 | − | Transcriptional regulatorscontaining a DNA-binding HTH domain and anaminotransferase domain (MocR family) |
| B624_0019 | 24132 | 25454 | + | gabt-aminotransferase, class III superfamily |
| B624_0020 | 25675 | 26397 | + | Metal-dependent hydrolase |
| B624_0021 | 26487 | 26849 | + | Gluconate kinase |
| B624_0022 | 27115 | 28424 | − | Hypothetical protein |
| B624_0023 | 28662 | 29138 | − | Dps family protein |
| B624_0024 | 29263 | 30578 | − | CBS domain protein |
| B624_0025 | 30841 | 31521 | − | Prokaryotic-type carbonic anhydrases |
| B624_0026 | 31727 | 32287 | + | alkyl hydrogen peroxide reductase |
| B624_0027 | 32458 | 34371 | + | thioredoxin reductase |
| B624_0028 | 34494 | 35777 | − | hypothetical protein |
| B624_0029 | 36333 | 37328 | + | LacI-type transcriptional regulator |
| B624_0030 | 37558 | 40308 | − | phosphoenolpyruvate carboxylase |
| B624_0031 | 40594 | 42471 | + | protein of unknown function |
| B624_0032 | 42707 | 44342 | + | possible sodium/proline symporter |
| B624_0033 | 44680 | 45663 | − | hypothetical protein |
| B624_0034 | 45917 | 47533 | + | amidohydrolase 3 |
| B624_0035 | 47717 | 48805 | − | tryptophanyl-tRNA synthetase |
| B624_0036 | 48939 | 49325 | + | hypothetical protein |
| B624_0037 | 49437 | 49841 | − | hypothetical protein |
| B624_0038 | 49986 | 52505 | + | glycogen phosphorylase |
| B624_0039 | 52725 | 52940 | − | hypothetical protein |
| B624_0040 | 53045 | 53880 | + | Rhomboid family protein |
| B624_0041 | 54557 | 55029 | − | hypothetical protein |
| B624_0042 | 55119 | 55907 | + | hypothetical protein |
| B624_0043 | 55907 | 57142 | + | Sortase |
| B624_0044 | 57196 | 57837 | + | para-aminobenzoate synthase glutamineamidotransferase component II |
| B624_0045 | 58067 | 60136 | − | serine/threonine protein kinase |
| B624_0046 | 60136 | 61083 | − | serine/threonine protein kinase |
| B624_0047 | 61083 | 62546 | − | pbpA |
| B624_0048 | 62546 | 64204 | − | cell cycle protein |
| B624_0049 | 64204 | 65895 | − | possible phosphoprotein phosphatase |
| B624_0050 | 65903 | 66430 | − | FHA-domain-containing proteins |
| B624_0051 | 66463 | 67161 | − | FHA domain protein |
| B624_0052 | 67349 | 69790 | − | dipeptidyl peptidase IV |
| B624_0053 | 69900 | 70997 | + | lysophospholipase L2 |
| B624_0054 | 71089 | 72221 | + | von Willebrand factor type A domain protein |

TABLE 1-continued

Open reading frames of the genome of 35624.

| Gene ID | Start | End | Strand | Predicted Function |
|---|---|---|---|---|
| B624_0056 | 72947 | 73348 | + | hypothetical protein |
| B624_0058 | 75108 | 75608 | + | heat shock protein, Hsp20 family |
| B624_0059 | 75938 | 76891 | + | Methyl viologen exporter |
| B624_0060 | 77065 | 77520 | − | hypothetical protein |
| B624_0061 | 77753 | 79132 | + | esterase |
| B624_0062 | 79132 | 81702 | + | Uncharacterized BCR |
| B624_0063 | 82241 | 83212 | + | peptide methionine sulfoxide reductase |
| B624_0064 | 83506 | 86709 | − | helicase-related protein |
| B624_0065 | 86785 | 87195 | − | mutator MutT protein |
| B624_0066 | 88258 | 88587 | + | hypothetical protein |
| B624_0067 | 88678 | 89139 | + | acetyltransferase, GNAT family family |
| B624_0068 | 89226 | 90080 | − | Hemolysin III-like membrane protein |
| B624_0069 | 90480 | 90842 | + | hypothetical protein |
| B624_0070 | 91329 | 92639 | − | queuine tRNA-ribosyltransferase |
| B624_0071 | 93056 | 95065 | + | peptidase S1 and S6, chymotrypsin/Hap |
| B624_0072 | 95477 | 97636 | + | cation-transporting ATPase, E1-E2 family |
| B624_0073 | 97816 | 98862 | + | transcriptional regulator, LacI family |
| B624_0074 | 98874 | 99131 | − | Sec-independent protein translocase protein TatB-like protein |
| B624_0075 | 99173 | 100215 | − | Twin arginine targeting (Tat) protein translocase TatC |
| B624_0076 | 100215 | 100502 | − | Twin-arginine translocationprotein, TatA/E family |
| B624_0077 | 101182 | 103584 | + | Hypothetical protein |
| B624_0078 | 103674 | 106151 | + | Bacterial surface proteins containing Ig-like domains |
| B624_0079 | 106547 | 107707 | − | AAA+ superfamily ATPase |
| B624_0080 | 107911 | 109359 | + | ferredoxin/ferredoxin--NADP reductase |
| B624_0081 | 109533 | 110450 | + | heat shock protein HtpX |
| B624_0082 | 110667 | 111731 | − | fructose-bisphosphate aldolase, class II |
| B624_0083 | 111947 | 113230 | + | adenylosuccinate synthetase |
| B624_0084 | 113257 | 114837 | + | CPA2 family monovalent cation:proton (H+) antiporter-2 |
| B624_0085 | 115027 | 116094 | + | CrcB-like protein family |
| B624_0086 | 116097 | 116489 | + | protein with similarity to CrcB |
| B624_0087 | 116767 | 117849 | + | sugar-binding transcriptional regulator, LacIfamily |
| B624_0088 | 118052 | 119842 | + | Kup system potassium uptake protein [imported] |
| B624_0089 | 120262 | 121806 | + | alpha-L-arabinofuranosidase |
| B624_0090 | 121993 | 123012 | + | transcription regulator, LacI family [imported] |
| B624_0091 | 123104 | 124012 | − | Alpha-glucosidase |
| B624_0093 | 124604 | 125803 | + | probable integrase/recombinase |
| B624_0094 | 125803 | 126765 | + | probable integrase/recombinase |
| B624_0095 | 126765 | 127817 | + | integrase/recombinase XerC, probable [imported] |
| B624_0096 | 127910 | 128956 | − | IS3 family transposase |
| B624_0097 | 129291 | 130814 | + | ScrP-sucrose phosphorylase |
| B624_0098 | 131035 | 132669 | + | ScrT |
| B624_0099 | 132736 | 133776 | + | LacI family transcriptional regulator |
| B624_0100 | 134407 | 135771 | + | major facilitator family transporter |
| B624_0101 | 135971 | 137020 | + | ketol-acid reductoisomerase |
| B624_0102 | 137452 | 138501 | + | ketol-acid reductoisomerase |
| B624_0103 | 138689 | 140500 | − | alpha-amylase family protein |
| B624_0104 | 140663 | 141694 | − | transcription regulator, LacI family [imported] |
| B624_0105 | 142008 | 144242 | − | 4-alpha-glucanotransferase |
| B624_0107 | 144829 | 145482 | + | alpha-amylase |
| B624_0108 | 145500 | 146507 | − | transcription regulator, LacI family [imported] |
| B624_0109 | 146777 | 147490 | + | sugar ABC transporter, permease protein |
| B624_0110 | 147605 | 150139 | + | glycosyl hydrolase, family 31 |
| B624_0111 | 151125 | 153002 | + | dnaK protein |
| B624_0112 | 153005 | 153658 | + | co-chaperone GrpE |
| B624_0113 | 153753 | 154769 | + | DnaJ protein |
| B624_0114 | 154787 | 155371 | + | hspR |
| B624_0115 | 155647 | 156996 | + | xanthine permease |
| B624_0116 | 157036 | 158154 | + | possible acyl protein synthase/acyl-CoAreductase-like protein |
| B624_0117 | 158144 | 159640 | + | possible acyl-CoA reductase |
| B624_0118 | 159697 | 160497 | + | 3-oxoacyl-acyl carrier protein reductase |
| B624_0119 | 160613 | 161281 | + | Haloacid dehalogenase-like hydrolase, HAD superfamily |
| B624_0120 | 161435 | 162157 | + | DedA protein |
| B624_0121 | 162635 | 163330 | + | ATPase for chromosome partitioning |
| B624_0122 | 163340 | 164404 | + | tadA ATPase |
| B624_0123 | 164407 | 165060 | + | Flp pilus assembly protein |
| B624_0124 | 165060 | 165659 | + | tadC |
| B624_0125 | 165947 | 166231 | + | hypothetical protein |
| B624_0126 | 166240 | 166614 | + | hypothetical protein |
| B624_0127 | 166667 | 167041 | + | oppa3 |
| B624_0128 | 167093 | 168220 | + | BmrU protein |
| B624_0129 | 168424 | 169020 | − | Transcriptional regulator |
| B624_0130 | 169216 | 172125 | + | DNA polymerase III, tau/gamma subunit |
| B624_0131 | 172154 | 172753 | + | recombination protein RecR |
| B624_0132 | 172756 | 173886 | − | sortase family protein |

TABLE 1-continued

Open reading frames of the genome of 35624.

| Gene ID | Start | End | Strand | Predicted Function |
|---|---|---|---|---|
| B624_0134 | 174774 | 176054 | + | hypothetical protein |
| B624_0135 | 176418 | 177179 | + | aspartokinase, alpha and beta subunits |
| B624_0136 | 177238 | 177801 | + | aspartokinase, alpha and beta subunits |
| B624_0137 | 177889 | 178980 | − | aspartate-semialdehyde dehydrogenase |
| B624_0138 | 179148 | 179765 | + | hypothetical protein |
| B624_0139 | 179774 | 181351 | − | Calcineurin-like phosphoesterase |
| B624_0140 | 182040 | 183953 | + | 2-isopropylmalate synthase |
| B624_0141 | 184031 | 186433 | − | penicillin-binding protein |
| B624_0142 | 186811 | 187959 | + | phosphoesterase |
| B624_0143 | 188086 | 191169 | + | DNA topoisomerase I |
| B624_0144 | 191450 | 192067 | + | thymidylate kinase |
| B624_0145 | 192067 | 193215 | + | DNA polymerase III, delta subunit |
| B624_0146 | 193337 | 193888 | + | hypothetical protein |
| B624_0147 | 194034 | 195632 | + | Dipeptidase |
| B624_0148 | 195767 | 197281 | + | formate--tetrahydrofolate ligase |
| B624_0149 | 197684 | 198028 | − | hypothetical protein |
| B624_0150 | 198230 | 198763 | + | hypothetical protein |
| B624_0151 | 198817 | 200259 | − | hypothetical protein |
| B624_0152 | 200521 | 201177 | + | phosphoglycerate mutase family protein |
| B624_0153 | 201278 | 202228 | + | hypothetical protein |
| B624_0154 | 202352 | 203224 | + | Aldose 1-epimerase-like protein |
| B624_0155 | 203348 | 204496 | − | extensin precursor (cell wallhydroxyproline-rich glycoprotein) |
| B624_0156 | 204684 | 204866 | + | hypothetical protein |
| B624_0157 | 205053 | 206570 | + | glutamyl-tRNA synthetase |
| B624_0158 | 207503 | 207988 | + | hypothetical protein |
| B624_0159 | 208388 | 214285 | + | endo-alpha-N-acetylgalactosaminidase |
| B624_0160 | 214390 | 215208 | − | hypothetical protein |
| B624_0161 | 216652 | 218460 | + | hypothetical protein |
| B624_0162 | 218640 | 219317 | + | membrane antigen |
| B624_0163 | 219470 | 220744 | + | Integral membrane protein |
| B624_0164 | 220769 | 222070 | + | possible permease protein of ABC transportersystem |
| B624_0165 | 222107 | 223327 | + | possible permease protein of ABC transportersystem |
| B624_0166 | 223346 | 224140 | + | ABC transporter, ATP-binding protein |
| B624_0167 | 224259 | 224819 | + | FMN-binding domain |
| B624_0168 | 224831 | 225427 | − | Bacterial regulatory proteins, TetR family |
| B624_0169 | 225545 | 227704 | − | phage infection protein |
| B624_0170 | 227704 | 230331 | − | phage infection protein |
| B624_0171 | 230686 | 231969 | + | membrane protein |
| B624_0172 | 232151 | 233602 | + | 6-phosphogluconate dehydrogenase, decarboxylating |
| B624_0173 | 233756 | 234595 | − | 6-phosphogluconolactonase |
| B624_0174 | 234825 | 235847 | − | oxppcycle protein OpcA |
| B624_0175 | 235847 | 237382 | − | glucose-6-phosphate 1-dehydrogenase |
| B624_0176 | 237706 | 239337 | + | dipeptidase |
| B624_0177 | 239417 | 240448 | − | Glycosyltransferase involved in cell wallbiogenesis |
| B624_0178 | 240475 | 241293 | − | transcriptional regulator, TetR family |
| B624_0179 | 241407 | 242675 | + | signal recognition particle-docking protein FtsY |
| B624_0180 | 243046 | 244338 | + | ammonium transporter |
| B624_0181 | 244343 | 244678 | + | Nitrogen regulatory protein P-II |
| B624_0182 | 244790 | 246613 | + | protein-pII; uridylyltransferase |
| B624_0183 | 246653 | 248095 | − | DNA-damage-inducible protein F |
| B624_0184 | 248370 | 249827 | + | replicative DNA helicase |
| B624_0185 | 249830 | 251299 | + | UDP-N-acetylmuramoylalanyl-D-glutamate--2,6-diaminopimelate ligase |
| B624_0186 | 251405 | 252154 | + | cobyric acid synthase |
| B624_0187 | 252306 | 252590 | + | hypothetical protein |
| B624_0188 | 252590 | 254407 | + | ABC1 family |
| B624_0189 | 254428 | 255447 | − | transcriptional regulator, LacI family |
| B624_0190 | 255933 | 257255 | + | ABC superfamily ATP binding cassette transporter |
| B624_0191 | 257546 | 258469 | + | sugar ABC transporter, permease protein |
| B624_0192 | 258493 | 259308 | + | sugar permease of ABC transporter system |
| B624_0193 | 259473 | 261446 | + | hypothetical protein |
| B624_0194 | 262147 | 267966 | + | hypothetical |
| B624_0195 | 268074 | 271778 | + | Glycosyl hydrolase |
| B624_0196 | 271911 | 272741 | + | Hypothetical protein |
| B624_0197 | 272825 | 273835 | − | prsA |
| B624_0198 | 273960 | 274439 | − | hypothetical protein |
| B624_0199 | 274601 | 274891 | + | ribosomal protein S6 |
| B624_0200 | 274951 | 275604 | + | Single-strand binding protein |
| B624_0201 | 275668 | 275913 | + | ribosomal protein S18 |
| B624_0202 | 275936 | 276379 | + | ribosomal protein L9 |
| B624_0203 | 276769 | 277026 | + | ptsH |
| B624_0204 | 277029 | 278705 | + | PTS Enzyme I |
| B624_0205 | 278942 | 279673 | + | glycerol uptake facilitator protein |
| B624_0206 | 279763 | 282468 | − | copper-translocating P-type ATPase |
| B624_0207 | 282580 | 282858 | + | Conserved Protein Domain Family FrmR |

TABLE 1-continued

Open reading frames of the genome of 35624.

| Gene ID | Start | End | Strand | Predicted Function |
|---|---|---|---|---|
| B624_0208 | 282904 | 284325 | + | possible DNA recombination protein RmuC |
| B624_0209 | 284325 | 284951 | + | hypothetical protein |
| B624_0210 | 285048 | 285893 | + | SpoU3 |
| B624_0211 | 286063 | 286359 | + | glutamyl-tRNA(Gln) amidotransferase, C subunit |
| B624_0212 | 286366 | 287904 | + | glutamyl-tRNA(Gln) amidotransferase, A subunit |
| B624_0213 | 287933 | 289429 | + | glutamyl-tRNA(Gln) amidotransferase, B subunit |
| B624_0214 | 289728 | 290789 | + | acetyltransferase |
| B624_0215 | 290803 | 291114 | + | hypothetical protein |
| B624_0216 | 291276 | 293141 | + | hypothetical protein |
| B624_0217 | 293363 | 294973 | + | hypothetical protein |
| B624_0218 | 295182 | 297248 | + | transcription termination factor Rho |
| B624_0219 | 297559 | 297945 | + | chorismate mutase |
| B624_0220 | 298190 | 300151 | + | hypothetical protein |
| B624_0221 | 300383 | 303115 | − | valyl-tRNA synthetase |
| B624_0222 | 303262 | 304785 | − | ABC-type dipeptide transport system, periplasmic component |
| B624_0223 | 304850 | 305533 | − | endonuclease III |
| B624_0224 | 305595 | 306392 | − | Response regulator |
| B624_0225 | 306556 | 307257 | − | hypothetical protein |
| B624_0226 | 307369 | 307950 | − | integral membrane protein |
| B624_0227 | 308187 | 308678 | − | inorganic pyrophosphatase |
| B624_0228 | 308908 | 310980 | − | alpha-amylase family protein |
| B624_0229 | 311386 | 313377 | + | LPXTG-motif cell wall anchor domain-containing protein |
| B624_0230 | 313988 | 315019 | + | homoserine O-succinyltransferase |
| B624_0231 | 315484 | 316293 | + | ATP synthase F0, A subunit |
| B624_0232 | 316400 | 316624 | + | ATP synthase F0, C subunit |
| B624_0233 | 316684 | 317199 | + | ATP synthase F0, B subunit |
| B624_0234 | 317237 | 318070 | + | ATP synthase F1, delta subunit |
| B624_0235 | 318149 | 319777 | + | ATP synthase F1, alpha subunit |
| B624_0236 | 319784 | 320704 | + | ATP synthase F1, gamma subunit |
| B624_0237 | 320716 | 322185 | + | ATP synthase F1, beta subunit |
| B624_0238 | 322188 | 322478 | + | ATP synthase F1, epsilon subunit |
| B624_0239 | 322569 | 323336 | + | nuclease of the RecB family |
| B624_0240 | 323388 | 324374 | − | possible secreted peptidyl-prolyl cis-transisomerase protein |
| B624_0241 | 324455 | 325531 | + | hypothetical protein |
| B624_0242 | 325534 | 326538 | + | hypothetical protein |
| B624_0243 | 326790 | 327761 | + | hypothetical protein |
| B624_0244 | 327850 | 328473 | − | Uncharacterized protein in bacteria |
| B624_0245 | 329012 | 329398 | + | endoribonuclease L-PSP |
| B624_0246 | 329584 | 330498 | + | phospholipid/glycerol acyltransferase |
| B624_0247 | 330595 | 331593 | + | glycerol-3-phosphate dehydrogenase, NAD-dependent |
| B624_0248 | 331783 | 332967 | + | D-ala D-ala ligase |
| B624_0249 | 333223 | 334386 | + | ABC transporter, periplasmic substrate-binding protein |
| B624_0250 | 334401 | 335348 | + | spermidine/putrescine ABC transporter, permease protein |
| B624_0251 | 335348 | 336199 | + | spermidine/putrescine ABC transporter, permeaseprotein |
| B624_0252 | 336207 | 337481 | + | spermidine/putrescine ABC transporter, ATP-binding protein |
| B624_0253 | 337788 | 338828 | + | CAAX amino terminal protease family proteinfamily |
| B624_0254 | 338873 | 339667 | − | Mechanosensitive ion channel family |
| B624_0255 | 339751 | 341181 | − | aspartate ammonia-lyase |
| B624_0256 | 341302 | 342030 | − | Transcriptional regulator |
| B624_0257 | 342124 | 343527 | − | hypothetical protein |
| B624_0258 | 343852 | 344400 | − | methylated-DNA--protein-cysteinemethyltransferase |
| B624_0259 | 345162 | 346055 | + | hypothetical protein |
| B624_0260 | 345928 | 347202 | − | MFS transporter family protein |
| B624_0261 | 347393 | 348406 | − | ribokinase |
| B624_0262 | 348810 | 349001 | + | ribosomal protein L28 |
| B624_0263 | 349104 | 351944 | + | ATP-dependent DNA helicase RecG |
| B624_0264 | 352174 | 352782 | + | methyltransferase |
| B624_0265 | 352812 | 353624 | − | tRNA (guanine-N1)-methyltransferase |
| B624_0266 | 353698 | 355341 | + | protease or peptidase |
| B624_0267 | 355422 | 356399 | + | hypothetical protein |
| B624_0268 | 356482 | 357354 | + | 4-diphosphocytidyl-2C-methyl-D-erythritolsynthase |
| B624_0269 | 357367 | 358041 | + | pyrrolidone-carboxylate peptidase |
| B624_0270 | 358192 | 359766 | + | hypothetical protein |
| B624_0271 | 359884 | 361224 | + | aminopeptidase C |
| B624_0272 | 361519 | 362649 | + | phospho-2-dehydro-3-deoxyheptonate aldolase |
| B624_0273 | 362781 | 364010 | + | phospho-2-dehydro-3-deoxyheptonate aldolase |
| B624_0274 | 364135 | 364845 | + | MTA/SAH nucleosidase |
| B624_0275 | 365099 | 366427 | + | ATPase, histidine kinase domain protein |
| B624_0276 | 366629 | 367330 | + | response regulator |
| B624_0277 | 367583 | 368713 | + | phosphate ABC transporter, phosphate-binding protein |
| B624_0278 | 368927 | 369877 | + | pstC2 |
| B624_0279 | 369880 | 370875 | + | phosphate ABC transporter, permease protein |
| B624_0280 | 370931 | 371707 | + | Phosphate import ATP-binding protein pstB |

TABLE 1-continued

Open reading frames of the genome of 35624.

| Gene ID | Start | End | Strand | Predicted Function |
|---|---|---|---|---|
| B624_0281 | 372005 | 372580 | + | lemA protein |
| B624_0282 | 372647 | 374902 | + | Membrane protein |
| B624_0283 | 374971 | 375831 | + | oxidoreductase, aldo/keto reductase family |
| B624_0284 | 375932 | 376981 | + | inosine-uridine preferring nucleoside hydrolase |
| B624_0285 | 377109 | 377729 | − | 16S rRNA processing protein RimM |
| B624_0286 | 377755 | 377985 | − | KH domain protein |
| B624_0287 | 378009 | 378467 | − | ribosomal protein S16 |
| B624_0288 | 378703 | 379809 | − | Endonuclease/Exonuclease/phosphatase familyfamily |
| B624_0289 | 379889 | 381547 | − | signal recognition particle protein |
| B624_0290 | 381843 | 382748 | + | Co/Zn/Cd cation transporter |
| B624_0291 | 382773 | 384419 | − | cysteinyl-tRNA synthetase |
| B624_0292 | 384518 | 385363 | + | amidotransferase |
| B624_0293 | 385414 | 387687 | + | ABC transporter, ATP-binding protein |
| B624_0294 | 387746 | 388162 | − | plasmid stability protein StbB |
| B624_0295 | 388175 | 388450 | − | Plasmid stability protein |
| B624_0296 | 388609 | 389160 | − | acetolactate synthase, small subunit |
| B624_0297 | 389180 | 391144 | − | acetolactate synthase, large subunit, biosynthetic type |
| B624_0298 | 391308 | 392033 | − | ribonuclease III |
| B624_0299 | 392189 | 392380 | − | Ribosomal protein L32 |
| B624_0300 | 392472 | 393098 | − | Uncharacterized ACR protein |
| B624_0301 | 393191 | 394078 | − | hypothetical protein |
| B624_0302 | 394089 | 394586 | − | pantetheine-phosphate adenylyltransferase |
| B624_0303 | 394860 | 395150 | + | hypothetical protein |
| B624_0304 | 395198 | 396205 | − | K channel, beta subunit |
| B624_0305 | 396379 | 396804 | + | transcription regulator, MerR family |
| B624_0306 | 396910 | 397533 | − | hypothetical protein |
| B624_0307 | 397764 | 399083 | + | nicotinate phosphoribosyltransferase |
| B624_0308 | 399369 | 400142 | + | ribonuclease PH |
| B624_0309 | 400189 | 400944 | + | Ham1 family |
| B624_0310 | 401394 | 402659 | + | Methicillin resistance protein |
| B624_0311 | 402736 | 404043 | + | FemAB family protein |
| B624_0312 | 404096 | 405373 | + | Methicillin resistance protein |
| B624_0313 | 405462 | 406460 | − | auxin efflux carrier |
| B624_0314 | 407182 | 408879 | + | glucose-6-phosphate isomerase |
| B624_0315 | 409515 | 409877 | + | ribosomal protein L19 |
| B624_0316 | 410047 | 410901 | + | lepB2 |
| B624_0317 | 411024 | 411860 | + | ribonuclease HII |
| B624_0318 | 411990 | 413102 | + | transcription regulator, LacI family [imported] |
| B624_0319 | 413261 | 414904 | + | probable sugar kinase |
| B624_0320 | 414992 | 415681 | + | L-ribulose-5-phosphate 4-epimerase |
| B624_0321 | 415916 | 417430 | + | L-arabinose isomerase |
| B624_0322 | 417620 | 418333 | − | Glutamine amidotransferase |
| B624_0323 | 418607 | 420178 | + | hypothetical protein |
| B624_0324 | 420330 | 421694 | + | ABC superfamily ATP binding cassette transporter, membrane protein |
| B624_0325 | 421694 | 422914 | + | permease protein |
| B624_0326 | 422930 | 423562 | + | ABC transporter ATP-binding protein |
| B624_0327 | 423886 | 425706 | − | long-chain-fatty-acid--CoA ligase |
| B624_0329 | 426606 | 429890 | + | ABC transporter |
| B624_0331 | 431272 | 432618 | + | solute binding protein of ABC transportersystem |
| B624_0332 | 432840 | 433799 | + | sugar ABC transporter, permease protein |
| B624_0333 | 433805 | 434809 | + | ABC-type sugar transport systems, permease components |
| B624_0334 | 434999 | 437128 | + | beta-galactosidase |
| B624_0335 | 437175 | 438227 | + | transcription regulator, LacI family [imported] |
| B624_0336 | 438426 | 441116 | + | arabinogalactan endo-1,4-beta-galactosidase |
| B624_0337 | 441755 | 442621 | + | 2,5-didehydrogluconate reductase |
| B624_0338 | 442691 | 443368 | + | extracellular deoxyribonuclease |
| B624_0339 | 443378 | 444745 | − | Hypothetical protein |
| B624_0340 | 445003 | 446367 | + | transport protein, NRAMP family |
| B624_0341 | 446472 | 448073 | − | LinCd |
| B624_0342 | 448412 | 450007 | + | glycosyl transferase CpsD |
| B624_0343 | 450098 | 452029 | + | hypothetical protein |
| B624_0344 | 452091 | 453566 | + | chain length determinant protein |
| B624_0345 | 453574 | 454725 | + | glycosyl transferase, group 1family protein |
| B624_0346 | 454725 | 456065 | + | Glycosyltransferase protein |
| B624_0347 | 456065 | 457126 | + | UDP-glucuronate 5'-epimerase |
| B624_0348 | 457201 | 458448 | + | UDP-glucose 6-dehydrogenase |
| B624_0349 | 458489 | 459550 | + | glycosyl transferase, group 1 family protein |
| B624_0350 | 459581 | 460408 | + | NAD dependent epimerase/dehydratase family |
| B624_0351 | 460446 | 460952 | + | acetyltransferase |
| B624_0352 | 460985 | 461998 | + | Glycosyl transferase |
| B624_0353 | 462020 | 463360 | + | polymerase involved in polysaccharide synthesis |
| B624_0354 | 463363 | 464292 | + | rhamnosyl transferase |
| B624_0355 | 464311 | 465753 | + | flippase protein involved in polysaccharide biosynthesis |
| B624_0356 | 465774 | 466280 | + | acetyltransferase |
| B624_0357 | 466366 | 467514 | − | NAD-dependent epimerase/dehydratase family protein |

TABLE 1-continued

Open reading frames of the genome of 35624.

| Gene ID | Start | End | Strand | Predicted Function |
|---|---|---|---|---|
| B624_0358 | 467785 | 468615 | − | integrase, catalytic region |
| B624_0359 | 468615 | 468770 | − | transposase IS3/IS911 family protein |
| B624_0360 | 469189 | 470208 | + | dTDP-glucose 4,6-dehydratase |
| B624_0361 | 470218 | 471303 | + | dTDP-4-dehydrorhamnose 3,5-epimerase/dTDP-4-dehydrorhamnose reductase |
| B624_0362 | 471349 | 472245 | + | glucose-1-phosphate thymidylyltransferase |
| B624_0364 | 472715 | 472858 | + | hypothetical protein |
| B624_0365 | 473371 | 473802 | − | hypothetical protein |
| B624_0366 | 474083 | 474640 | − | phosphotyrosine protein phosphatase |
| B624_0367 | 474825 | 475331 | − | hypothetical protein |
| B624_0368 | 475655 | 475867 | − | transcriptional regulator |
| B624_0369 | 475860 | 476282 | − | hypothetical protein |
| B624_0370 | 476415 | 477422 | − | hypothetical protein |
| B624_0371 | 477495 | 477866 | − | thioredoxin 2 |
| B624_0372 | 478122 | 478751 | + | hypothetical protein |
| B624_0373 | 478880 | 479734 | + | alpha beta hydrolase |
| B624_0374 | 479747 | 481036 | + | npyl |
| B624_0375 | 481065 | 481475 | + | glycine cleavage system H protein |
| B624_0376 | 481547 | 482875 | + | hypothetical protein |
| B624_0377 | 482940 | 485453 | + | protease II |
| B624_0378 | 485521 | 486549 | + | 3-isopropylmalate dehydrogenase |
| B624_0379 | 486610 | 487692 | + | lipoate-protein ligase a |
| B624_0380 | 487934 | 488650 | + | probable transcriptional regulator |
| B624_0381 | 488766 | 491069 | + | penicillin-binding protein |
| B624_0382 | 491264 | 492634 | + | NADH-dependent flavin oxidoreductase |
| B624_0383 | 492807 | 493955 | − | dihydroorotate dehydrogenase |
| B624_0384 | 494310 | 495122 | + | DeoR-type regulator |
| B624_0385 | 495118 | 496365 | + | galactose-1-phosphate uridylyltransferase |
| B624_0386 | 496385 | 497632 | + | galactokinase |
| B624_0387 | 497718 | 497987 | + | ACT domain protein |
| B624_0388 | 498126 | 499487 | + | hypothetical protein |
| B624_0389 | 499800 | 500396 | − | spoU |
| B624_0390 | 500480 | 501463 | + | mutY |
| B624_0391 | 501531 | 502250 | + | hypothetical protein |
| B624_0392 | 502408 | 505968 | + | DNA-directed RNA polymerase, beta subunit |
| B624_0393 | 506139 | 510173 | + | DNA-directed RNA polymerase, beta-prime subunit |
| B624_0394 | 510338 | 510967 | − | FHA domain protein |
| B624_0395 | 510986 | 511498 | − | hypothetical protein |
| B624_0396 | 511528 | 512457 | − | phosphoprotein phosphatase |
| B624_0397 | 512457 | 514967 | − | membrane protein |
| B624_0398 | 514967 | 516187 | − | Protein of unknown function family |
| B624_0399 | 516215 | 517585 | − | moxR2 |
| B624_0400 | 517599 | 523580 | − | fibronectin type III domain-containing protein |
| B624_0401 | 523750 | 525168 | − | serine/threonine protein kinase |
| B624_0402 | 525300 | 529592 | + | uvrd4 |
| B624_0403 | 529592 | 533620 | + | UvrD/REP helicase domain protein |
| B624_0404 | 533836 | 535152 | + | transport protein |
| B624_0405 | 535491 | 536243 | + | dihydrodipicolinate reductase |
| B624_0406 | 536409 | 537311 | + | dihydrodipicolinate synthase |
| B624_0407 | 537399 | 539246 | + | metallo-beta-lactamase superfamily protein |
| B624_0408 | 539291 | 541897 | + | Peptidase family M1 domain protein |
| B624_0409 | 542078 | 542971 | + | hypothetical protein |
| B624_0411 | 543954 | 545336 | + | phosphoglucosamine mutase |
| B624_0412 | 545362 | 546012 | + | polypeptide deformylase |
| B624_0413 | 546012 | 547472 | + | DNA polymerase III |
| B624_0414 | 547492 | 547620 | + | hypothetical protein |
| B624_0415 | 547858 | 548979 | + | peptide chain release factor 2 |
| B624_0416 | 548991 | 550121 | + | ftsE |
| B624_0417 | 550135 | 551055 | + | cell division ABC transporter, permease proteinFtsX |
| B624_0418 | 551161 | 552519 | + | CHAP domain containing protein |
| B624_0419 | 552673 | 553146 | + | SsrA-binding protein |
| B624_0420 | 553312 | 554265 | + | amino acid ABC transporter, permease protein |
| B624_0421 | 554479 | 555420 | + | hisj5 |
| B624_0422 | 555554 | 556546 | + | amino acid ABC transporter, permease protein |
| B624_0423 | 556566 | 557393 | + | glutamine ABC transporter, ATP-binding protein |
| B624_0424 | 557604 | 559493 | + | glucosamine--fructose-6-phosphateaminotransferase, isomerizing |
| B624_0425 | 559510 | 560271 | + | Pseudouridylate synthases |
| B624_0426 | 560313 | 560525 | − | hypothetical protein |
| B624_0427 | 560565 | 561554 | − | transcriptional regulator, LacI family |
| B624_0428 | 561794 | 562717 | + | sugar ABC transporter, permease protein |
| B624_0429 | 562776 | 563780 | + | ABC-type sugar transport system, permease component |
| B624_0430 | 563975 | 566047 | + | beta-D-galactosidase |
| B624_0431 | 566169 | 567185 | + | transcriptional regulator, LacI family |
| B624_0432 | 567311 | 569008 | − | alpha-L-arabinofuranosidase |
| B624_0433 | 569168 | 570517 | + | solute binding protein of ABC transportersystem |

TABLE 1-continued

Open reading frames of the genome of 35624.

| Gene ID | Start | End | Strand | Predicted Function |
|---|---|---|---|---|
| B624_0434 | 570852 | 572192 | + | probable solute binding protein of ABCtransporter system for sugars |
| B624_0435 | 572341 | 573729 | + | sugar binding protein Sbp |
| B624_0436 | 573795 | 574562 | − | transcription activator, probable Baf family[imported] |
| B624_0437 | 574688 | 576304 | + | ABC transporter, periplasmic substrate-bindingprotein |
| B624_0438 | 576372 | 577346 | + | membrane protein |
| B624_0439 | 577346 | 578245 | + | peptide ABC transporter, permease protein |
| B624_0440 | 578245 | 579033 | + | ABC transporter, nucleotide binding/ATPase protein |
| B624_0441 | 579029 | 579811 | + | ABC transporter, ATP-binding protein |
| B624_0442 | 580296 | 581360 | + | cystathionine beta-synthase |
| B624_0443 | 581455 | 582636 | + | cystathionine gamma-synthase |
| B624_0444 | 582780 | 584501 | − | ErfK/YbiS/YcfS/YnhG family |
| B624_0445 | 584661 | 586613 | + | ATP-dependent DNA helicase RecQ |
| B624_0446 | 586729 | 587220 | + | autoinducer-2 production protein LuxS |
| B624_0447 | 587378 | 587917 | + | acetyltransferase, GNAT family |
| B624_0448 | 588181 | 589317 | − | hypothetical protein |
| B624_0449 | 589890 | 591347 | − | amino acid permease |
| B624_0450 | 591536 | 592891 | + | alanine racemase |
| B624_0451 | 593099 | 594370 | + | deoxyguanosinetriphosphate triphosphohydrolase |
| B624_0452 | 594537 | 596642 | + | DNA primase |
| B624_0453 | 596838 | 597710 | + | pyridoxine biosynthesis protein |
| B624_0454 | 597799 | 598434 | + | glutamine amidotransferase subunit PdxT |
| B624_0455 | 598495 | 600156 | + | aminotransferase, class I |
| B624_0456 | 600514 | 601443 | + | possible beta-aspartyl-peptidase |
| B624_0457 | 601574 | 601726 | − | hypothetical protein |
| B624_0458 | 601995 | 603179 | + | Di- and tricarboxylate transporters |
| B624_0459 | 603210 | 603467 | − | hypothetical protein |
| B624_0460 | 603651 | 605888 | − | similar to alpha-L-arabinofuranosidase A |
| B624_0461 | 605923 | 606921 | + | transcriptional regulator |
| B624_0462 | 607014 | 608219 | − | Hypothetical protein |
| B624_0463 | 608621 | 609373 | + | ABC transporter, ATP-binding protein |
| B624_0464 | 609373 | 610545 | + | S-layer domain |
| B624_0465 | 610560 | 612116 | + | ABC transporter, ATP-binding protein |
| B624_0466 | 612106 | 614232 | − | 1-deoxyxylulose-5-phosphate synthase |
| B624_0467 | 614478 | 615467 | + | oxidoreductase |
| B624_0468 | 615566 | 616069 | + | phosphoribosylaminoimidazole carboxylase, catalytic subunit |
| B624_0469 | 616095 | 617231 | + | phosphoribosylaminoimidazole carboxylase, ATPasesubunit |
| B624_0470 | 617243 | 617668 | + | furB |
| B624_0472 | 618183 | 619103 | + | possible solute binding protein of ABCtransporter system |
| B624_0473 | 619367 | 621439 | + | Phosphoglycerol transferase |
| B624_0474 | 621563 | 623197 | + | Aldehyde dehydrogenase (NAD(P)(+)) |
| B624_0475 | 623577 | 624842 | − | phosphoribosylamine--glycine ligase |
| B624_0476 | 624872 | 625906 | − | phosphoribosylformylglycinamidine cyclo-ligase |
| B624_0477 | 626029 | 627537 | − | amidophosphoribosyltransferase |
| B624_0478 | 627944 | 628726 | − | glutamine ABC transporter, ATP-binding protein |
| B624_0479 | 628726 | 629610 | − | amino acid ABC transporter, permease protein |
| B624_0480 | 629723 | 630583 | − | amino acid ABC transporter, periplasmic aminoacid-binding protein |
| B624_0481 | 630788 | 631255 | − | hypothetical protein |
| B624_0482 | 631328 | 632698 | − | Atz/Trz family protein |
| B624_0483 | 632741 | 634222 | − | S-adenosyl-L-homocysteine hydrolase, NAD bindingdomain |
| B624_0484 | 634405 | 635991 | + | structural gene for ultraviolet resistance |
| B624_0485 | 635991 | 636206 | + | hypothetical protein |
| B624_0486 | 636246 | 637220 | − | K channel, beta subunit |
| B624_0487 | 637331 | 638293 | − | transcriptional regulator, HTH_1 family |
| B624_0488 | 638512 | 640023 | + | Na/H antiporter |
| B624_0489 | 640043 | 640699 | − | hypothetical protein |
| B624_0490 | 640699 | 642066 | − | hypothetical protein |
| B624_0491 | 642042 | 643337 | − | hypothetical protein |
| B624_0492 | 643478 | 647209 | − | phosphoribosylformylglycinamidine synthase |
| B624_0493 | 647275 | 648024 | − | phosphoribosylaminoimidazole-succinocarboxamidesynthase |
| B624_0494 | 648420 | 649754 | − | phosphoribosylglycinamide formyltransferase |
| B624_0495 | 649928 | 651085 | + | type 1 capsular polysaccharide biosynthesisprotein J (capJ) |
| B624_0496 | 651238 | 652260 | − | hypothetical protein |
| B624_0497 | 652822 | 653880 | + | transporter protein |
| B624_0498 | 654599 | 654967 | + | ribosomal protein S12 |
| B624_0499 | 654976 | 655443 | + | ribosomal protein S7 |
| B624_0500 | 655478 | 657598 | + | translation elongation factor G |
| B624_0501 | 657774 | 658970 | + | translation elongation factor Tu |
| B624_0502 | 659184 | 659909 | + | hypothetical protein |
| B624_0503 | 660049 | 660864 | + | transcriptional regulator, LysR family |

TABLE 1-continued

Open reading frames of the genome of 35624.

| Gene ID | Start | End | Strand | Predicted Function |
|---|---|---|---|---|
| B624_0504 | 661037 | 662098 | + | membrane protein |
| B624_0505 | 662161 | 662643 | − | Membrane protein |
| B624_0506 | 662721 | 663086 | − | CrcB protein |
| B624_0507 | 663086 | 663619 | − | protein with similarity to CrcB |
| B624_0508 | 663631 | 663987 | + | hypothetical protein |
| B624_0509 | 664023 | 665063 | + | alcohol dehydrogenase, zinc-containing |
| B624_0510 | 665416 | 665625 | + | hypothetical protein |
| B624_0511 | 665652 | 667028 | − | Hypothetical protein |
| B624_0512 | 667295 | 667462 | − | hypothetical protein |
| B624_0513 | 667902 | 670487 | + | excinuclease ABC, subunit A |
| B624_0514 | 670548 | 671903 | + | MATE efflux family protein |
| B624_0515 | 671914 | 672603 | + | endonuclease III |
| B624_0516 | 672783 | 673076 | − | hypothetical protein |
| B624_0517 | 673095 | 673766 | + | galactoside O-acetyltransferase |
| B624_0519 | 674207 | 675292 | + | possible integral membrane permease protein |
| B624_0520 | 675318 | 675902 | + | Beta-glucuronidase |
| B624_0521 | 676090 | 677523 | − | glutamine synthetase, type I |
| B624_0522 | 677846 | 678625 | + | hypothetical protein |
| B624_0523 | 678712 | 680199 | − | dihydrolipoamide dehydrogenase |
| B624_0524 | 680351 | 680971 | − | integral membrane protein |
| B624_0525 | 681063 | 682427 | + | widely conserved protein in peptidase ordeacetlylase family |
| B624_0526 | 682730 | 683326 | + | ABC superfamily ATP binding cassette transporter, membrane protein |
| B624_0527 | 683329 | 684801 | + | ABC transporter, ATP-binding protein |
| B624_0528 | 684801 | 685625 | + | possible permease protein of ABC transporter forcobalt |
| B624_0529 | 685824 | 686699 | + | spoU rRNA methylase family protein [imported] |
| B624_0530 | 686756 | 687820 | + | phenylalanyl-tRNA synthetase, alpha subunit |
| B624_0531 | 687831 | 690437 | + | phenylalanyl-tRNA synthetase, beta subunit |
| B624_0532 | 690471 | 691154 | + | hypothetical protein |
| B624_0533 | 691256 | 692347 | + | N-acetyl-gamma-glutamyl-phosphate reductase |
| B624_0534 | 692347 | 693519 | + | ornithine acetyltransferase/N-acetylglutamate synthase protein |
| B624_0535 | 693659 | 694612 | + | acetylglutamate kinase |
| B624_0536 | 694605 | 695897 | + | acetylornithine aminotransferase |
| B624_0537 | 695944 | 696906 | + | ornithine carbamoyltransferase |
| B624_0538 | 696906 | 697415 | + | arginine repressor |
| B624_0539 | 697501 | 698736 | + | argininosuccinate synthase |
| B624_0540 | 699184 | 700653 | + | argininosuccinate lyase |
| B624_0541 | 701005 | 701196 | + | Sulfur transfer protein involved in thiamine biosynthesis |
| B624_0542 | 701211 | 702077 | + | thiG protein |
| B624_0543 | 702157 | 702963 | + | moeB |
| B624_0544 | 703023 | 703376 | + | rhodanese-like domain protein |
| B624_0545 | 703550 | 704071 | + | HD domain protein |
| B624_0546 | 704071 | 704835 | + | hypothetical protein |
| B624_0547 | 704964 | 706283 | + | tyrosyl-tRNA synthetase |
| B624_0548 | 706314 | 708086 | + | hypothetical protein |
| B624_0549 | 708098 | 709135 | + | Sugar phosphatases of the HADsuperfamily |
| B624_0550 | 709395 | 710165 | + | hemolysin A |
| B624_0551 | 710153 | 710824 | − | hypothetical protein |
| B624_0552 | 710965 | 711624 | − | similar to a bacterial K( )-uptake system |
| B624_0553 | 711678 | 713141 | − | Cation transport protein domain protein |
| B624_0554 | 713388 | 714407 | + | poly(P)/ATP-NAD kinase |
| B624_0555 | 714410 | 716233 | + | DNA repair protein RecN |
| B624_0556 | 716266 | 716910 | + | hydrolase, haloacid dehalogenase-like family |
| B624_0557 | 717154 | 717525 | + | transcriptional regulator, GntR family |
| B624_0558 | 717544 | 718467 | + | ABC transporter, ATP-binding protein |
| B624_0559 | 718477 | 719091 | + | hypothetical protein |
| B624_0560 | 719187 | 719903 | + | hypothetical protein |
| B624_0561 | 719985 | 722768 | − | calcium-translocating P-type ATPase, PMCA-type |
| B624_0562 | 722966 | 723238 | + | hypothetical protein |
| B624_0563 | 723291 | 724778 | − | threonine synthase |
| B624_0564 | 725001 | 725699 | + | serine hydroxymethyltransferase |
| B624_0565 | 725707 | 727116 | + | gamma-glutamyl phosphate reductase |
| B624_0566 | 727116 | 727694 | + | phosphoribosylformylglycinamidine (FGAM) synthase, synthetase domain protein |
| B624_0567 | 727694 | 728476 | + | nicotinate (nicotinamide) nucleotideadenylyltransferase |
| B624_0568 | 728580 | 729779 | − | possible B-hexosaminidase |
| B624_0569 | 729952 | 733203 | + | hypothetical protein |
| B624_0570 | 733340 | 733834 | + | phosphinothricin acetyltransferase |
| B624_0571 | 734033 | 734629 | + | peptidyl-tRNA hydrolase |
| B624_0572 | 734622 | 738203 | + | transcription-repair coupling factor |
| B624_0573 | 738346 | 739290 | + | oxidoreductase |
| B624_0574 | 739444 | 740739 | + | phosphopyruvate hydratase |
| B624_0575 | 740833 | 741423 | + | hypothetical protein |
| B624_0576 | 741423 | 741986 | + | hypothetical protein |

TABLE 1-continued

Open reading frames of the genome of 35624.

| Gene ID | Start | End | Strand | Predicted Function |
|---|---|---|---|---|
| B624_0577 | 742052 | 743050 | + | Ppx/GppA phosphatase |
| B624_0578 | 743410 | 744711 | + | IS30 family, transposase [imported] |
| B624_0580 | 745605 | 747062 | + | L-serine dehydratase 1 |
| B624_0581 | 747207 | 747611 | + | peptidyl-prolyl cis-trans isomerase, FKBP-type |
| B624_0582 | 747713 | 748189 | + | transcription elongation factor GreA |
| B624_0583 | 748250 | 749191 | − | hemolysin |
| B624_0584 | 749316 | 750086 | + | hypothetical protein |
| B624_0585 | 750252 | 751736 | + | histidine kinase-like protein |
| B624_0586 | 751815 | 752090 | − | hypothetical protein |
| B624_0587 | 752207 | 754030 | − | FtsK cell division protein |
| B624_0588 | 754203 | 755633 | − | Cell envelope-related function transcriptional attenuator common domain protein |
| B624_0589 | 755815 | 756180 | + | whiB1 |
| B624_0590 | 756227 | 759319 | + | membrane protein |
| B624_0591 | 759319 | 760857 | + | Large exoproteins involved in heme utilization or adhesion |
| B624_0592 | 760966 | 761391 | − | hypothetical protein |
| B624_0593 | 761480 | 762283 | + | Hypothetical protein |
| B624_0594 | 762332 | 763015 | + | Phosphoribosyl transferase domain protein |
| B624_0595 | 762937 | 763320 | − | hypothetical protein |
| B624_0596 | 763391 | 764464 | − | sensory box histidine kinase |
| B624_0597 | 764464 | 765183 | − | DNA-binding response regulator MtrA |
| B624_0598 | 765222 | 767471 | − | 1,4-alpha-glucan branching enzyme |
| B624_0599 | 767649 | 768239 | + | possible transcriptional regulator |
| B624_0600 | 768351 | 768872 | + | 2C-methyl-D-erythritol 2,4-cyclodiphosphatesynthase |
| B624_0601 | 768930 | 769760 | + | zinc ABC transporter, permease protein |
| B624_0602 | 769830 | 770717 | − | ABC transporter, ATP-binding protein |
| B624_0603 | 770893 | 772086 | − | possible solute binding protein of ABCtransporter system |
| B624_0604 | 772190 | 773062 | + | methylenetetrahydrofolate dehydrogenase/cyclohydrolase |
| B624_0605 | 773185 | 774657 | + | 30S ribosomal protein S1 |
| B624_0606 | 774834 | 775448 | + | dephospho-CoA kinase |
| B624_0607 | 775463 | 777571 | + | excinuclease ABC, B subunit |
| B624_0608 | 777743 | 778726 | + | TerC family protein |
| B624_0609 | 778897 | 780336 | + | pyruvate kinase |
| B624_0610 | 780490 | 781086 | − | possible NTP pyrophosphatase in MutT family |
| B624_0611 | 781432 | 782214 | + | response regulator |
| B624_0612 | 782278 | 785127 | + | DNA polymerase I |
| B624_0613 | 785300 | 786217 | + | hypothetical protein |
| B624_0614 | 786266 | 786937 | + | MutT/nudix family protein |
| B624_0615 | 786994 | 789132 | + | glycogen operon protein GlgX |
| B624_0616 | 789186 | 789413 | + | hypothetical protein |
| B624_0617 | 789420 | 790067 | + | hypothetical protein |
| B624_0618 | 790243 | 790794 | − | DNA-3-methyladenine glycosylase I |
| B624_0619 | 791884 | 792942 | − | hypothetical protein |
| B624_0620 | 793226 | 793780 | + | hypothetical protein |
| B624_0624 | 794937 | 795989 | − | integrase/recombinase XerC, probable [imported] |
| B624_0625 | 795989 | 796951 | − | probable integrase/recombinase |
| B624_0626 | 796951 | 798273 | − | integrase/recombinase |
| B624_0627 | 798284 | 799564 | − | IS3-Spn1, transposase |
| B624_0628 | 799635 | 800477 | − | Transposase subunit |
| B624_0629 | 800762 | 802579 | − | hypothetical Protein |
| B624_0630 | 803748 | 804065 | − | hypothetical protein |
| B624_0631 | 804667 | 808221 | + | DNA polymerase III, alpha chain |
| B624_0632 | 808297 | 808743 | + | hypothetical protein |
| B624_0633 | 808952 | 810826 | + | antigen, 67 kDa |
| B624_0634 | 810916 | 811413 | + | NH2-acetyltransferase |
| B624_0635 | 817553 | 818377 | − | 2,5-diketo-D-gluconic acid reductase A |
| B624_0636 | 818484 | 819956 | + | sugar kinase, FGGY family |
| B624_0637 | 819972 | 820262 | + | Acylphosphatase |
| B624_0638 | 820367 | 821761 | + | histidinol dehydrogenase |
| B624_0639 | 821761 | 822918 | + | histidinol-phosphate aminotransferase |
| B624_0640 | 823007 | 823603 | + | imidazoleglycerol-phosphate dehydratase |
| B624_0641 | 823606 | 824397 | + | hypothetical protein |
| B624_0642 | 824435 | 825079 | + | imidazole glycerol phosphate synthase, glutamineamidotransferase subunit |
| B624_0643 | 825152 | 825874 | + | HisA/TrpF protein |
| B624_0644 | 826039 | 827415 | − | hypothetical protein |
| B624_0645 | 827564 | 828898 | + | Glutamine synthetase, catalytic domain |
| B624_0646 | 829137 | 829604 | + | possible arabinose efflux permease |
| B624_0647 | 829657 | 830625 | − | hypothetical protein |
| B624_0648 | 830625 | 834758 | − | ATP-dependent helicase HrpA |
| B624_0649 | 834751 | 835404 | − | hypothetical protein |
| B624_0650 | 835563 | 837065 | + | GTP-binding protein |
| B624_0651 | 837249 | 838208 | + | L-lactate dehydrogenase |
| B624_0652 | 838356 | 839291 | − | cation efflux system protein |
| B624_0653 | 839460 | 840182 | − | LexA repressor |

TABLE 1-continued

Open reading frames of the genome of 35624.

| Gene ID | Start | End | Strand | Predicted Function |
|---|---|---|---|---|
| B624_0654 | 840333 | 840680 | + | LysM domain protein |
| B624_0655 | 840736 | 841173 | + | transcriptional regulator NrdR |
| B624_0656 | 841314 | 842510 | − | D-3-phosphoglycerate dehydrogenase |
| B624_0657 | 842524 | 844800 | − | Superfamily I DNA and RNA helicases |
| B624_0658 | 845133 | 845651 | + | hypothetical protein |
| B624_0659 | 845654 | 846730 | + | S-adenosyl-methyltransferase MraW |
| B624_0660 | 846740 | 847186 | + | hypothetical protein |
| B624_0661 | 847186 | 848985 | + | penicillin-binding protein |
| B624_0662 | 849015 | 849884 | + | hypothetical protein |
| B624_0663 | 849936 | 851384 | + | UDP-N-acetylmuramoylalanyl-D-glutamyl-2,6-diaminopimelate--D-alanyl-D-alanylligase |
| B624_0664 | 851432 | 852535 | + | rfe1 |
| B624_0665 | 852593 | 854035 | + | UDP-N-acetylmuramoylalanine--D-glutamate ligase |
| B624_0666 | 854025 | 855239 | + | cell division protein, FtsW/RodA/SpoVE family |
| B624_0667 | 855258 | 856436 | + | UDP-N-acetylglucosamine--N-acetylmuramyl-(pentapeptide)pyrophosphoryl-undecaprenol N-acetylglucosaminetransferase |
| B624_0668 | 856540 | 858075 | + | UDP-N-acetylmuramate--alanine ligase |
| B624_0669 | 858078 | 859139 | + | Cell division septal protein |
| B624_0670 | 859883 | 860983 | + | hypothetical protein |
| B624_0671 | 861130 | 861813 | + | von Willebrand factor |
| B624_0672 | 861906 | 862391 | + | D-tyrosyl-tRNA(Tyr) deacylase |
| B624_0673 | 862494 | 863735 | − | glucose/galactose transporter |
| B624_0674 | 863844 | 864230 | − | Lactoylglutathione lyase and related lyases |
| B624_0675 | 864308 | 865201 | − | fructokinase |
| B624_0676 | 865277 | 866488 | − | transcription regulator ROK family |
| B624_0677 | 866715 | 867626 | + | glucokinase |
| B624_0678 | 867792 | 868913 | − | NagC/XylR-type transcriptional regulator |
| B624_0679 | 869251 | 870060 | + | glucosamine-6-phosphate isomerase |
| B624_0680 | 870119 | 871393 | + | N-acetylglucosamine-6-phosphate deacetylase |
| B624_0681 | 871676 | 873307 | + | dipeptide ABC transporter, dipeptide-bindingprotein |
| B624_0682 | 873480 | 874568 | + | oligopeptide ABC transporter, permease protein |
| B624_0683 | 874573 | 875739 | + | dipeptide ABC transporter, permease protein |
| B624_0684 | 875746 | 877452 | + | ATP binding protein of ABC transporter |
| B624_0685 | 877508 | 878026 | − | MutT/nudix family protein |
| B624_0686 | 878078 | 879670 | − | Xaa-Pro aminopeptidase I |
| B624_0687 | 879977 | 880954 | − | hypothetical protein |
| B624_0689 | 882044 | 883672 | + | folC |
| B624_0690 | 883736 | 887410 | + | SMC family, C-terminal domain family |
| B624_0691 | 887535 | 888527 | − | hypothetical protein |
| B624_0692 | 888652 | 890202 | − | mure1 |
| B624_0693 | 890341 | 891126 | + | RNA polymerase sigma-70 factor, ECF subfamily |
| B624_0694 | 891129 | 891446 | + | hypothetical protein |
| B624_0695 | 891719 | 892660 | − | Aldose 1-epimerase superfamily |
| B624_0696 | 892788 | 893741 | − | Aldose 1-epimerase superfamily |
| B624_0697 | 894032 | 895021 | + | hydroxymethylbutenyl pyrophosphate reductase |
| B624_0698 | 895067 | 895573 | − | transcriptional regulator |
| B624_0699 | 895670 | 896725 | − | glyceraldehyde-3-phosphate dehydrogenase, typeI |
| B624_0700 | 896968 | 897690 | − | Thiamin pyrophosphokinase, catalytic domainfamily |
| B624_0702 | 899298 | 899930 | + | Translation initiation factor IF-3, C-terminaldomain |
| B624_0703 | 899923 | 900105 | + | ribosomal protein L35 |
| B624_0704 | 900161 | 900541 | + | ribosomal protein L20 |
| B624_0705 | 900614 | 901537 | + | Integrase |
| B624_0706 | 901668 | 904511 | + | ABC transporter, ATP-binding protein |
| B624_0707 | 904776 | 905612 | + | Soj family protein |
| B624_0708 | 905634 | 906545 | + | chromosome segregation and condensation protein ScpA |
| B624_0709 | 906561 | 907274 | + | Transcriptional regulator |
| B624_0710 | 907409 | 908233 | + | MutT/nudix family protein |
| B624_0711 | 908296 | 909573 | + | quinolinate synthetase complex, A subunit |
| B624_0712 | 909668 | 911296 | + | L-aspartate oxidase |
| B624_0713 | 911303 | 912193 | + | nicotinate-nucleotide pyrophosphorylase |
| B624_0714 | 912199 | 913443 | + | possible pyridoxal-phosphate-dependentaminotransferase |
| B624_0715 | 913478 | 914824 | + | major facilitator family transporter |
| B624_0716 | 915142 | 917070 | + | GTP-binding elongation factor TypA/BipA |
| B624_0717 | 917173 | 917616 | + | Alcohol dehydrogenase, class IV |
| B624_0718 | 917699 | 918673 | + | prephenate dehydratase |
| B624_0719 | 918670 | 919734 | + | prephenate dehydrogenase |
| B624_0720 | 919947 | 920201 | + | hypothetical protein |
| B624_0721 | 920239 | 921303 | + | phage integrase family protein |
| B624_0722 | 921559 | 923196 | + | DppA2 |
| B624_0723 | 923500 | 924423 | + | ABC-type dipeptide/oligopeptide/nickel transport systems, permease components |
| B624_0724 | 924445 | 925446 | + | dppC |
| B624_0725 | 925472 | 927478 | + | ABC-type transporter, duplicated ATPasecomponent |
| B624_0726 | 927793 | 928650 | − | exodeoxyribonuclease III |
| B624_0727 | 928775 | 929626 | + | hypothetical protein |

TABLE 1-continued

Open reading frames of the genome of 35624.

| Gene ID | Start | End | Strand | Predicted Function |
|---|---|---|---|---|
| B624_0728 | 929645 | 930400 | + | ABC-type Mn2+/Zn2+ transport systems, permease components |
| B624_0729 | 930390 | 931658 | + | RNA methyltransferase, TrmA family |
| B624_0730 | 931673 | 932365 | + | lipoprotein |
| B624_0731 | 932483 | 935032 | + | ATPase, P-type (transporting), HAD superfamily, subfamily IC |
| B624_0732 | 935156 | 937852 | + | aconitate hydratase 1 |
| B624_0733 | 938001 | 938360 | + | DNA-damage-inducible protein J |
| B624_0734 | 938363 | 938851 | + | hypothetical protein |
| B624_0735 | 938917 | 941019 | − | Uncharacterized protein |
| B624_0736 | 941112 | 941750 | − | hypothetical protein |
| B624_0737 | 941793 | 942548 | − | DNA-binding response regulator |
| B624_0738 | 942553 | 943812 | − | histidine kinase sensor |
| B624_0739 | 944117 | 944959 | + | hypothetical protein |
| B624_0740 | 945143 | 946039 | + | membrane protein |
| B624_0741 | 946182 | 947195 | + | integral membrane protein with duf6 |
| B624_0742 | 947234 | 947962 | − | GTP pyrophosphokinase |
| B624_0743 | 948103 | 949554 | + | tRNA-i(6)A37 thiotransferase enzyme MiaB |
| B624_0744 | 949568 | 950551 | + | tRNA delta(2)-isopentenylpyrophosphatetransferase |
| B624_0745 | 950591 | 951337 | − | Fic protein family family |
| B624_0746 | 951549 | 954437 | + | cell division protein FtsK |
| B624_0747 | 954620 | 955267 | + | CDP-diacylglycerol--glycerol-3-phosphate3-phosphatidyltransferase |
| B624_0748 | 955282 | 955812 | + | competence/damage-inducible protein CinA domainprotein |
| B624_0749 | 955875 | 956387 | + | Transcriptional regulators |
| B624_0750 | 956502 | 956732 | + | hypothetical protein |
| B624_0751 | 957036 | 958226 | + | recA protein |
| B624_0752 | 958232 | 958822 | + | regulatory protein RecX |
| B624_0753 | 959005 | 959544 | + | hypothetical protein |
| B624_0754 | 959702 | 960361 | + | S30AE family protein |
| B624_0755 | 960526 | 963417 | + | preprotein translocase, SecA subunit |
| B624_0758 | 964674 | 965717 | + | anthranilate phosphoribosyltransferase |
| B624_0759 | 965964 | 966656 | − | hypothetical protein |
| B624_0760 | 966717 | 967418 | + | phospholipid/glycerol acyltransferase |
| B624_0761 | 967476 | 969746 | − | serine/threonine protein kinase |
| B624_0762 | 969893 | 970972 | − | probable bifunctional short chain isoprenyl diphosphate synthase |
| B624_0763 | 971179 | 971838 | + | hypothetical protein |
| B624_0764 | 972044 | 973465 | + | RNA polymerase principal sigma factor; sigma 70 |
| B624_0765 | 973526 | 975799 | + | DNA gyrase, subunit B |
| B624_0766 | 975969 | 977192 | + | MFS family major facilitator transporter |
| B624_0767 | 977239 | 978228 | + | ribokinase |
| B624_0768 | 978247 | 982977 | + | DEAD/DEAH box helicase domain protein |
| B624_0769 | 982994 | 983779 | − | hypothetical protein |
| B624_0770 | 983927 | 986653 | − | DNA gyrase A subunit |
| B624_0771 | 986904 | 988169 | + | hypothetical protein |
| B624_0772 | 988185 | 989273 | − | hypothetical protein |
| B624_0773 | 989432 | 989722 | + | hypothetical protein |
| B624_0774 | 989725 | 990198 | + | deoxyuridine 5triphosphate nucleotidohydrolase |
| B624_0775 | 990335 | 992656 | + | GTP pyrophosphokinase |
| B624_0777 | 993226 | 994425 | + | Site-specific recombinase XerD |
| B624_0778 | 994425 | 995387 | + | probable integrase/recombinase |
| B624_0779 | 995387 | 996439 | + | integrase/recombinase XerC, probable |
| B624_0780 | 996532 | 997095 | − | integrase catalytic subunit |
| B624_0781 | 997107 | 997619 | − | hypothetical protein |
| B624_0782 | 997719 | 998255 | − | peptidyl-prolyl cis-trans isomerase |
| B624_0783 | 998331 | 999296 | − | Uncharacterized protein |
| B624_0784 | 999519 | 999623 | − | hypothetical protein |
| B624_0785 | 999683 | 1000615 | − | membrane protein |
| B624_0786 | 1000894 | 1001295 | + | Hypothetical protein |
| B624_0787 | 1001329 | 1002621 | − | SAM-dependent methyltransferases |
| B624_0788 | 1002690 | 1003532 | + | possible phosphoglycerate mutase |
| B624_0789 | 1003650 | 1004597 | + | magnesium transporter, CorA family |
| B624_0790 | 1004615 | 1005538 | + | solute binding protein of ABC transporter system |
| B624_0791 | 1005584 | 1008544 | + | leucyl-tRNA synthetase |
| B624_0792 | 1008708 | 1009484 | + | competence protein ComEA helix-hairpin-helixrepeat region domain protein |
| B624_0793 | 1009484 | 1011235 | + | membrane protein |
| B624_0794 | 1011378 | 1012721 | + | prolidase (X-Pro dipeptidase) or chlorohydrolase |
| B624_0795 | 1012791 | 1013759 | + | DNA polymerase III, delta subunit |
| B624_0796 | 1013783 | 1014346 | + | Hypothetical protein |
| B624_0797 | 1014411 | 1015289 | + | Metal-dependent proteases, molecular chaperone |
| B624_0798 | 1015308 | 1015859 | + | ribosomal-protein-alanine acetyltransferase |
| B624_0799 | 1015859 | 1016899 | + | O-sialoglycoprotein endopeptidase |
| B624_0800 | 1017569 | 1018501 | + | probable integrase/recombinse |

TABLE 1-continued

Open reading frames of the genome of 35624.

| Gene ID | Start | End | Strand | Predicted Function |
|---|---|---|---|---|
| B624_0801 | 1018564 | 1018887 | − | hypothetical protein |
| B624_0802 | 1018909 | 1019862 | − | hypothetical protein |
| B624_0803 | 1019849 | 1020439 | − | hypothetical protein |
| B624_0804 | 1020474 | 1021376 | − | Fic protein family family |
| B624_0805 | 1021357 | 1021929 | − | hypothetical protein |
| B624_0806 | 1021949 | 1023763 | − | hypothetical protein |
| B624_0807 | 1023782 | 1024864 | − | hypothetical protein |
| B624_0808 | 1024893 | 1025600 | − | hypothetical protein |
| B624_0809 | 1025761 | 1026843 | − | TraG-related protein |
| B624_0810 | 1026843 | 1027799 | − | hypothetical protein |
| B624_0811 | 1027799 | 1028257 | − | hypothetical protein |
| B624_0812 | 1028379 | 1028669 | + | hypothetical protein |
| B624_0813 | 1028786 | 1030942 | + | Topoisomerase IA |
| B624_0814 | 1031020 | 1031448 | + | hypothetical protein |
| B624_0815 | 1031753 | 1032193 | + | Bacterial mobilisation protein (MobC) |
| B624_0817 | 1032621 | 1033400 | − | Fic protein family family |
| B624_0818 | 1033518 | 1034822 | + | relaxase/mobilization nuclease family protein |
| B624_0819 | 1034848 | 1036128 | − | hipA transcription regulator protein |
| B624_0820 | 1036128 | 1036439 | − | hypothetical protein |
| B624_0821 | 1036545 | 1037675 | − | hypothetical protein |
| B624_0822 | 1038015 | 1038551 | − | hypothetical protein |
| B624_0823 | 1038618 | 1040423 | − | conjugative transfer gene complex protein |
| B624_0824 | 1040507 | 1041145 | − | hypothetical protein |
| B624_0825 | 1041250 | 1042281 | − | hypothetical protein |
| B624_0826 | 1042389 | 1042865 | − | hypothetical protein |
| B624_0827 | 1043244 | 1044839 | − | ATP binding protein-like protein |
| B624_0828 | 1044857 | 1046341 | − | hypothetical protein |
| B624_0829 | 1046369 | 1048357 | − | hypothetical protein |
| B624_0830 | 1048370 | 1048669 | − | hypothetical protein |
| B624_0831 | 1048710 | 1049189 | − | hypothetical protein |
| B624_0832 | 1049206 | 1050405 | − | hypothetical protein |
| B624_0833 | 1050435 | 1051070 | − | hypothetical protein |
| B624_0834 | 1051396 | 1056213 | − | hypothetical protein |
| B624_0835 | 1056508 | 1057458 | − | hypothetical protein |
| B624_0836 | 1057844 | 1058440 | − | ATPases involved inchromosome partitioning |
| B624_0837 | 1058539 | 1059152 | − | hypothetical protein |
| B624_0838 | 1059167 | 1059448 | − | ATPases involved inchromosome partitioning |
| B624_0839 | 1059569 | 1060042 | − | possible WhiB-like transcription factor |
| B624_0840 | 1060036 | 1061400 | − | hypothetical protein |
| B624_0841 | 1061400 | 1061597 | − | hypothetical protein |
| B624_0842 | 1061748 | 1061894 | − | hypothetical protein |
| B624_0843 | 1061958 | 1062263 | − | hypothetical protein |
| B624_0844 | 1062260 | 1062601 | − | hypothetical protein |
| B624_0845 | 1062779 | 1062997 | − | hypothetical protein |
| B624_0846 | 1063127 | 1063546 | + | hypothetical protein |
| B624_0847 | 1064092 | 1064778 | + | peptidase M23B |
| B624_0848 | 1064862 | 1066490 | − | hypothetical protein |
| B624_0849 | 1066742 | 1067959 | − | isocitrate dehydrogenase, NADP-dependent |
| B624_0850 | 1068087 | 1069208 | + | IMP dehydrogenase family protein |
| B624_0851 | 1069373 | 1069861 | + | hypothetical protein |
| B624_0852 | 1069955 | 1072039 | + | long-chain-fatty-acid--CoA ligase |
| B624_0853 | 1072049 | 1072534 | + | polypeptide deformylase |
| B624_0854 | 1072894 | 1073736 | + | ribosomal protein S2 |
| B624_0855 | 1073818 | 1074666 | + | translation elongation factor Ts |
| B624_0856 | 1074843 | 1075580 | + | uridylate kinase |
| B624_0857 | 1075660 | 1076208 | + | ribosome recycling factor |
| B624_0858 | 1076234 | 1077217 | + | phosphatidate cytidylyltransferase |
| B624_0859 | 1077431 | 1078597 | + | 23S rRNA m(2)A-2503 methyltransferase |
| B624_0860 | 1078604 | 1079149 | − | thiJ |
| B624_0861 | 1079324 | 1080091 | + | Imidazole glycerol phosphate synthase subunit hisF |
| B624_0862 | 1080228 | 1080620 | + | phosphoribosyl-AMP cyclohydrolase |
| B624_0863 | 1080704 | 1082257 | + | anthranilate synthase component I |
| B624_0864 | 1082328 | 1082564 | − | hypothetical protein |
| B624_0865 | 1082576 | 1084174 | + | ATP binding protein of ABC transporter |
| B624_0866 | 1084221 | 1084925 | + | oxidoreductase, short-chainhydrogenase/reductase family |
| B624_0867 | 1084999 | 1085364 | + | protein with unknownfunction |
| B624_0868 | 1085423 | 1086091 | − | hypothetical protein |
| B624_0869 | 1086091 | 1087701 | + | ATP binding protein of ABC transporter |
| B624_0870 | 1087704 | 1088402 | + | cobalt ABC transporter permease |
| B624_0871 | 1088405 | 1089049 | − | Permeases of the major facilitator superfamily |
| B624_0872 | 1089249 | 1090877 | + | hypothetical protein |
| B624_0873 | 1090877 | 1091548 | + | hypothetical protein |
| B624_0874 | 1091548 | 1095093 | + | hypothetical protein |
| B624_0875 | 1095161 | 1096351 | + | hypothetical protein |
| B624_0876 | 1096521 | 1097084 | + | hypothetical protein |

TABLE 1-continued

Open reading frames of the genome of 35624.

| Gene ID | Start | End | Strand | Predicted Function |
|---|---|---|---|---|
| B624_0877 | 1097352 | 1100384 | + | excinuclease ABC, A subunit |
| B624_0878 | 1100532 | 1102895 | + | excinuclease ABC, C subunit |
| B624_0879 | 1103007 | 1103975 | + | aroE |
| B624_0880 | 1103978 | 1104961 | + | P-loop-containing kinase |
| B624_0881 | 1105163 | 1106110 | + | Uncharacterized protein |
| B624_0882 | 1106282 | 1107484 | + | phosphoglycerate kinase |
| B624_0883 | 1107546 | 1108346 | + | triosephosphate isomerase |
| B624_0884 | 1108413 | 1108658 | + | preprotein translocase, SecG subunit |
| B624_0885 | 1108763 | 1109710 | + | L-2-hydroxyisocaproate/malate/lactate dehydrogenase-like protein |
| B624_0886 | 1109710 | 1110558 | + | hypothetical protein |
| B624_0887 | 1110672 | 1112225 | + | aminotransferase, class I |
| B624_0888 | 1112360 | 1113466 | − | hypothetical protein |
| B624_0889 | 1113642 | 1114976 | − | branched-chain amino acid transport system II carrier protein |
| B624_0890 | 1115108 | 1116208 | − | transaldolase |
| B624_0891 | 1116332 | 1118437 | − | transketolase |
| B624_0892 | 1118812 | 1119927 | + | heat-inducible transcription repressor HrcA |
| B624_0893 | 1119986 | 1121128 | + | dnaJ protein |
| B624_0894 | 1121180 | 1121968 | − | fructosamine kinase |
| B624_0895 | 1122113 | 1122994 | + | Undecaprenyl-diphosphatase |
| B624_0896 | 1123157 | 1123987 | − | hypothetical protein |
| B624_0897 | 1124807 | 1126837 | + | threonyl-tRNA synthetase |
| B624_0898 | 1126980 | 1127561 | + | Diadenosine tetraphosphate (Ap4A) hydrolase and other HIT family hydrolase |
| B624_0899 | 1127703 | 1128455 | + | hypothetical protein |
| B624_0900 | 1128464 | 1129045 | + | crossover junction endodeoxyribonuclease RuvC |
| B624_0901 | 1129106 | 1129729 | + | Holliday junction DNA helicase RuvA |
| B624_0902 | 1129732 | 1130793 | + | Holliday junction DNA helicase RuvB |
| B624_0903 | 1130861 | 1131292 | + | preprotein translocase, YajC subunit |
| B624_0904 | 1131359 | 1131937 | + | adenine phosphoribosyltransferase |
| B624_0905 | 1132037 | 1133236 | + | succinyl-CoA synthetase, beta subunit |
| B624_0906 | 1133239 | 1134147 | + | succinyl-CoA synthase, alpha subunit |
| B624_0907 | 1134170 | 1135546 | + | membrane protein |
| B624_0908 | 1135581 | 1137131 | + | purine biosynthesis protein purH (Includes: Phosphoribosylaminoimidazolecarboxamide formyltransferase and IMP cyclohydrolase) |
| B624_0909 | 1137484 | 1138449 | − | Glycerol uptake facilitator and related permeases |
| B624_0910 | 1138645 | 1139412 | + | ribosomal large subunit pseudouridine synthase B |
| B624_0911 | 1139412 | 1141538 | + | cytidylate kinase/GTP-binding protein |
| B624_0912 | 1141896 | 1143422 | + | UDP-glucose pyrophosphorylase |
| B624_0913 | 1143565 | 1145475 | + | Hypothetical protein |
| B624_0914 | 1145489 | 1145803 | + | hypothetical protein |
| B624_0915 | 1145819 | 1148407 | + | Superfamily II RNA helicase |
| B624_0916 | 1148524 | 1148868 | + | hypothetical protein |
| B624_0917 | 1149001 | 1149717 | + | haloacid dehalogenase domain-containing protein hydrolase |
| B624_0918 | 1149744 | 1149995 | + | hypothetical protein |
| B624_0919 | 1150135 | 1150539 | − | hypothetical protein |
| B624_0920 | 1150673 | 1151302 | − | MerR type transcriptional regulator |
| B624_0921 | 1151406 | 1151846 | − | possible signal transduction protein |
| B624_0922 | 1151856 | 1152674 | − | hypothetical protein |
| B624_0923 | 1152693 | 1153022 | − | small basic protein |
| B624_0924 | 1153025 | 1153999 | − | hypothetical protein |
| B624_0925 | 1153992 | 1154606 | − | CDP-diacylglycerol--glycerol-3-phosphate 3-phosphatidyltransferase |
| B624_0926 | 1154623 | 1155471 | − | ATP phosphoribosyltransferase |
| B624_0927 | 1155486 | 1155746 | − | phosphoribosyl-ATP pyrophosphohydrolase |
| B624_0928 | 1155812 | 1156477 | − | ribulose-phosphate 3-epimerase |
| B624_0929 | 1156556 | 1157500 | − | prolipoprotein diacylglyceryl transferase |
| B624_0930 | 1157614 | 1158486 | − | tryptophan synthase, alpha subunit |
| B624_0931 | 1158507 | 1160591 | − | tryptophan synthase, beta subunit |
| B624_0932 | 1161120 | 1161968 | − | nfo |
| B624_0933 | 1163206 | 1164216 | − | hypothetical protein |
| B624_0934 | 1164570 | 1164860 | − | hypothetical protein |
| B624_0935 | 1165260 | 1165715 | − | hypothetical protein |
| B624_0936 | 1165903 | 1166406 | + | acetyltransferase |
| B624_0937 | 1166567 | 1166746 | + | hypothetical protein |
| B624_0938 | 1166793 | 1167323 | + | hypothetical protein |
| B624_0939 | 1167392 | 1167961 | − | acetyltransferase, GNAT family |
| B624_0940 | 1168315 | 1169001 | − | hypothetical protein |
| B624_0941 | 1169017 | 1169823 | − | hypothetical protein |
| B624_0942 | 1169832 | 1170527 | − | ABC transporter related protein |
| B624_0943 | 1170676 | 1171263 | + | Respose regulator |
| B624_0946 | 1172956 | 1173576 | − | hypothetical protein |
| B624_0947 | 1173576 | 1174301 | − | hypothetical protein |

TABLE 1-continued

Open reading frames of the genome of 35624.

| Gene ID | Start | End | Strand | Predicted Function |
|---|---|---|---|---|
| B624_0948 | 1174309 | 1174962 | − | ABC transporter related protein |
| B624_0949 | 1175271 | 1176518 | + | transposase |
| B624_0950 | 1176714 | 1177379 | − | two component transcriptional regulator, LuxR family |
| B624_0951 | 1177379 | 1178596 | − | histidine protein kinase |
| B624_0952 | 1178638 | 1179060 | − | hypothetical protein |
| B624_0953 | 1179039 | 1180061 | − | hypothetical protein |
| B624_0954 | 1180057 | 1180815 | − | macrolide export ATP-binding/permease protein MacB |
| B624_0955 | 1181154 | 1181684 | − | hypothetical protein |
| B624_0956 | 1182016 | 1182315 | + | hypothetical protein |
| B624_0957 | 1182321 | 1182662 | + | hypothetical protein |
| B624_0958 | 1182847 | 1183050 | − | hypothetical protein |
| B624_0962 | 1184840 | 1185853 | − | hypothetical protein |
| B624_0963 | 1186097 | 1186555 | − | hypothetical protein |
| B624_0964 | 1187212 | 1188783 | + | APC family amino acid-polyamine-organocation transporter |
| B624_0965 | 1188993 | 1189640 | − | signal peptidase I-2 |
| B624_0966 | 1189721 | 1190146 | − | hypothetical protein |
| B624_0967 | 1190467 | 1191420 | + | hypothetical protein |
| B624_0968 | 1191479 | 1191801 | + | hypothetical protein |
| B624_0969 | 1192540 | 1193727 | + | Aspartate transaminase |
| B624_0970 | 1193770 | 1195530 | + | YjeF family protein |
| B624_0971 | 1195635 | 1196261 | + | Hydrolase (HAD superfamily) |
| B624_0972 | 1196366 | 1197286 | + | transcriptional regulator, LysR family |
| B624_0973 | 1197447 | 1198565 | − | Hydrolases or acyltransferases (alpha/beta hydrolase superfamily) |
| B624_0974 | 1198783 | 1198932 | − | hypothetical protein |
| B624_0975 | 1199044 | 1199736 | − | orotate phosphoribosyltransferase |
| B624_0976 | 1199748 | 1200716 | − | dihydroorotate dehydrogenase |
| B624_0977 | 1200722 | 1201543 | − | dihydroorotate dehydrogenase, electron transfer subunit |
| B624_0978 | 1201682 | 1202632 | − | orotidine 5'-phosphate decarboxylase |
| B624_0979 | 1202653 | 1204146 | − | dihydroorotase |
| B624_0980 | 1204146 | 1204562 | − | Aspartate carbamoyltransferase regulatory chain |
| B624_0981 | 1204565 | 1205524 | − | aspartate carbamoyltransferase |
| B624_0982 | 1205669 | 1208896 | − | glutamate-ammonia ligase adenylyltransferasefamily |
| B624_0983 | 1208955 | 1209905 | − | Penicillin V acylase and related amidases |
| B624_0984 | 1210042 | 1210893 | − | 5,10-methylenetetrahydrofolate reductase |
| B624_0985 | 1210955 | 1213255 | − | 5-methyltetrahydropteroyltriglutamate--homocysteineS-methyltransferase |
| B624_0986 | 1213369 | 1213923 | − | phosphohistidine phosphatase SixA |
| B624_0987 | 1214024 | 1215091 | − | protein-L-isoaspartate methyltransferase |
| B624_0988 | 1215168 | 1215803 | + | phospholipase/carboxylesterase |
| B624_0989 | 1215850 | 1216806 | − | oxidoreductase, aldo/keto reductase 2 family |
| B624_0990 | 1217063 | 1217995 | + | esterase/lipase |
| B624_0991 | 1218234 | 1219178 | + | Alcohol dehydrogenase, zinc-binding dehydrogenase family |
| B624_0993 | 1220459 | 1221484 | + | transposase |
| B624_0994 | 1221484 | 1221948 | + | hypothetical protein |
| B624_0995 | 1221948 | 1222706 | + | hypothetical protein |
| B624_0996 | 1222896 | 1223972 | + | hypothetical protein |
| B624_0997 | 1224236 | 1224811 | + | hypothetical protein |
| B624_0999 | 1225221 | 1226144 | − | hypothetical protein |
| B624_1000 | 1226238 | 1227140 | − | hypothetical protein |
| B624_1001 | 1227158 | 1228765 | − | hypothetical protein |
| B624_1002 | 1229279 | 1230097 | − | ADP-ribosylglycohydrolase |
| B624_1003 | 1230187 | 1230412 | + | hypothetical protein |
| B624_1005 | 1232085 | 1232906 | + | hypothetical protein |
| B624_1006 | 1233000 | 1233548 | − | alkyl hydroperoxide reductase/Thiol specific antioxidant/Mal allergen |
| B624_1007 | 1233681 | 1234511 | − | carbon-nitrogen hydrolase |
| B624_1008 | 1234511 | 1235365 | − | hydrolase, haloacid dehalogenase-like family |
| B624_1009 | 1235520 | 1236365 | − | modF |
| B624_1010 | 1236462 | 1237709 | − | rfag1 |
| B624_1011 | 1237841 | 1238302 | − | hypothetical protein |
| B624_1012 | 1238382 | 1239917 | − | gltD |
| B624_1013 | 1239922 | 1244490 | − | glutamate synthase, large subunit |
| B624_1014 | 1244835 | 1245116 | + | hypothetical protein |
| B624_1015 | 1245175 | 1246197 | − | dihydrodipicolinate reductase-like protein |
| B624_1016 | 1246656 | 1246979 | + | hypothetical protein |
| B624_1017 | 1247042 | 1247227 | − | hypothetical protein |
| B624_1018 | 1247493 | 1248536 | − | ChaR3 protein |
| B624_1019 | 1249123 | 1250073 | + | hypothetical protein |
| B624_1020 | 1250541 | 1250888 | − | hypothetical protein |
| B624_1021 | 1251177 | 1252538 | + | norm1 |
| B624_1022 | 1252915 | 1254216 | + | integrase |
| B624_1023 | 1254323 | 1255450 | − | glycerate kinase |
| B624_1024 | 1255637 | 1256734 | + | transcriptional regulator, LacI family |

TABLE 1-continued

Open reading frames of the genome of 35624.

| Gene ID | Start | End | Strand | Predicted Function |
|---|---|---|---|---|
| B624_1025 | 1256820 | 1258226 | − | oxygen-independent coproporphyrinogen III oxidase |
| B624_1026 | 1258229 | 1260106 | − | GTP-binding protein LepA |
| B624_1027 | 1260253 | 1260510 | + | Ribosomal protein S20 |
| B624_1028 | 1260768 | 1261556 | − | hypothetical protein |
| B624_1029 | 1261807 | 1262703 | − | MazG family protein |
| B624_1030 | 1262903 | 1264027 | − | branched-chain amino acid aminotransferase |
| B624_1031 | 1264254 | 1264871 | − | ribosomal 5S rRNA E-loop binding proteinCtc/L25/TL5 |
| B624_1032 | 1265298 | 1266332 | + | hypothetical protein |
| B624_1033 | 1266474 | 1267895 | − | NAD(P) transhydrogenase subunit beta |
| B624_1034 | 1267898 | 1268200 | − | NAD/NADP transhydrogenase alpha subunit-like protein |
| B624_1035 | 1268219 | 1269379 | − | NAD(P) transhydrogenase subunit alpha part 1 |
| B624_1036 | 1269798 | 1271828 | + | long-chain-fatty-acid--CoA ligase |
| B624_1037 | 1271887 | 1272948 | − | GTP-binding protein Era |
| B624_1038 | 1272953 | 1274383 | − | CBS domain protein |
| B624_1039 | 1274462 | 1275007 | − | metal-dependent hydrolase |
| B624_1040 | 1275000 | 1276172 | − | PhoH family protein |
| B624_1041 | 1276194 | 1276529 | − | Hit family protein |
| B624_1042 | 1276581 | 1277375 | − | Uncharacterized protein in bacteria |
| B624_1043 | 1277619 | 1278494 | + | rRNA methylases |
| B624_1044 | 1278698 | 1279939 | + | glucose-1-phosphate adenylyltransferase |
| B624_1045 | 1280035 | 1280625 | − | mrp protein |
| B624_1046 | 1280635 | 1281186 | − | SUF system FeS assembly protein, NifU family |
| B624_1047 | 1281201 | 1282472 | − | aminotransferase, class-V |
| B624_1048 | 1282614 | 1283390 | − | FeS assembly ATPase SufC |
| B624_1049 | 1283419 | 1284651 | − | FeS assembly protein SufD |
| B624_1050 | 1284660 | 1286156 | − | FeS assembly protein SufB |
| B624_1051 | 1286383 | 1287975 | − | hypothetical protein |
| B624_1052 | 1288225 | 1289883 | − | CTP synthase |
| B624_1053 | 1290032 | 1291585 | − | dipeptidase |
| B624_1054 | 1291684 | 1292127 | − | 3-dehydroquinate dehydratase, type II |
| B624_1055 | 1292294 | 1293913 | − | shikimate kinase/3-dehydroquinate synthase |
| B624_1056 | 1293999 | 1295183 | − | chorismate synthase |
| B624_1057 | 1295247 | 1295717 | + | TadV, prepilin type IV peptidase |
| B624_1058 | 1295891 | 1297069 | − | Periplasmic solute-binding protein |
| B624_1059 | 1297083 | 1297538 | − | YqgF family crossover junction endodeoxyribonuclease, YrrK |
| B624_1060 | 1297550 | 1300228 | − | alanyl-tRNA synthetase |
| B624_1061 | 1300359 | 1300592 | − | hypothetical protein |
| B624_1062 | 1300595 | 1300990 | − | Hypothetical protein |
| B624_1063 | 1301196 | 1301867 | − | phosphoglycerate mutase |
| B624_1064 | 1302020 | 1304008 | + | Acyltransferase family domain protein |
| B624_1065 | 1304105 | 1304728 | − | Ribosomal protein S4 and related proteins |
| B624_1066 | 1304930 | 1305895 | − | ABC transporter, ATP-binding protein |
| B624_1067 | 1305900 | 1307114 | − | ABC superfamily ATP binding cassette transporter, membrane protein |
| B624_1068 | 1307208 | 1307603 | − | hypothetical protein |
| B624_1069 | 1307751 | 1310480 | − | hypothetical protein |
| B624_1070 | 1310567 | 1311145 | + | xanthine phosphoribosyltransferase |
| B624_1071 | 1311199 | 1312560 | + | xanthine/uracil permease family protein |
| B624_1072 | 1312696 | 1312902 | − | transcription regulator |
| B624_1073 | 1312912 | 1313169 | − | hypothetical protein |
| B624_1074 | 1313326 | 1314144 | − | hydrolase, alpha/beta fold family |
| B624_1075 | 1314432 | 1315367 | + | hypothetical protein |
| B624_1076 | 1315462 | 1315860 | − | glyoxalase family protein |
| B624_1077 | 1316019 | 1316630 | + | Pyrazinamidase/nicotinamidase |
| B624_1078 | 1316885 | 1318360 | + | Transcriptional regulator containing an HTH domain and an uncharacterized domain shared with the mammalian protein Schlafen |
| B624_1079 | 1318371 | 1319780 | − | ABC-type multidrug transport system permease component |
| B624_1080 | 1319770 | 1321005 | − | ABC-type multidrug transport system permease component |
| B624_1081 | 1321109 | 1322089 | − | ABC-type multidrug transport system, ATPase component |
| B624_1082 | 1322475 | 1323824 | + | Signal transduction histidine kinase |
| B624_1083 | 1323827 | 1324477 | + | response regulator of two-component system |
| B624_1084 | 1324667 | 1325287 | − | Phosphate transport regulator |
| B624_1085 | 1325308 | 1326357 | − | phosphate transporter family protein |
| B624_1086 | 1326480 | 1326674 | − | Uncharacterized small protein |
| B624_1087 | 1326735 | 1329131 | − | carbon starvation protein A |
| B624_1088 | 1329376 | 1330668 | + | alpha amylase |
| B624_1089 | 1330703 | 1331314 | − | hypothetical protein |
| B624_1090 | 1331486 | 1333669 | − | possible ATP-dependent RNA helicase |
| B624_1091 | 1334052 | 1335338 | − | uracil-xanthine permease |
| B624_1092 | 1335446 | 1336273 | − | Fructose-2,6-bisphosphatase |
| B624_1093 | 1336327 | 1336905 | − | hypothetical protein |
| B624_1094 | 1337061 | 1337612 | + | transcriptional regulator |

TABLE 1-continued

Open reading frames of the genome of 35624.

| Gene ID | Start | End | Strand | Predicted Function |
|---|---|---|---|---|
| B624_1095 | 1337738 | 1338898 | − | virion core protein |
| B624_1096 | 1339275 | 1340816 | − | hypothetical protein |
| B624_1097 | 1341250 | 1341687 | + | hypothetical protein |
| B624_1098 | 1341752 | 1343449 | + | serine/threonine protein kinase |
| B624_1099 | 1343493 | 1344980 | − | efflux transporter protein |
| B624_1100 | 1345295 | 1347343 | − | hypothetical protein |
| B624_1101 | 1347576 | 1347758 | − | hypothetical protein |
| B624_1102 | 1347947 | 1348309 | + | hypothetical protein |
| B624_1103 | 1348405 | 1349910 | − | hypothetical protein |
| B624_1104 | 1349906 | 1351072 | − | hypothetical protein |
| B624_1105 | 1351310 | 1351477 | + | hypothetical protein |
| B624_1106 | 1351660 | 1352478 | + | phosphoesterase or phosphohydrolase |
| B624_1107 | 1352565 | 1354004 | + | hypothetical protein |
| B624_1108 | 1354223 | 1354612 | + | hypothetical protein |
| B624_1109 | 1354729 | 1355193 | + | hypothetical protein |
| B624_1110 | 1355496 | 1356380 | − | hypothetical protein |
| B624_1111 | 1356380 | 1357450 | − | Site-specific recombinase XerD |
| B624_1112 | 1357650 | 1358675 | + | transposase |
| B624_1113 | 1358675 | 1359139 | + | hypothetical protein |
| B624_1114 | 1359139 | 1359897 | + | hypothetical protein |
| B624_1115 | 1360305 | 1361396 | − | GTP-binding protein YchF |
| B624_1116 | 1361533 | 1362351 | − | pyrroline-5-carboxylate reductase |
| B624_1117 | 1362416 | 1363891 | − | proline iminopeptidase |
| B624_1118 | 1363977 | 1366433 | + | histidine kinase sensor of two-component system |
| B624_1119 | 1366458 | 1367345 | + | response regulator |
| B624_1120 | 1367384 | 1370233 | − | transport protein |
| B624_1121 | 1370265 | 1371176 | − | ABC-type antimicrobial peptide transport system, ATPase component |
| B624_1122 | 1371528 | 1372841 | − | O-acetylhomoserine sulfhydrylase |
| B624_1123 | 1373315 | 1374184 | + | pyridoxal kinase |
| B624_1124 | 1374553 | 1374924 | + | endonuclease |
| B624_1125 | 1374983 | 1376515 | + | Mg chelatase-related protein |
| B624_1126 | 1376515 | 1378212 | + | DNA processing protein DprA |
| B624_1127 | 1378272 | 1380134 | + | sdhA |
| B624_1128 | 1380233 | 1381195 | + | Succinate dehydrogenase iron-sulfur protein |
| B624_1129 | 1381292 | 1381954 | + | O-methyltransferase |
| B624_1130 | 1382006 | 1382944 | − | Rossmann fold nucleotide-binding protein |
| B624_1131 | 1383180 | 1384595 | − | clpx |
| B624_1132 | 1385070 | 1386485 | − | ATP-dependent Clp protease, ATP-binding subunitClpX |
| B624_1133 | 1386610 | 1387308 | − | ATP-dependent Clp protease, proteolytic subunit 2 |
| B624_1134 | 1387317 | 1387937 | − | ATP-dependent Clp protease, proteolytic subunit 1 |
| B624_1135 | 1388046 | 1388423 | − | hypothetical protein |
| B624_1136 | 1388538 | 1390001 | − | voltage-gated chloride channel family protein |
| B624_1137 | 1390189 | 1391565 | − | trigger factor |
| B624_1138 | 1391623 | 1392921 | − | 3-5 exonuclease domain protein |
| B624_1139 | 1392921 | 1393556 | − | Permeases of the majorfacilitator superfamily |
| B624_1140 | 1393622 | 1394500 | − | pyruvate formate-lyase 1 activating enzyme |
| B624_1141 | 1394613 | 1396985 | − | formate acetyltransferase |
| B624_1142 | 1397254 | 1397520 | − | hypothetical protein |
| B624_1143 | 1397531 | 1399225 | − | NH(3)-dependent NAD synthetase |
| B624_1144 | 1399577 | 1400725 | − | Peptidase, M20/M25/M40 family |
| B624_1145 | 1400817 | 1401500 | − | permease protein of ABC transporter system |
| B624_1146 | 1401500 | 1402702 | − | ABC transporter, ATP-binding protein |
| B624_1147 | 1402839 | 1403816 | − | ABC-type transport system protein |
| B624_1148 | 1404020 | 1404847 | + | hydrolase, haloacid dehalogenase-like family |
| B624_1149 | 1404975 | 1407449 | − | D-xylulose 5-phosphate/D-fructose 6-phosphatephosphoketolase |
| B624_1150 | 1407895 | 1409454 | + | GMP synthase |
| B624_1151 | 1409930 | 1410304 | + | arsb1 |
| B624_1152 | 1410328 | 1410720 | + | arsenical resistance protein/arsenate reductase |
| B624_1154 | 1412111 | 1413136 | + | transposase |
| B624_1155 | 1413136 | 1413600 | + | possible Transposase |
| B624_1156 | 1413600 | 1414358 | + | hypothetical protein |
| B624_1159 | 1416510 | 1417160 | + | hypothetical protein |
| B624_1160 | 1417164 | 1418444 | + | hypothetical protein |
| B624_1161 | 1418440 | 1418820 | + | hypothetical protein |
| B624_1162 | 1419070 | 1420548 | + | ATP-dependent Zn protease |
| B624_1163 | 1420727 | 1422598 | + | lipopolysaccharide modification acyltransferase |
| B624_1164 | 1422690 | 1423706 | + | prsA |
| B624_1165 | 1423991 | 1425370 | + | nucleotidyl transferase |
| B624_1166 | 1425377 | 1425787 | + | iojap-related protein |
| B624_1167 | 1425942 | 1426637 | + | phosphoglycerate mutase |
| B624_1168 | 1427294 | 1428961 | + | phosphate acetyltransferase |
| B624_1169 | 1429099 | 1429695 | + | acetate kinase |
| B624_1170 | 1429718 | 1430326 | + | Acetate kinase |
| B624_1171 | 1430503 | 1431837 | − | 3-phosphoshikimate 1-carboxyvinyltransferase |

TABLE 1-continued

Open reading frames of the genome of 35624.

| Gene ID | Start | End | Strand | Predicted Function |
|---|---|---|---|---|
| B624_1172 | 1431867 | 1433036 | − | membrane protein |
| B624_1173 | 1433357 | 1433766 | + | hypothetical protein |
| B624_1175 | 1434688 | 1436172 | − | galactoside symporter |
| B624_1176 | 1436515 | 1439583 | + | beta-galactosidase |
| B624_1178 | 1441301 | 1442047 | − | hypothetical protein |
| B624_1179 | 1442167 | 1442559 | − | hypothetical protein |
| B624_1180 | 1442574 | 1442990 | − | hypothetical protein |
| B624_1183 | 1445667 | 1445948 | + | hypothetical protein |
| B624_1184 | 1446119 | 1446796 | + | hypothetical protein |
| B624_1185 | 1447254 | 1448801 | + | DNA-cytosine methyltransferase |
| B624_1189 | 1452909 | 1453127 | + | IS861, transposase OrfB |
| B624_1191 | 1453837 | 1455122 | − | hypothetical protein |
| B624_1192 | 1455179 | 1455604 | − | cell division protein FtsZ |
| B624_1193 | 1455752 | 1459864 | − | DNA helicase/exodeoxyribonuclease V, subunit A |
| B624_1194 | 1459861 | 1463163 | − | ATP-dependent nuclease, subunit B |
| B624_1195 | 1463295 | 1465928 | − | DNA polymerase III, alpha subunit |
| B624_1196 | 1466012 | 1467055 | + | hypothetical protein |
| B624_1197 | 1467089 | 1467952 | − | ribonuclease BN |
| B624_1199 | 1468949 | 1469908 | − | pseudouridylate synthase |
| B624_1200 | 1469911 | 1470456 | − | lipoprotein signal peptidase |
| B624_1201 | 1470481 | 1471857 | − | hypothetical protein |
| B624_1202 | 1472000 | 1472299 | − | integral membrane protein |
| B624_1203 | 1472424 | 1472900 | − | hypothetical protein |
| B624_1204 | 1472916 | 1474124 | − | Tubulin/FtsZ family, C-terminal domain |
| B624_1205 | 1474239 | 1475480 | − | tRNA-dihydrouridine synthase |
| B624_1206 | 1475628 | 1477097 | − | glycyl-tRNA synthetase |
| B624_1207 | 1477533 | 1478474 | + | hydroxyethylthiazole kinase |
| B624_1208 | 1478560 | 1481310 | + | thiamine biosynthesis protein ThiE/ThiC |
| B624_1209 | 1481353 | 1481679 | − | hypothetical protein |
| B624_1210 | 1481820 | 1482626 | + | phosphomethylpyrimidine kinase |
| B624_1211 | 1482680 | 1483054 | + | Uncharacterized protein |
| B624_1212 | 1483563 | 1484939 | + | permease protein |
| B624_1213 | 1485207 | 1485515 | + | hypothetical protein |
| B624_1214 | 1485571 | 1485978 | + | hypothetical protein |
| B624_1215 | 1486039 | 1487433 | + | Serpin (serine protease inhibitor) superfamily |
| B624_1216 | 1487480 | 1488517 | + | transcriptional regulator, LacI family |
| B624_1217 | 1488734 | 1490068 | + | oligosaccharide:H+ symporter |
| B624_1218 | 1490082 | 1491635 | + | sucrose-6-phosphate hydrolase |
| B624_1219 | 1491833 | 1492612 | + | ABC transporter, permease protein, cysTW family |
| B624_1220 | 1492876 | 1493943 | + | pyrimidine precursor biosynthesis enzyme |
| B624_1221 | 1494070 | 1495254 | + | inosine-uridine preferring nucleoside hydrolase |
| B624_1222 | 1495416 | 1496201 | − | undecaprenyl diphosphate synthase |
| B624_1223 | 1496207 | 1496923 | − | DNA repair protein RecO |
| B624_1224 | 1496975 | 1498684 | − | Hydrolases of the alpha/beta superfamily |
| B624_1225 | 1498808 | 1500025 | − | 1-hydroxy-2-methyl-2-(E)-butenyl 4-diphosphatesynthase |
| B624_1226 | 1500028 | 1501215 | − | 1-deoxy-D-xylulose 5-phosphate reductoisomerase |
| B624_1227 | 1501215 | 1502915 | − | Pyridoxine biosynthesis enzyme |
| B624_1228 | 1503387 | 1503800 | − | hypothetical protein |
| B624_1229 | 1503919 | 1504797 | − | PDZ domain family protein |
| B624_1230 | 1505018 | 1506760 | + | hypothetical protein |
| B624_1231 | 1506836 | 1508407 | − | ATP-dependent DNA helicase PcrA |
| B624_1232 | 1508553 | 1510205 | + | aminoglycoside phosphotransferase |
| B624_1233 | 1510357 | 1510578 | + | ATP-binding protein |
| B624_1234 | 1510645 | 1511535 | − | PHP domain N-terminal region family |
| B624_1235 | 1511673 | 1512407 | + | membrane protein |
| B624_1236 | 1512419 | 1513309 | − | diaminopimelate epimerase |
| B624_1237 | 1513417 | 1514208 | + | glutamate racemase |
| B624_1238 | 1514340 | 1515182 | + | esterase-like protein |
| B624_1239 | 1515255 | 1516151 | − | Membrane protease subunits, stomatin/prohibitin |
| B624_1242 | 1517316 | 1517573 | + | transcriptional regulator |
| B624_1243 | 1517692 | 1517940 | − | Glutaredoxin and related proteins |
| B624_1244 | 1518187 | 1519422 | − | cystathionine beta-lyase |
| B624_1245 | 1519661 | 1520560 | − | glutamine ABC transporter, periplasmicglutamine-binding protein (glnH) |
| B624_1246 | 1520629 | 1521417 | − | amino acid ABC transporter, ATP-binding protein |
| B624_1247 | 1521413 | 1522084 | − | amino acid ABC transporter, permease protein |
| B624_1248 | 1522074 | 1522730 | − | amino acid ABC transporter, permease protein |
| B624_1249 | 1522958 | 1523605 | + | Phospholipase/Carboxylesterase |
| B624_1250 | 1523620 | 1525872 | − | Translation elongation factor |
| B624_1251 | 1526019 | 1526723 | + | DNA polymerase III alpha subunit |
| B624_1252 | 1526731 | 1527318 | − | guanylate kinase |
| B624_1253 | 1527501 | 1528418 | − | orotidine 5'-phosphate decarboxylase |
| B624_1254 | 1528421 | 1531801 | − | carbamoyl-phosphate synthase, large subunit |
| B624_1255 | 1531806 | 1533029 | − | carbamoyl-phosphate synthase, small subunit |
| B624_1256 | 1533219 | 1533788 | − | transcription antitermination factor NusB |
| B624_1257 | 1533846 | 1534409 | − | Elongation factor P (EF-P) |

TABLE 1-continued

Open reading frames of the genome of 35624.

| Gene ID | Start | End | Strand | Predicted Function |
|---|---|---|---|---|
| B624_1258 | 1534514 | 1535248 | + | ATP-binding protein of ABC transporter system |
| B624_1259 | 1535248 | 1536033 | + | ABC type permease |
| B624_1260 | 1536066 | 1536770 | − | ErfK/YbiS/YcfS/YnhG family protein |
| B624_1261 | 1536878 | 1539331 | − | hypothetical protein |
| B624_1262 | 1539444 | 1540754 | − | hypothetical protein |
| B624_1263 | 1541413 | 1543257 | + | glycosyltransferase |
| B624_1264 | 1543710 | 1544741 | − | 3-hydroxybutyryl-CoA dehydrogenase |
| B624_1265 | 1544959 | 1546782 | − | alpha-glucosidase |
| B624_1267 | 1547359 | 1549491 | − | 20 family glycoside hydrolase |
| B624_1268 | 1549605 | 1550417 | − | ABC transporter, permease protein, MalFG family |
| B624_1270 | 1551035 | 1551862 | + | hypothetical protein |
| B624_1271 | 1552142 | 1553254 | − | mrp |
| B624_1272 | 1553434 | 1556193 | − | DNA ligase, NAD-dependent |
| B624_1273 | 1556261 | 1559881 | − | hypothetical protein |
| B624_1274 | 1559979 | 1562237 | + | pmt family glycosyltransferase |
| B624_1275 | 1562375 | 1564141 | + | hypothetical protein |
| B624_1276 | 1564204 | 1564986 | − | ABC transporter, ATP-binding protein |
| B624_1277 | 1565037 | 1566299 | − | aminotransferase, class I |
| B624_1278 | 1566573 | 1567337 | − | ROK family protein |
| B624_1279 | 1567559 | 1568365 | + | Nitroreductase family protein |
| B624_1280 | 1568413 | 1569423 | − | glycosyltransferase |
| B624_1281 | 1569675 | 1570325 | + | hypothetical protein |
| B624_1282 | 1570459 | 1572888 | + | ABC transporter, ATP-binding protein |
| B624_1283 | 1572963 | 1573265 | + | RNA-binding protein |
| B624_1284 | 1573370 | 1573732 | − | hypothetical protein |
| B624_1285 | 1573842 | 1574456 | + | hypothetical protein |
| B624_1286 | 1574885 | 1575301 | + | hypothetical protein |
| B624_1287 | 1575432 | 1576415 | − | D-isomer specific 2-hydroxyacid dehydrogenase family protein |
| B624_1288 | 1576714 | 1578168 | + | drug resistance transporter, EmrB/QacA family |
| B624_1289 | 1578399 | 1579418 | − | sugar ABC transporter permease |
| B624_1290 | 1579418 | 1580485 | − | ribose ABC transporter, permease protein |
| B624_1291 | 1580490 | 1582028 | − | ATP binding protein of ABC transporter |
| B624_1292 | 1582172 | 1583152 | − | ribose ABC transporter, periplasmicD-ribose-binding protein |
| B624_1293 | 1583472 | 1585199 | − | Lipoprotein lpqB |
| B624_1294 | 1585199 | 1586893 | − | sensor histidine kinase MtrB |
| B624_1295 | 1586893 | 1587612 | − | hypothetical protein |
| B624_1296 | 1587674 | 1589050 | − | recombination factor protein RarA |
| B624_1297 | 1589136 | 1591700 | − | DEAD box family helicase |
| B624_1298 | 1591837 | 1592907 | − | hypothetical protein |
| B624_1299 | 1592976 | 1593215 | − | hypothetical protein |
| B624_1300 | 1593208 | 1593801 | − | 5'-nucleotidase/2',3'-cyclic phosphodiesterase and relatedesterases |
| B624_1301 | 1593841 | 1595379 | − | hypothetical protein |
| B624_1302 | 1595471 | 1596568 | − | glutamine ABC transporter, glutamine-bindingprotein/permease protein |
| B624_1303 | 1596577 | 1597251 | − | glutamine ABC transporter, permease protein |
| B624_1304 | 1597254 | 1598090 | − | amino acid ABC transporter, amino acid-bindingprotein |
| B624_1305 | 1598125 | 1598964 | − | amino acid ABC transporter, ATP-binding protein |
| B624_1306 | 1599518 | 1600468 | + | hypothetical protein |
| B624_1307 | 1600932 | 1602728 | − | aspartyl-tRNA synthetase |
| B624_1308 | 1602767 | 1604164 | − | histidyl-tRNA synthetase |
| B624_1309 | 1604264 | 1605721 | + | hypothetical protein |
| B624_1310 | 1605933 | 1607723 | − | 5'-nucleotidase family protein |
| B624_1311 | 1607898 | 1608653 | − | Amidase-like protein |
| B624_1312 | 1608742 | 1610115 | − | proline/betaine transporter |
| B624_1313 | 1610308 | 1611807 | − | Purine catabolism regulatory protein-like family |
| B624_1314 | 1611950 | 1613266 | + | cytosine deaminase-like protein |
| B624_1315 | 1613452 | 1616058 | − | ATP-dependent Clp protease, ATP-binding subunitClpC |
| B624_1316 | 1616208 | 1617170 | + | Universal stress protein UspA and related nucleotide-binding proteins |
| B624_1317 | 1617288 | 1618472 | − | hypothetical protein |
| B624_1318 | 1618484 | 1618870 | − | cspB |
| B624_1319 | 1618943 | 1620790 | − | baes1 |
| B624_1320 | 1620965 | 1621693 | − | winged helix family two component transcriptional regulator |
| B624_1321 | 1621689 | 1622492 | − | hypothetical protein |
| B624_1322 | 1622567 | 1622854 | + | hypothetical protein |
| B624_1323 | 1622957 | 1624579 | − | chaperone |
| B624_1324 | 1624820 | 1625056 | − | cold-shock domain family protein |
| B624_1325 | 1625289 | 1625969 | − | hypothetical protein |
| B624_1326 | 1626085 | 1626771 | + | uracil-DNA glycosylase |
| B624_1327 | 1626814 | 1627890 | + | ATPase, MoxR family |
| B624_1328 | 1627890 | 1628837 | + | Protein of unknown function family |
| B624_1329 | 1628840 | 1629388 | + | hypothetical protein |

TABLE 1-continued

Open reading frames of the genome of 35624.

| Gene ID | Start | End | Strand | Predicted Function |
|---|---|---|---|---|
| B624_1330 | 1629388 | 1630443 | + | Uncharacterized protein containing a von Willebrand factor type A (vWA) domain |
| B624_1331 | 1630443 | 1631471 | + | hypothetical protein |
| B624_1332 | 1631471 | 1632070 | + | cell surface elastin binding protein EbpS |
| B624_1333 | 1632316 | 1632660 | + | hypothetical protein |
| B624_1334 | 1632660 | 1634261 | + | hypothetical protein |
| B624_1335 | 1634531 | 1634893 | + | hypothetical protein |
| B624_1336 | 1635034 | 1635672 | − | hypothetical protein |
| B624_1337 | 1635805 | 1637238 | + | adenylosuccinate lyase |
| B624_1338 | 1637373 | 1639931 | + | hypothetical protein |
| B624_1339 | 1640080 | 1640358 | + | DNA-binding protein HU |
| B624_1340 | 1640480 | 1641937 | − | Pup-ligase protein |
| B624_1341 | 1641940 | 1642203 | − | hypothetical protein |
| B624_1342 | 1642234 | 1643133 | − | possible inositol monophosphatase |
| B624_1343 | 1643139 | 1644803 | − | Proteasome component |
| B624_1344 | 1644828 | 1646390 | − | rpt1 |
| B624_1345 | 1646454 | 1647170 | − | hypothetical protein |
| B624_1346 | 1647200 | 1647919 | + | phosphoserine phosphatase SerB |
| B624_1347 | 1647962 | 1650271 | + | primosomal protein N |
| B624_1348 | 1650333 | 1651034 | + | alpha beta hydrolase |
| B624_1349 | 1651061 | 1652044 | + | methionyl-tRNA formyltransferase |
| B624_1350 | 1652142 | 1653992 | − | dihydroxy-acid dehydratase |
| B624_1351 | 1654203 | 1654484 | + | DNA-directed RNA polymerase, omega subunit |
| B624_1352 | 1654765 | 1655982 | + | S-adenosylmethionine synthetase |
| B624_1353 | 1667321 | 1667608 | − | CRISPR-associated protein Cas2 |
| B624_1354 | 1667697 | 1668725 | − | CRISPR-associated protein Cas1 |
| B624_1355 | 1668725 | 1669423 | − | CRISPR-associated protein Cas4 |
| B624_1356 | 1669465 | 1670313 | − | CRISPR-associated protein, Csh2 family protein |
| B624_1357 | 1670320 | 1672275 | − | CRISPR-associated RAMP Csd1 family protein |
| B624_1358 | 1672281 | 1672982 | − | CRISPR-associated protein, CT1134 family |
| B624_1359 | 1672992 | 1675427 | − | CRISPR-associated helicase Cas3 |
| B624_1361 | 1677053 | 1680361 | − | isoleucyl-tRNA synthetase |
| B624_1362 | 1680955 | 1682163 | + | maly2 |
| B624_1363 | 1682280 | 1683785 | − | melb1 |
| B624_1364 | 1684111 | 1687299 | + | lacz1 |
| B624_1365 | 1687365 | 1688372 | − | lacr-type transcription regulator |
| B624_1366 | 1688522 | 1689964 | − | major facilitator superfamily mfs_1 |
| B624_1367 | 1690007 | 1690906 | − | Ribokinase |
| B624_1368 | 1690909 | 1692111 | − | alcohol dehydrogenase, iron-containing |
| B624_1369 | 1692111 | 1692794 | − | Phosphoglycolate phosphatase |
| B624_1370 | 1692921 | 1693901 | − | inosine-uridine preferring nucleoside hydrolase |
| B624_1371 | 1693960 | 1694913 | − | Fructokinase |
| B624_1372 | 1694909 | 1695553 | − | N-(5'phosphoribosyl)anthranilateisomerase |
| B624_1373 | 1695603 | 1696415 | − | ABC transporter, ATP-binding protein |
| B624_1374 | 1696415 | 1697242 | − | hypothetical protein |
| B624_1375 | 1697246 | 1698055 | − | Cobalt transport protein |
| B624_1376 | 1698062 | 1698712 | − | hypothetical protein |
| B624_1377 | 1698969 | 1700846 | + | hypothetical protein |
| B624_1378 | 1700977 | 1702989 | − | ABC transporter, ATP-binding/permease protein |
| B624_1379 | 1702989 | 1704944 | − | ABC transporter, ATP-binding protein |
| B624_1380 | 1704944 | 1705474 | − | transcriptional regulator, MarR family |
| B624_1382 | 1707015 | 1708349 | − | bglc |
| B624_1383 | 1708509 | 1710902 | − | bglx2 |
| B624_1385 | 1711383 | 1712657 | − | glutamate--cysteine ligase |
| B624_1386 | 1713223 | 1718037 | + | domain protein |
| B624_1387 | 1718044 | 1718883 | + | hypothetical protein |
| B624_1388 | 1719052 | 1724187 | − | Activator of 2-hydroxyglutaryl-CoA dehydratase |
| B624_1389 | 1724418 | 1725143 | − | anaerobic ribonucleoside-triphosphate reductaseactivating protein |
| B624_1390 | 1725294 | 1727699 | − | anaerobic ribonucleoside-triphosphate reductase |
| B624_1391 | 1728167 | 1729534 | + | exodeoxyribonuclease VII, large subunit |
| B624_1392 | 1729587 | 1729886 | + | exodeoxyribonuclease VII, small subunit |
| B624_1393 | 1730013 | 1730534 | + | NADP(H) oxidoreductase |
| B624_1394 | 1730676 | 1732538 | − | long-chain-fatty-acid--CoA ligase |
| B624_1395 | 1732765 | 1733166 | − | Large-conductance mechanosensitivechannel, MscL |
| B624_1396 | 1733337 | 1733762 | − | Nucleoside deoxyribosyltransferase |
| B624_1397 | 1733887 | 1734102 | − | Histone acetyltransferaseHPA2 and related acetyltransferases |
| B624_1398 | 1734587 | 1735696 | + | hypothetical protein |
| B624_1399 | 1735718 | 1736683 | − | exopolyphosphatase |
| B624_1400 | 1736864 | 1738084 | − | probable aspartate aminotransferase |
| B624_1401 | 1738178 | 1739230 | + | oxidoreductase, Gfo/Idh/MocA family |
| B624_1402 | 1739267 | 1739779 | − | patch repair protein |
| B624_1403 | 1739862 | 1740377 | + | acetyltransferase, GNAT family |
| B624_1404 | 1740356 | 1740841 | − | hypothetical protein |
| B624_1405 | 1741026 | 1745207 | − | helicase, Snf2 family |

TABLE 1-continued

Open reading frames of the genome of 35624.

| Gene ID | Start | End | Strand | Predicted Function |
|---|---|---|---|---|
| B624_1406 | 1745285 | 1746367 | + | DeoR-type transcriptional regulator |
| B624_1407 | 1746604 | 1747620 | + | tetrahydrodipicolinate N-succinyltransferase(dapD) |
| B624_1408 | 1747840 | 1749129 | − | citrate synthase I |
| B624_1409 | 1749406 | 1750185 | − | methionine aminopeptidase, type I |
| B624_1410 | 1750378 | 1751355 | − | membrane protein |
| B624_1411 | 1751532 | 1753703 | + | Peptidase M13, neprilysin |
| B624_1412 | 1753792 | 1754526 | − | single-stranded DNA-binding protein (ssb)subfamily |
| B624_1413 | 1754805 | 1756646 | − | prolyl-tRNA synthetase |
| B624_1415 | 1757392 | 1758561 | − | pflA |
| B624_1416 | 1758551 | 1760338 | − | Protein of unknown function family |
| B624_1417 | 1760391 | 1761806 | − | TPR domain protein |
| B624_1418 | 1761858 | 1762505 | − | oligoribonuclease |
| B624_1419 | 1762676 | 1764226 | − | inosine-5'-monophosphate dehydrogenase |
| B624_1420 | 1764282 | 1765562 | − | Phospho-N-acetylmuramoyl-pentapeptide-transferase |
| B624_1421 | 1765562 | 1766233 | − | Sua5/YciO/YrdC/YwlC family protein |
| B624_1422 | 1766408 | 1767082 | + | Acetyltransferase |
| B624_1423 | 1767220 | 1767921 | − | branched-chain amino acid ABC transporter, ATP-binding protein |
| B624_1424 | 1767924 | 1768781 | − | branched chain amino acid ABC transporter, ATP-binding protein |
| B624_1425 | 1768781 | 1769866 | − | branched-chain amino acid ABC transporter, permease protein |
| B624_1426 | 1769874 | 1770797 | − | branched-chain amino acid ABC transporter, permease protein |
| B624_1427 | 1771042 | 1772226 | − | branched-chain amino acid ABC transporter, aminoacid-binding protein |
| B624_1428 | 1772502 | 1773407 | − | HemK family modification methylase |
| B624_1429 | 1773473 | 1774558 | − | peptide chain release factor 1 |
| B624_1430 | 1774715 | 1774924 | − | ribosomal protein L31 |
| B624_1431 | 1775256 | 1776482 | − | transcription regulator ROK family |
| B624_1432 | 1776702 | 1778219 | + | xylulokinase |
| B624_1433 | 1778416 | 1778760 | + | hypothetical protein |
| B624_1434 | 1778773 | 1779114 | + | hypothetical protein |
| B624_1436 | 1779656 | 1780930 | − | transposase, Mutator family |
| B624_1437 | 1781199 | 1782545 | − | xylose isomerase |
| B624_1440 | 1783425 | 1784222 | − | hypothetical protein |
| B624_1441 | 1785149 | 1785565 | − | polypeptide deformylase |
| B624_1442 | 1785576 | 1786421 | − | 2,5-diketo-D-gluconic acid reductase |
| B624_1444 | 1787291 | 1787791 | − | MarR-type transcriptional regulator |
| B624_1445 | 1787998 | 1788333 | − | hypothetical protein |
| B624_1446 | 1788358 | 1789572 | − | ABC-type xylose transport system, permease component |
| B624_1447 | 1789575 | 1791125 | − | ABC-type xylose transport system ATPase component |
| B624_1448 | 1791229 | 1792383 | − | ABC-type xylose transport system periplasmic component |
| B624_1449 | 1792635 | 1793801 | + | ROK family protein |
| B624_1450 | 1793842 | 1794705 | + | sugar ABC transporter, ATP-binding protein |
| B624_1451 | 1794736 | 1795683 | − | glucokinase |
| B624_1452 | 1796516 | 1798192 | + | ATP binding protein of ABC transporter |
| B624_1453 | 1798507 | 1799409 | + | acyl-CoA thioesterase II |
| B624_1454 | 1799511 | 1800035 | − | hypothetical protein |
| B624_1455 | 1800213 | 1801622 | − | dihydroneopterin aldolase |
| B624_1456 | 1801736 | 1802608 | − | dihydropteroate synthase |
| B624_1457 | 1802699 | 1803295 | − | GTP cyclohydrolase I |
| B624_1458 | 1803391 | 1805478 | − | cell division protein FtsH |
| B624_1459 | 1805478 | 1806038 | − | hypoxanthine phosphoribosyltransferase |
| B624_1460 | 1806028 | 1807191 | − | ATPase |
| B624_1461 | 1807285 | 1808772 | − | D-alanyl-D-alanine carboxypeptidase/D-alanyl-D-alanine-endopeptidase |
| B624_1462 | 1808798 | 1810468 | − | hypothetical protein |
| B624_1463 | 1810468 | 1811421 | − | ATP-binding protein of ABC transporter system |
| B624_1464 | 1811519 | 1812739 | − | glycosyl transferase domain protein |
| B624_1465 | 1812742 | 1814253 | − | hypothetical protein |
| B624_1466 | 1814329 | 1815252 | + | glycosyltransferase for cell wall membrane |
| B624_1467 | 1815481 | 1816629 | − | Lactaldehyde reductase |
| B624_1468 | 1817069 | 1818370 | + | cyclopropane-fatty-acyl-phospholipid synthase |
| B624_1469 | 1818482 | 1819687 | + | Permeases of the majorfacilitator superfamily |
| B624_1470 | 1820205 | 1821215 | − | UDP-glucose 4-epimerase |
| B624_1471 | 1821543 | 1822400 | + | methyltransferase |
| B624_1472 | 1822698 | 1823195 | − | hypothetical protein |
| B624_1473 | 1823244 | 1823708 | − | hypothetical protein |
| B624_1474 | 1823795 | 1824079 | + | hypothetical protein |
| B624_1475 | 1825086 | 1826453 | − | hypothetical protein |
| B624_1476 | 1827699 | 1828901 | − | Phage integrase family |
| B624_1477 | 1829429 | 1830229 | + | azlC protein |
| B624_1478 | 1830229 | 1830558 | + | branched-chain amino acid permease |
| B624_1479 | 1830743 | 1831258 | − | phosphotyrosine protein phosphatase |
| B624_1480 | 1831385 | 1832044 | − | dihydrofolate reductase |

TABLE 1-continued

Open reading frames of the genome of 35624.

| Gene ID | Start | End | Strand | Predicted Function |
|---|---|---|---|---|
| B624_1481 | 1832157 | 1833026 | − | thymidylate synthase |
| B624_1482 | 1833154 | 1833564 | + | hypothetical protein |
| B624_1483 | 1833629 | 1834663 | − | Universal stress protein UspA and related nucleotide-binding proteins |
| B624_1484 | 1834835 | 1835572 | − | P60 extracellular protein, invasion associatedprotein lap |
| B624_1485 | 1835733 | 1836476 | − | NLP/P60 family domain protein |
| B624_1486 | 1836692 | 1837645 | − | Surface antigen |
| B624_1487 | 1838039 | 1839178 | + | phosphoserine aminotransferase |
| B624_1488 | 1839305 | 1839562 | + | hypothetical protein |
| B624_1489 | 1839693 | 1840883 | − | sensor histidine kinase |
| B624_1490 | 1841074 | 1841745 | + | phosphate transport system regulatory proteinPhoU |
| B624_1491 | 1842110 | 1842847 | − | phosphoglycerate mutase |
| B624_1492 | 1842910 | 1843872 | − | 1,4-dihydroxy-2-naphthoateoctaprenyltransferase |
| B624_1493 | 1843937 | 1845616 | − | lysyl-tRNA synthetase |
| B624_1494 | 1846117 | 1847304 | + | AraJ-like protein probably involvedin transport of arabinose polymers |
| B624_1495 | 1847394 | 1849754 | + | TPR Domain domain protein |
| B624_1496 | 1849833 | 1850462 | + | hypothetical protein |
| B624_1497 | 1850618 | 1852216 | − | hypothetical protein |
| B624_1498 | 1852325 | 1853062 | − | hypothetical protein |
| B624_1499 | 1853062 | 1854780 | − | Hypothetical protein |
| B624_1500 | 1854894 | 1856174 | + | histidine protein kinase |
| B624_1501 | 1856174 | 1856866 | + | transcription regulator, LuxR family |
| B624_1502 | 1856920 | 1857939 | − | UDP-glucose 4-epimerase |
| B624_1503 | 1858012 | 1859556 | − | galactose-1-phosphate uridylyltransferase |
| B624_1504 | 1859606 | 1860682 | − | aminoglycoside phosphotransferase |
| B624_1505 | 1860713 | 1862965 | − | lacto-n-biose phosphorylase |
| B624_1506 | 1863426 | 1864382 | − | sugar ABC transporter, permease protein |
| B624_1507 | 1864382 | 1865350 | − | MalF-type ABC sugar transport systems permease component |
| B624_1508 | 1865546 | 1866859 | − | solute binding protein of ABC transporter forsugars |
| B624_1509 | 1867217 | 1867369 | − | hypothetical protein |
| B624_1510 | 1867867 | 1869150 | − | seryl-tRNA synthetase |
| B624_1511 | 1869384 | 1870562 | + | Diacylglycerol kinase catalytic domain (presumed) protein |
| B624_1512 | 1870573 | 1871409 | − | transcription antiterminator, BglG family |
| B624_1513 | 1871430 | 1873829 | − | PTS system component |
| B624_1514 | 1874293 | 1875843 | + | major facilitator family transporter |
| B624_1515 | 1875934 | 1877607 | + | phosphoglucomutase, alpha-D-glucosephosphate-specific |
| B624_1516 | 1878343 | 1879437 | − | hypothetical protein |
| B624_1517 | 1879668 | 1880087 | + | BadM/Rrf2 family transcriptional regulator |
| B624_1518 | 1880224 | 1881837 | + | Pyridine nucleotide-disulphide oxidoreductase family protein |
| B624_1519 | 1882380 | 1883360 | + | RNase H |
| B624_1520 | 1883494 | 1884189 | + | ribose 5-phosphate isomerase |
| B624_1521 | 1884629 | 1885258 | − | hypothetical protein |
| B624_1522 | 1885386 | 1886921 | + | DNA repair protein RadA |
| B624_1523 | 1886942 | 1888063 | − | riboflavin biosynthesis protein RibF |
| B624_1524 | 1888164 | 1889324 | − | tRNA pseudouridine synthase B |
| B624_1525 | 1889329 | 1889799 | − | ribosome-binding factor A |
| B624_1526 | 1889953 | 1892877 | − | translation initiation factor IF-2 |
| B624_1527 | 1893150 | 1894214 | − | transcription elongation factor |
| B624_1528 | 1894356 | 1895147 | + | lipoprotein |
| B624_1529 | 1895194 | 1896234 | − | LacI-type transcriptional regulator |
| B624_1530 | 1896770 | 1897951 | − | Alpha-L-arabinofuranosidase |
| B624_1531 | 1897936 | 1898334 | − | Alpha-L-arabinofuranosidase |
| B624_1532 | 1899147 | 1899944 | − | Transglutaminase-like superfamily domain protein |
| B624_1533 | 1900154 | 1902331 | − | Domain of unknown function (DUF404) family |
| B624_1534 | 1902601 | 1903515 | + | tRNA pseudouridine synthase I |
| B624_1535 | 1903603 | 1904142 | − | ribosomal protein L17 |
| B624_1536 | 1904245 | 1905237 | − | RNA polymerases L/13 to 16 kDa subunit |
| B624_1537 | 1905321 | 1905716 | − | ribosomal protein S11 |
| B624_1538 | 1905807 | 1906181 | − | ribosomal protein S13p/S18e |
| B624_1539 | 1906333 | 1906443 | − | ribosomal protein L36 |
| B624_1540 | 1906470 | 1906685 | − | translation initiation factor IF-1 |
| B624_1541 | 1906865 | 1907422 | − | adenylate kinase |
| B624_1542 | 1907595 | 1908929 | − | preprotein translocase, SecY subunit |
| B624_1543 | 1909207 | 1909656 | − | ribosomal protein L15 |
| B624_1544 | 1909662 | 1909844 | − | ribosomal protein L30 |
| B624_1545 | 1909853 | 1910551 | − | ribosomal protein S5 |
| B624_1546 | 1910581 | 1910949 | − | ribosomal protein L18 |
| B624_1547 | 1910954 | 1911490 | − | ribosomal protein L6 |
| B624_1548 | 1911511 | 1911906 | − | ribosomal protein S8 |
| B624_1549 | 1911999 | 1912181 | − | ribosomal protein S14p/S29e |
| B624_1550 | 1912186 | 1912755 | − | ribosomal protein L5 |
| B624_1551 | 1912755 | 1913087 | − | ribosomal protein L24 |
| B624_1552 | 1913092 | 1913457 | − | ribosomal protein L14 |

TABLE 1-continued

Open reading frames of the genome of 35624.

| Gene ID | Start | End | Strand | Predicted Function |
|---|---|---|---|---|
| B624_1553 | 1913555 | 1913812 | − | ribosomal protein S17 |
| B624_1554 | 1913818 | 1914066 | − | ribosomal protein L29 |
| B624_1555 | 1914069 | 1914485 | − | ribosomal protein L16 |
| B624_1556 | 1914495 | 1915295 | − | ribosomal protein S3 |
| B624_1557 | 1915301 | 1915657 | − | ribosomal protein L22 |
| B624_1558 | 1915677 | 1915952 | − | ribosomal protein S19 |
| B624_1559 | 1915971 | 1916798 | − | ribosomal protein L2 |
| B624_1560 | 1916838 | 1917131 | − | ribosomal protein L23 |
| B624_1561 | 1917140 | 1917793 | − | ribosomal protein L4/L1 family |
| B624_1562 | 1917803 | 1918441 | − | ribosomal protein L3 |
| B624_1563 | 1918461 | 1918766 | − | ribosomal protein S10 |
| B624_1564 | 1918999 | 1920027 | + | hypothetical protein |
| B624_1565 | 1920366 | 1923092 | − | PutA2 |
| B624_1566 | 1923607 | 1924797 | + | probable repressor in the Rok (NagC/XylR)family |
| B624_1567 | 1924797 | 1927334 | + | glycogen operon protein GlgX |
| B624_1568 | 1927431 | 1927919 | − | ribosomal protein S9 |
| B624_1569 | 1927945 | 1928391 | − | ribosomal protein L13 |
| B624_1570 | 1928792 | 1930954 | − | 4-alpha-glucanotransferase |
| B624_1571 | 1931125 | 1931865 | − | Leucine rich repeat variant |
| B624_1572 | 1931876 | 1932514 | − | hypothetical protein |
| B624_1573 | 1932579 | 1933592 | − | possible 2-hydroxyacid dehydrogenase |
| B624_1574 | 1933669 | 1935009 | − | capA protein |
| B624_1575 | 1935547 | 1936491 | − | Permease protein |
| B624_1576 | 1936720 | 1937991 | + | DNA-damage-inducible protein P |
| B624_1577 | 1938024 | 1939256 | − | aminotransferase |
| B624_1578 | 1939374 | 1939691 | − | fdxC |
| B624_1579 | 1939755 | 1941278 | − | possible cationic amino acid transporter |
| B624_1580 | 1941433 | 1942653 | − | UDP-N-acetylenolpyruvoylglucosamine reductase |
| B624_1581 | 1942930 | 1943094 | − | ribosomal protein L33 |
| B624_1582 | 1943529 | 1944245 | + | cystathionine gamma lyase |
| B624_1583 | 1944924 | 1945214 | − | chaperonin, 10 kDa |
| B624_1584 | 1945390 | 1946811 | − | hypothetical protein |
| B624_1585 | 1946895 | 1947557 | − | possible acetytransferase |
| B624_1586 | 1947644 | 1948360 | + | 5-formyltetrahydrofolate cyclo-ligase-relatedprotein |
| B624_1587 | 1948527 | 1948709 | + | hypothetical protein |
| B624_1588 | 1948950 | 1949516 | + | cation transport ATPase |
| B624_1589 | 1949617 | 1949814 | − | hypothetical protein |
| B624_1590 | 1949820 | 1953440 | − | hypothetical protein |
| B624_1591 | 1953452 | 1954999 | − | hypothetical protein |
| B624_1592 | 1955200 | 1955577 | − | ribosomal protein L7/L12 |
| B624_1593 | 1955689 | 1956207 | − | ribosomal protein L10 |
| B624_1594 | 1956479 | 1957306 | − | hypothetical protein |
| B624_1595 | 1957561 | 1958952 | + | Permease protein |
| B624_1596 | 1959385 | 1962123 | − | polyribonucleotide nucleotidyltransferase |
| B624_1597 | 1962444 | 1962710 | − | ribosomal protein S15 |
| B624_1598 | 1962882 | 1963562 | − | hypothetical protein |
| B624_1599 | 1964088 | 1966964 | − | possible extracellular exo-xylanase |
| B624_1600 | 1967190 | 1969712 | − | endo-1,4-beta-xylanase D |
| B624_1601 | 1970329 | 1971432 | + | IS30 family, transposase [imported] |
| B624_1602 | 1971591 | 1972274 | − | Membrane protein involved in the export of O-antigen and teichoic acid |
| B624_1603 | 1972411 | 1973088 | − | hypothetical protein |
| B624_1604 | 1973553 | 1974794 | − | Large exoproteins involved in heme utilization or adhesion |
| B624_1605 | 1974994 | 1977441 | − | von Willebrand factor type A domain protein |
| B624_1606 | 1978150 | 1978326 | − | hypothetical protein |
| B624_1607 | 1978353 | 1978898 | − | phosphopantethiene protein transferase |
| B624_1608 | 1979459 | 1988974 | − | Fatty acid synthase |
| B624_1609 | 1989016 | 1990635 | − | propionyl-CoA carboxylase, beta chain |
| B624_1610 | 1990631 | 1992592 | − | Acetyl-/propionyl-CoA carboxylase alpha chain |
| B624_1611 | 1993105 | 1993701 | + | B624_oY protein |
| B624_1612 | 1993739 | 1994710 | − | B624_otin--acetyl-CoA-carboxylase ligase |
| B624_1613 | 1994874 | 1996895 | + | hypothetical protein |
| B624_1614 | 1996904 | 1997731 | + | hypothetical protein |
| B624_1615 | 1997829 | 1998578 | − | transcriptional regulator |
| B624_1616 | 1998629 | 1999459 | − | transcriptional regulator, IclRfamily |
| B624_1617 | 2011797 | 2012486 | − | ribosomal protein L1 |
| B624_1618 | 2012505 | 2012933 | − | ribosomal protein L11 |
| B624_1619 | 2013199 | 2014089 | − | transcription termination/antitermination factorNusG |
| B624_1620 | 2014122 | 2014346 | − | preprotein translocase SecE subunit |
| B624_1621 | 2014593 | 2015795 | − | aspartate aminotransferase [imported] |
| B624_1622 | 2015889 | 2017019 | − | spo0B-associated GTP-binding protein |
| B624_1623 | 2017023 | 2018711 | − | GTP-binding protein |
| B624_1624 | 2018783 | 2019028 | − | ribosomal protein L27 |
| B624_1625 | 2019054 | 2019359 | − | ribosomal protein L21 |
| B624_1626 | 2019502 | 2022534 | − | ribonuclease, Rne/Rng family |

TABLE 1-continued

Open reading frames of the genome of 35624.

| Gene ID | Start | End | Strand | Predicted Function |
|---|---|---|---|---|
| B624_1627 | 2022850 | 2024052 | − | succinyl-diaminopimelate desuccinylase |
| B624_1628 | 2024159 | 2025100 | + | auxin efflux carrier |
| B624_1629 | 2025282 | 2026727 | − | permease protein |
| B624_1630 | 2026727 | 2027818 | − | ABC transporter, ATP-binding protein |
| B624_1631 | 2027996 | 2029441 | − | Maf-like protein |
| B624_1632 | 2029581 | 2030690 | − | homoserine kinase |
| B624_1633 | 2030800 | 2032113 | − | homoserine dehydrogenase |
| B624_1634 | 2032276 | 2033865 | − | diaminopimelate decarboxylase |
| B624_1635 | 2033871 | 2035730 | − | arginyl-tRNA synthetase |
| B624_1636 | 2035944 | 2036606 | + | AcrR-type transcriptional regulator |
| B624_1637 | 2036606 | 2037880 | + | permease |
| B624_1638 | 2037970 | 2038899 | + | LysR-type transcriptional regulator |
| B624_1639 | 2038996 | 2040246 | + | probable aminotransferase |
| B624_1640 | 2040298 | 2041620 | − | UDP-N-acetylglucosamine1-carboxyvinyltransferase |
| B624_1641 | 2041869 | 2043212 | + | NADH oxidase |
| B624_1642 | 2043424 | 2044548 | − | dihydroorotate dehydrogenase family protein |
| B624_1643 | 2044591 | 2046273 | − | CAAX amino terminal protease family proteinfamily |
| B624_1644 | 2046594 | 2047283 | − | 3-isopropylmalate dehydratase small subunit |
| B624_1645 | 2047369 | 2048769 | − | 3-isopropylmalate dehydratase, large subunit |
| B624_1646 | 2049063 | 2049860 | + | transcriptional regulator, IclR family |
| B624_1647 | 2050021 | 2051391 | − | Phosphohydrolases |
| B624_1648 | 2051896 | 2054130 | + | polyphosphate kinase |
| B624_1649 | 2054291 | 2055487 | + | Phosphohistidine phosphatase SixA |
| B624_1650 | 2055627 | 2056298 | + | hypothetical protein |
| B624_1651 | 2056564 | 2057871 | − | hypothetical protein |
| B624_1652 | 2058175 | 2058813 | + | uracil phosphoribosyltransferase |
| B624_1653 | 2058864 | 2059340 | + | hypothetical protein |
| B624_1654 | 2059542 | 2060648 | − | Glycerophosphoryl diester phosphodiesterase |
| B624_1655 | 2060677 | 2061747 | − | Glutamyl-tRNA synthetase 1 |
| B624_1656 | 2061933 | 2064599 | − | ATP-dependent Clp protease, ATP-binding subunitClpB |
| B624_1657 | 2064821 | 2066377 | − | histidine ammonia-lyase |
| B624_1658 | 2066617 | 2067489 | + | transcriptional regulator, IclR family |
| B624_1659 | 2067489 | 2067662 | + | hypothetical protein |
| B624_1660 | 2067741 | 2068559 | − | Fumarylacetoacetate hydrolase family protein |
| B624_1661 | 2068665 | 2069906 | − | hypothetical protein |
| B624_1662 | 2070097 | 2071272 | − | UDP-galactopyranose mutase |
| B624_1663 | 2071555 | 2072670 | + | dTDP-glucose 4,6-dehydratase |
| B624_1664 | 2072827 | 2074311 | + | hypothetical protein |
| B624_1665 | 2074307 | 2075068 | + | hypothetical protein |
| B624_1667 | 2075763 | 2076530 | − | IS1533, OrfB |
| B624_1668 | 2076530 | 2077987 | − | Transposase and inactivated derivatives |
| B624_1669 | 2078280 | 2079218 | − | glycosyltransferase |
| B624_1670 | 2079313 | 2079666 | − | sialic acid-specific9-O-acetylesterase |
| B624_1671 | 2080049 | 2081173 | + | Acyltransferase family |
| B624_1672 | 2081181 | 2082893 | − | hypothetical protein |
| B624_1673 | 2082902 | 2085928 | − | Glycosyltransferase family A |
| B624_1674 | 2085935 | 2087170 | − | glycosyl transferase, group 2family protein |
| B624_1675 | 2087259 | 2088509 | − | polysaccharide ABC transporter, ATP-binding protein |
| B624_1676 | 2088515 | 2089351 | − | polysaccharide ABC transporter, permease protein |
| B624_1677 | 2089580 | 2091367 | + | Glycosyl transferase family 8 |
| B624_1678 | 2091457 | 2092698 | − | UDP-glucose 6-dehydrogenase |
| B624_1679 | 2092974 | 2093636 | + | dTDP-glucose 4,6-dehydratase |
| B624_1680 | 2093654 | 2094844 | − | o-acetyltransferase |
| B624_1681 | 2094847 | 2097099 | − | hypothetical protein |
| B624_1682 | 2097441 | 2098844 | + | antimicrobial peptide ABC superfamily ATP binding cassette transporter, permease protein |
| B624_1683 | 2098844 | 2099962 | + | salx-type abc antimicrobial peptide transport system atpase component |
| B624_1684 | 2100089 | 2100790 | + | HD superfamily hydrolase |
| B624_1685 | 2100871 | 2101728 | + | hypothetical protein |
| B624_1686 | 2101825 | 2104335 | − | kup3 |
| B624_1687 | 2104481 | 2105437 | − | hydrolase, TatD family |
| B624_1688 | 2105717 | 2106784 | + | Fic protein family family |
| B624_1689 | 2106816 | 2108621 | − | ABC transporter, ATP-binding/permease protein |
| B624_1690 | 2108635 | 2110542 | − | ABC transporter, ATP-binding/permease protein |
| B624_1691 | 2111297 | 2112703 | − | alpha-galactosidase |
| B624_1692 | 2113077 | 2114231 | + | transcriptional regulator, LacI family |
| B624_1693 | 2114409 | 2115356 | − | probable AraC/XylS-type transcriptionalregulator |
| B624_1694 | 2115401 | 2117626 | − | Hypothetical protein |
| B624_1695 | 2117851 | 2119374 | + | aminopeptidase C |
| B624_1696 | 2119555 | 2120628 | + | hypothetical protein |
| B624_1697 | 2120701 | 2121335 | + | hypothetical protein |
| B624_1698 | 2121673 | 2123535 | − | methionyl-tRNA synthetase |
| B624_1699 | 2123873 | 2124496 | + | hypothetical protein |
| B624_1700 | 2124496 | 2124864 | + | hypothetical protein |
| B624_1701 | 2124897 | 2125904 | − | hypothetical protein |

TABLE 1-continued

Open reading frames of the genome of 35624.

| Gene ID | Start | End | Strand | Predicted Function |
|---|---|---|---|---|
| B624_1702 | 2126487 | 2127902 | − | possible symporter |
| B624_1703 | 2127984 | 2129027 | + | thiamine biosynthesis lipoprotein ApbE |
| B624_1704 | 2129186 | 2131012 | − | ABC transporter, ATP-binding/permease protein |
| B624_1705 | 2131231 | 2133099 | − | ABC transporter, ATP-binding/permease protein |
| B624_1706 | 2133289 | 2133807 | − | transcriptional regulator, MarR family |
| B624_1708 | 2135008 | 2138841 | − | Glycosyl hydrolases family |
| B624_1709 | 2139209 | 2143594 | − | hypothetical protein |
| B624_1710 | 2143901 | 2145394 | − | ATP-dependent DNA helicase recG |
| B624_1711 | 2145737 | 2147257 | − | amino acid permease |
| B624_1712 | 2147448 | 2151185 | − | permease protein |
| B624_1713 | 2151199 | 2151897 | − | ABC transporter, ATP-binding protein |
| B624_1714 | 2152041 | 2152607 | + | probable TetR-like transcriptional regulator |
| B624_1715 | 2152832 | 2154310 | + | aromatic amino acid transport protein AroP |
| B624_1716 | 2154575 | 2155774 | + | transposase IS116/IS110/IS902 family protein |
| B624_1717 | 2155961 | 2160952 | − | Glycosyl hydrolases family 43 |
| B624_1718 | 2161359 | 2164649 | − | Glycosyl hydrolases family 43 |
| B624_1719 | 2164997 | 2168191 | − | possible arabinosidase |
| B624_1720 | 2168529 | 2169131 | − | hypothetical protein |
| B624_1721 | 2169340 | 2170179 | − | sugar ABC transporter, permease protein |
| B624_1722 | 2170182 | 2171033 | − | sugar ABC transporter, permease protein |
| B624_1723 | 2171416 | 2172429 | + | transcription regulator, LacI family |
| B624_1724 | 2172690 | 2174015 | − | possible solute binding protein of ABCtransporter |
| B624_1725 | 2174424 | 2175134 | − | phosphoglycerate mutase |
| B624_1726 | 2175226 | 2175600 | + | hypothetical protein |
| B624_1727 | 2175786 | 2176550 | + | nitroreductase family protein |
| B624_1728 | 2176846 | 2179572 | + | hypothetical protein |
| B624_1729 | 2179572 | 2181908 | + | hypothetical protein |
| B624_1730 | 2182027 | 2182278 | − | hypothetical protein |
| B624_1731 | 2188511 | 2189263 | + | regulatory protein, SIR2 family |
| B624_1732 | 2189415 | 2190677 | − | threonine dehydratase |
| B624_1733 | 2190928 | 2192745 | − | alpha-glucosidase |
| B624_1734 | 2192872 | 2194731 | − | alpha-galactosidase |
| B624_1735 | 2194766 | 2196433 | − | Glucosidase |
| B624_1736 | 2196537 | 2197364 | − | ABC transporter permease protein |
| B624_1737 | 2197364 | 2198320 | − | MalF-type ABC sugar transport systems permease component |
| B624_1738 | 2198408 | 2199730 | − | MalE-type ABC sugar transport system periplasmic component |
| B624_1739 | 2199980 | 2201095 | − | hypothetical protein |
| B624_1740 | 2201159 | 2202484 | − | sugar ABC superfamily ATP binding cassette transporter, substrate binding protein |
| B624_1741 | 2202692 | 2203717 | + | LacI-type transcription regulator |
| B624_1742 | 2203838 | 2204854 | + | LacI-type transcriptional regulator |
| B624_1743 | 2204919 | 2205782 | − | sugar ABC transporter, permease protein |
| B624_1744 | 2205804 | 2206730 | − | sugar ABC transporter, permease protein |
| B624_1745 | 2206755 | 2208041 | − | sugar ABC transporter, sugar-binding protein |
| B624_1746 | 2208215 | 2209420 | + | NagC/XylR-type transcriptional regulator |
| B624_1747 | 2209591 | 2211894 | − | alpha-galactosidase |
| B624_1748 | 2212017 | 2212463 | − | cytidine and deoxycytidylate deaminase |
| B624_1749 | 2212589 | 2214658 | + | Na/H antiporter |
| B624_1750 | 2214858 | 2215613 | − | Esterase protein |
| B624_1751 | 2215735 | 2216592 | − | hypothetical protein |
| B624_1752 | 2216949 | 2217527 | + | deoxycytidine triphosphate deaminase |
| B624_1753 | 2217593 | 2219320 | + | hypothetical protein |
| B624_1754 | 2219543 | 2222527 | − | calcium-transporting ATPase |
| B624_1755 | 2222713 | 2223582 | − | protein probably involved in xylan degradation, possible xylan esterase |
| B624_1756 | 2223622 | 2224932 | − | hypermease of the major facilitator superfamily protein |
| B624_1757 | 2225005 | 2225994 | + | RNA methyltransferase, TrmH family, group 3 |
| B624_1758 | 2226107 | 2227501 | − | lipopolysaccharide kinase |
| B624_1759 | 2227740 | 2228864 | − | ATP binding protein of ABC transporter for sugars |
| B624_1760 | 2229226 | 2230419 | − | glycosyl transferase domain protein |
| B624_1761 | 2230486 | 2231475 | − | Ribonucleotide reductase, beta subunit |
| B624_1762 | 2231704 | 2233896 | − | ribonucleoside-diphosphate reductase, alphasubunit |
| B624_1763 | 2234015 | 2234470 | − | nrdI protein |
| B624_1764 | 2234470 | 2234733 | − | Glutaredoxin |
| B624_1765 | 2235324 | 2235971 | − | Transcriptional regulators |
| B624_1766 | 2235958 | 2236635 | − | Ribosomal protein L1 |
| B624_1767 | 2236828 | 2237592 | + | ion transporter |
| B624_1768 | 2237788 | 2238891 | + | hypothetical protein |
| B624_1769 | 2239035 | 2239400 | − | Beta-glucosidase-related glycosidases |
| B624_1770 | 2239837 | 2241951 | + | Serine/threonine protein kinase |
| B624_1771 | 2242132 | 2243106 | + | hypothetical protein |
| B624_1772 | 2243633 | 2245111 | + | G5 domain protein |
| B624_1773 | 2245147 | 2246067 | + | dimethyladenosine transferase |
| B624_1774 | 2246067 | 2247014 | + | kinase, GHMP family, group 2 |

TABLE 1-continued

Open reading frames of the genome of 35624.

| Gene ID | Start | End | Strand | Predicted Function |
|---|---|---|---|---|
| B624_1775 | 2247064 | 2247690 | + | hypothetical protein |
| B624_1776 | 2247781 | 2249193 | – | pcnA |
| B624_1777 | 2249280 | 2250569 | + | NUDIX domain protein |
| B624_1778 | 2250569 | 2252836 | + | hypothetical protein |
| B624_1779 | 2252836 | 2254560 | + | Hypothetical protein |
| B624_1780 | 2254646 | 2256706 | + | hypothetical protein |
| B624_1781 | 2256829 | 2257845 | + | thioredoxin reductase |
| B624_1782 | 2258158 | 2259516 | – | chromosome partitioning protein ParB |
| B624_1783 | 2259519 | 2260487 | – | Soj family protein |
| B624_1784 | 2260741 | 2261403 | – | methyltransferase GidB |
| B624_1785 | 2261558 | 2262088 | – | R3H domain protein |
| B624_1786 | 2262215 | 2263219 | – | inner membrane insertion protein |
| B624_1787 | 2263219 | 2263533 | – | hypothetical protein |
| B624_1788 | 2263533 | 2263889 | – | ribonuclease P protein component |
| B624_1789 | 2263925 | 2264056 | – | ribosomal protein L34 |

The Open reading frames (ORF) listed in Table 1 are defined by their position in the genomic sequence of SEQ ID No. 1. For example B624_0001 is defined by the nucleotide sequence of base numbers 1 and 1500 (inclusive) of SEQ ID No. 1.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Example 1—Isolation of Bifidobacterium longum 35624

Appendices and sections of the large and small intestine of the human G.I.T., obtained during reconstructive surgery, were screened for probiotic bacterial strains. All samples were stored immediately after surgery at −80° C. in sterile containers. Frozen tissues were thawed, weighed and placed in cysteinated (0.05%) one quarter strength Ringers' solution. Each sample was gently shaken to remove loosely adhering microorganisms. Following transfer to a second volume of Ringers' solution, the sample was vortexed for 7 min to remove tightly adhering bacteria. In order to isolate tissue embedded bacteria, samples were also homogenised in a Braun blender. The solutions were serially diluted and spread-plated (100 µl) on to the following agar media: RCM (reinforced clostridial media) and RCM adjusted to pH 5.5 using acetic acid; TPY (trypticase, peptone and yeast extract), Chevalier, P. et al. (1990). MRS (deMann, Rogosa and Sharpe); ROG (acetate medium (SL) of Rogosa); LLA (Liver-lactose agar of Lapiere); BHI (brain heart infusion agar); LBS (Lactobacillus selective agar) and TSAYE (tryptone soya agar supplemented with 0.6% yeast extract). All agar media was supplied by Oxoid Chemicals with the exception of TPY agar. Plates were incubated in anaerobic jars (BBL, Oxoid) using $CO_2$ generating kits (Anaerocult A, Merck) for 2-5 days at 37° C.

Gram positive, catalase negative rod-shaped or bifurcated/pleomorphic bacteria isolates were streaked for purity on to complex non-selective media (TPY). Isolates were routinely cultivated in TPY medium unless otherwise stated at 37° C. under anaerobic conditions. Presumptive Bifidobacteria species were stocked in 40% glycerol and stored at −20° and −80° C.

Approximately fifteen hundred catalase negative bacterial isolates from different samples were chosen and characterised in terms of their Gram reaction, cell size and morphology, growth at 15° C. and 45° C. and fermentation end-products from glucose. Greater than sixty percent of the isolates tested were Gram positive, homofermentative cocci arranged either in tetrads, chains or bunches. Eighteen percent of the isolates were Gram negative rods and heterofermentative coccobacilli.

The remaining isolates (twenty-two percent) were predominantly homofermentative coccobacilli. Thirty eight strains were characterised in more detail. All thirty eight isolates tested negative both for nitrate reduction and production of indole from tryptophan.

Bifidobacterium longum 35624 was chosen for full genome sequencing from this group of strains due to its proven anti-inflammatory activity in murine models of colitis (McCarthy et. al., 2004) and its immunomodulatory effects following oral consumption by Irritable Bowel Syndrome (IBS) patients (O'Mahony et al., 2005).

Example 2—Sequencing the Genome of Bifidobacterium longum 35624

Chromosomal DNA from bifidobacteria was isolated as previously described (O'Riordan and Fitzgerald, 1998). The genome sequence of 35624 was sequenced using a Roche 454 FLX Titanium instrument by the commercial sequencing service providers Agencourt Bioscience (Beverly, Mass.) and Eurofins MWG Operon (Germany) and then assembled, after which remaining gaps were closed using Sanger Sequencing of PCR products. Sequence reads were initially assembled using Phred (Ewing and Green, 1998; Ewing et al., 1998), Phrap (P. Green, University of Washington), RepeatMasker (AFA. Smit, R. Hubley, & P. Green) and the Staden software package (Staden et al., 2000). Final assembly of 35624 was verified using Newbler v 2.3. The accession number for the 35624 genome sequence is CP013673.

Example 3—Analysing the Genome of Bifidobacterium longum 35624

Prediction of putative open reading frames (ORFs) was performed using PRODIGAL prediction software and supported by BLASTX [58] alignments. Results of Prodigal/BLASTX were combined manually and a preliminary identification of ORFs was performed on the basis of BLASTP analysis against a non-redundant protein database provided by the National Centre for Biotechnology. Using the ORF finding outputs and associated BLASTP results, Artemis (Rutherford et al., 2000) was employed for visualisation and manual editing in order to verify, and if necessary, redefine the start of every predicted coding region, or to remove or add coding regions. The assignment of protein function to predicted coding regions was performed manually. In addition, the individual members of the revised gene/protein data set were searched against the protein family (Pfam) (Punta et al., 2012) and COG (Tatusov et al., 2000)COG databases. Ribosomal RNA (rRNA) and transfer RNA (tRNA) genes were detected using RNAMMER and tRNA-scanSE, respectively.

Example 4—Identifying Unique Genes in the Genome of Bifidobacterium longum 35624

We identified a region from base numbers 448412 to 474640 (inclusive) of SEQ ID No. 1 that we designated exopolysaccharide (EPS) region 1 (SEQ ID No. 2). The EPS region 1 encodes a cluster of genes B624_0342 to B624_0366 (Table 2).

Reversible protein phosphorylation is a major mechanism in the regulation of fundamental signalling events in all living organisms. Tyrosine phosphorylation is today recognized as a key regulatory device of bacterial physiology, linked to exopolysaccharide production, virulence, stress response and DNA metabolism (Grangeasse et al., 2012). Tyrosine phosphatase together with tyrosine kinase are responsible for controlling polysaccharide biosynthesis and export, but the underlying mechanism remains unclear (Grangeasse et al., 2012).

TABLE 2

ID and functions of $eps_{624}$ cluster genes.

| Gene ID | Start | Stop | Strand | Predicted Function |
|---|---|---|---|---|
| B624_0342 | 448412 | 450007 | + | priming glycosyltransferase |
| B624_0343 | 450098 | 452029 | + | hypothetical protein |
| B624_0344 | 452091 | 453566 | + | tyrosine kinase |
| B624_0345 | 453574 | 454725 | + | glycosyltransferase |
| B624_0346 | 454725 | 456065 | + | glycosyltransferase |
| B624_0347 | 456065 | 457126 | + | UDP-glucuronate 5' epimerase |
| B624_0348 | 457201 | 458448 | + | UDP-glucose 6-dehydrogenase |
| B624_0349 | 458489 | 459550 | + | glycosyltransferase |
| B624_0350 | 459581 | 460408 | + | NAD dependent epimerase/dehydratase |
| B624_0351 | 460446 | 460952 | + | acyltransferase |
| B624_0352 | 460985 | 461998 | + | glycosyltransferase |
| B624_0353 | 462020 | 463360 | + | polymerase |
| B624_0354 | 463363 | 464292 | + | glycosyl transferase |
| B624_0355 | 464311 | 465753 | + | flippase |
| B624_0356 | 465774 | 466280 | + | acyltransferase |
| B624_0357 | 466366 | 467514 | − | NAD dependent epimerase/dehydratase |
| B624_0358 | 467785 | 468615 | − | integrase |
| B624_0359 | 468615 | 468770 | − | transposase |
| B624_0360 | 469189 | 470208 | + | rhamnose biosynthesis |
| B624_0361 | 470218 | 471303 | + | rhamnose biosynthesis |
| B624_0362 | 471349 | 472245 | + | rhamnose biosynthesis |
| B624_0363 | 472438 | 472654 | + | Pseudogene; transposase |
| B624_0364 | 472715 | 472858 | + | hypothetical protein |
| B624_0365 | 473371 | 473802 | − | hypothetical protein |
| B624_0366 | 474083 | 474640 | − | protein-tyrosine-phosphatase |

Example 5—Isolation and Screening of EPS-Producing Bifidobacterial Strain from Fecal Samples Fecal Sample Preparation Fecal samples were collected by the subjects using a Kendall precision commode specimen collection system. The collected samples were stored chilled in a cold pack prior to sample processing. Only samples that are less than twenty four hours old were used in the evaluations.

A 10.0 g sample of mixed fecal material was placed into a plastic stomaching bag containing 90 ml of saline. The suspension was stomached for 2 minutes. The suspension was filtered through a gauze pad contained within a disposable funnel. Following the filtration, 45 ml of the filtered fecal homogenate was transferred to a 50 ml disposable centrifuge tube. This fecal suspension was further used for DNA extraction or for bacterial isolation.

Screening Fecal Samples Using Three TaqMan Real-Time PCR Assays.

Fecal Sample DNA Preparation. A 2.0 ml aliquot of the fecal homogenate was pelleted using a microcentrifuge. The pellets were resuspended in 20 mg/ml lysozyme, for 2 hours at 37° C. DNA was extracted using a QIAamp DNA Stool Mini Kit (Qiagen). The DNA concentration was measured by Pico Green assay (Molecular Probes). Once the DNA concentration was measured, the DNA was stored at 4° C.

TaqMan Real-Time PCR Reactions. The test samples were diluted to a concentration of DNA of 2 ng/ul so that 5 µl contained a total of 10 ng DNA. Samples were assayed by a total of three separate assays.

The following reaction mix was made:

| | | |
|---|---|---|
| Water | 15.75 µl | |
| 10 µM forward primer | 1.5 µl | (300 nM final concentration) |
| 10 µM reverse primer | 1.5 µl | (300 nM final concentration) |
| 10 µM TaqMan probe | 1 µl | (200 nM final concentration) |
| BSA (20 mg/ml) | 0.25 µl | (0.1 ug/ml final concentration) |
| TaqMan Universal Master Mix | 25 µl | |

A bulk mix was made for the number of samples to be assayed. A 45 µl aliquot was dispensed into each well of a 96 well microtitre plate, then 5 µl DNA was added to each well. The plate was spun briefly, and placed into the thermocycler (ABI 7900 HT). The standard TaqMan thermocycling protocol was used.

TanMan RT-PCR Program. The standard TaqMan quantitative PCR thermocycling protocol is as follows:

Step 1: 95° C. for 10 minutes (to activate the AmpliTaq Gold polymerase)

Step 2: 95° C. for 15 seconds (the denaturation step)

Step 3: 60° C. for 60 seconds (the priming/polymerization step)

Steps 2 and 3 are repeated 40 times. Fluorescent data is collected at step 3.

Primers and Probes for Three TaqMan RT-PCR assays. The fecal sample DNAs were screened using a EPS gene-specific assay and two B. longum 35624 gene-specific assays (UNK1 and UNK2). The specific genes used and their TaqMan primer sets are shown in Table 3 below.

TABLE 3

35624 Primer set for TaqMan PCR

| Target Gene | Name | Sequence 5'-3' | Genome start | Genome end | TaqMan Probe label |
|---|---|---|---|---|---|
| BI01615 (UNK-1) | UNK1-F1 | CCATGAGCGGTTTCACGAA (SEQ ID No. 4) | 1451446 | 1451428 | 5' 6-FAM 3' |
|  | UNK1-R1 | TTGGACGGTGCCTGTGATTA (SEQ ID No. 5) | 1451393 | 1451412 | NFQ-MG |
|  | UNK1-MGB1 | CGGGCAATCAAC (SEQ ID No. 6) | 1451426 | 1451415 |  |
| BI02420t (UNK-2) | UNK2-F1 | ACTTGACGTACCGTTTTGAGATTTC (SEQ ID No. 7) | 1656479 | 1656503 | 5' 6-FAM 3' |
|  | UNK2-R1 | CTAAGCATGGCAAGGCTGATAGT (SEQ ID No. 8) | 1656562 | 1656540 | NFQ-MGB |
|  | UNK2-MGB1 | TGCGACCAACACGC (SEQ ID No. 9) | 1656525 | 1656538 |  |
| BI00783 (EPS) | EPS-F1 | GGGTCCAATAAGAAGGTTCCATATT (SEQ ID No. 10) | 456491 | 456515 | 5'6-FAM 3' |
|  | EPS-R1 | GCATGTGCCAACAGCTCATC (SEQ ID No. 11) | 456591 | 456572 | TAMR |
|  | EPS-TAMRA | CGGATGACAAGGTAGATAATCCAGTGAGCCTATAC (SEQ ID No. 12) | 456519 | 456553 |  |

The fecal samples which showed high DNA concentration by the B. longum 35624 EPS gene-specific assay, but negative reactions by using B. longum 35624 gene-specific assays, were further used for the isolation of potential EPS-producing bacteria.

Example 6—Isolation and Characterization of Strain B. longum AH0097 and Strain B. longum AH1172 from Fecal Samples One milliliter of bacterial suspension (see Example 5 above) was transferred to 9.0 ml of sterile phosphate-buffered saline which constituted the $10^{-1}$ dilution. One milliliter of this $10^{-1}$ dilution was transferred to 9.0 ml of sterile phosphate-buffered saline which was the $10^{-2}$ dilution. This process was continued until the $10^{-10}$ dilution was prepared. Then, 0.1 ml of each dilution was plated onto the surfaces of Reinforced Clostridial Agar (RCA) plates (BD or equivalent) and Lactobacillus Man-Rogosa Sharpe agar (MRSA) plates (BD or equivalent). The plates were incubated under anaerobic condition (COY anaerobic Chamber) at 33° C.±2° C. for 48-72 hours.

Following incubation, single colonies (a total of approximately 100 colonies) were picked from RCA and MRSA plates and further streaked on new plates for isolate purification. The plates with the streaked colonies were incubated under anaerobic conditions (COY anaerobic Chamber) at 33° C.±2° C. for 48 to 72 hours. After incubation, the pure colonies observed on plates were then submitted for DNA extraction.

Screening Fecal Isolates Using Three TaqMan Real-Time PCR Assays

The bacterial DNA was extracted using the Preman™ Ultra Sample Preparation Reagent and Protocol (Applied Biosystems). The DNA was further analyzed using three TaqMan RT-PCR assays (EPS gene-specific assay [EPS-1] and two B. longum 35624 gene-specific assays [UNK1 and UNK2] as described above in Example 5. Two isolates showed positive results for the B. longum 35624 EPS gene-specific assay, and negative results for the B. longum 35624 gene-specific assays. Both isolates were therefore further identified using 16S rDNA sequencing Identification of potential EPS-producing strain by 16S rDNA sequencing. The 16S rRNA gene fragment was amplified and sequenced using ABI Full Gene PCR kit (Applied Biosystems, Foster City, Calif.).

(1). 16S rRNA Gene Amplification:

PCR amplification was carried out on a GeneAmp PCR System 9700 thermal cycler with the following program:
Initial Hold: 95° C. for 10 minutes
30 Cycles: 95° C. for 30 seconds (Denaturing)
60° C. for 30 seconds (Annealing)
72° C. for 45 seconds (Extension)
Final Extension: 72° C. for 10 minutes (2). 16S rRNA Gene Sequencing:

Sequencing was further performed on the thermal cycler using the following program:
Cycles: 96° C. for 10 seconds (Denaturing)
50° C. for 5 seconds (Annealing)
60° C. for 4 minutes (Extension)
Final step Hold at 4° C.

The sequencing PCR product was further purified using DyeEX™ 2.0 spin kit and sequenced using 3130 xl Genetic Analyzer (Applied Biosystems, Foster City, Calif.).

(3) Sequence Data Analysis:

Comparison of the consensus sequences with GenBank sequences was done by using Basic Local Alignment Search Tool (BLAST). The GenBank search indicated that the B. longum 35624 EPS gene-specific positive, but B. longum 35624 gene-specific negative isolates were both Bifidobacterium longum. These strains were designated names by Alimentary Health, AH0097 and AH1172.

Example 7—Isolation and Screening of EPS-Expressing Bifidobacterial longum strains Isolation of Bacterial Strains Bacteria were isolated from bowel tissue and/or fecal samples using the methodology described in Example 1 above. In particular, Bifidobacterium longum AH0097 and Bifidobacterium longum strain AH1172 were isolated from faecal samples from healthy adult human subjects.

EPS Gene Cluster Screen

Bacterial strains were screened for the presence of genes from EPS cluster 1 (Table 2 above) using the primers listed in Tables 4 below. Briefly, the following methodology was used for the PCR EPS cluster gene screen:

10 μl Modified Rogosa broth media (+0.05% cysteine) was inoculated aseptically with a freshly grown colony of the bacterial strain and incubatd anaerobically at 37° C. until turbid (about 16 to about 24 hours). The broth cultures were centrifuged and DNA was isolated from the resultant pellet using a Sigma™ extraction procedure. A nanodrop was used to ascertain the concentration of DNA in the sample and samples were diluted using DEPC water to a final concentration of 50 ng/μl DNA per sample. The template DNA samples were used in individual PCR reactions with the primer sets listed in Tables 4 below under the following conditions:

| Step | Temp (° C.) | Time (sec) | |
|---|---|---|---|
| 1 | 95 | 240 | |
| 2 | 95 | 45 | |
| 3 | 60 | 45 | |
| 4 | 72 | 45 | repeat steps 2 to 4, 25 times |
| 5 | 4 | hold | |

The primers were specifically designed to amplify a PCR product of approximately 500 base pair for the 25 genes of EPS clusters 1. PCR products were visualised following agarose gel electrophoresis with an appropriate DNA ladder for reference sizing. The presence (YES) or absence (NO) of a 500 bp PCR product is indicated in Table 5 below.

TABLE 4

Primers for screening bacterial strains for the presence of genes from EPS cluster 1

| Gene ID | Primer name | L R F R | Sequence | SEQ ID NO. |
|---|---|---|---|---|
| B624_0342 | 1.01 | L | tat gtt gcc ggc aft tat ca | SEQ ID No. 12 |
| B624_0342 | 1.01 | R | tgc gcg ttc atg tca ata at | SEQ ID No. 13 |
| B624_0343 | 1.02 | L | ggc gta gca agt tca agg ag | SEQ ID No. 14 |
| B624_0343 | 1.02 | R | aat aac cgc tgc agg aac ac | SEQ ID No. 15 |
| B624_0344 | 1.03 | L | gtg cag gac ggt aat gga gt | SEQ ID No. 16 |
| B624_0344 | 1.03 | R | gct tcg ggt ctg gat cat ta | SEQ ID No. 17 |
| B624_0345 | 1.04 | L | tgc tga caa gtg gag tct gg | SEQ ID No. 18 |
| B624_0345 | 1.04 | R | cca cgt cta cga gca act ca | SEQ ID No. 19 |
| B624_0346 | 1.05 | L | gaa agc gaa gag tgg tct gg | SEQ ID No. 20 |
| B624_0346 | 1.05 | R | ccg gct gat ttg atg aga tt | SEQ ID No. 21 |
| B624_0347 | 1.06 | L | tgc cgc tgt act ggt cac | SEQ ID No. 22 |
| B624_0347 | 1.06 | R | gca tgt gcc aac agc tca | SEQ ID No. 23 |
| B624_0348 | 1.07 | L | cca aca cgt atc tgg cac tg | SEQ ID No. 24 |
| B624_0348 | 1.07 | R | tcg gag cca aag aag gta ga | SEQ ID No. 25 |
| B624_0349 | 1.08 | L | ata ccg cgt atg ctt tgg ac | SEQ ID No. 26 |
| B624_0349 | 1.08 | R | aaa cgg taa cca ctc gct tg | SEQ ID No. 27 |
| B624_0350 | 1.09 | L | atg gga tcg atg cat gaa at | SEQ ID No. 28 |
| B624_0350 | 1.09 | R | ttc tcg gca ata aac cgt tc | SEQ ID No. 29 |
| B624_0351 | 1.10 | L | cca gcg gtt aft tcg ttg tt | SEQ ID No. 30 |
| B624_0351 | 1.10 | R | ggt ggc atg atc ctt atg ct | SEQ ID No. 31 |
| B624_0352 | 1.11 | L | gct atc ttc acc gca ttg gt | SEQ ID No. 32 |
| B624_0352 | 1.11 | R | cca gtc agg gaa ggt cac at | SEQ ID No. 33 |
| B624_0353 | 1.12 | L | tga aat aca cgc aac ccg ta | SEQ ID No. 34 |
| B624_0353 | 1.12 | R | aatgcgtcaaaaccgatacc | SEQ ID No. 35 |
| B624_0354 | 1.13 | L | gga aag caa tga gga agc tg | SEQ ID No. 36 |
| B624_0354 | 1.13 | R | gat ttg atg caa agc aag ca | SEQ ID No. 37 |

TABLE 4 -continued

Primers for screening bacterial strains for the presence of genes from EPS cluster 1

| Gene ID | Primer name | L R F R | Sequence | SEQ ID NO. |
|---|---|---|---|---|
| B624_0355 | 1.14 | L | gtg agt acc gtt tcc gca at | SEQ ID No. 38 |
| B624_0355 | 1.14 | R | ttc ctt ggt tcc cgt gat ag | SEQ ID No. 39 |
| B624_0356 | 1.15 | L | gct ggg att ttg gaa gtg aa | SEQ ID No. 40 |
| B624_0356 | 1.15 | R | tgt tac ccc cgg cat aat aa | SEQ ID No. 41 |
| B624_0357 | 1.16 | L | acc ggt aac gtt cag aft gc | SEQ ID No. 42 |
| B624_0357 | 1.16 | R | gca ata ccg cct tga cct ta | SEQ ID No. 43 |
| B624_0358 | 1.17 | L | ttg tac cac cac acg tac cg | SEQ ID No. 44 |
| B624_0358 | 1.17 | R | cgc gag ttc aat ggc tat g | SEQ ID No. 45 |
| B624_0359 | 1.18 | L | aca tcg acc tcc atc tcc ag | SEQ ID No. 46 |
| B624_0359 | 1.18 | R | ata cgt aac agc ggc tcc ac | SEQ ID No. 47 |
| B624_0360 | 1.19 | L | aag tac gat gtg cgc tac ca | SEQ ID No. 48 |
| B624_0360 | 1.19 | R | cat cac ggt cag gat gtc ac | SEQ ID No. 49 |
| B624_0361 | 1.20 | L | cga ata cac gga cat caa cg | SEQ ID No. 50 |
| B624_0361 | 1.20 | R | gag aat cga gca gct gga ac | SEQ ID No. 51 |
| B624_0362 | 1.21 | L | tgg gag agg agt tca tcg ac | SEQ ID No. 52 |
| B624_0362 | 1.21 | R | gta tcc agc cat gcg taa cc | SEQ ID No. 53 |
| B624_0363 | 1.22 | L | taatgggcgg acggaaagtt | SEQ ID No. 54 |
| B624_0363 | 1.22 | R | tgccctccgt gaaatacagg | SEQ ID No. 55 |
| B624_0364 | 1.23 | L | caacgatgtc catatcgcct | SEQ ID No. 56 |
| B624_0364 | 1.23 | R | gcgccctgtt gttgatgatg | SEQ ID No. 57 |
| B624_0365 | 1.24 | L | ccgattccgc cattcgtttc | SEQ ID No. 58 |
| B624_0365 | 1.24 | R | ggccacatcg aaaatcacgg | SEQ ID No. 59 |
| B624_0366 | 1.25 | L | gaattggctt gcagagcggc | SEQ ID No. 60 |
| B624_0366 | 1.25 | R | acagaatcag gtcggcttgc | SEQ ID No. 61 |

TABLE 5

Results of EPS cluster 1 gene screen
In which YES indicates the presence and NO indiates the absence of a 500 bp PCR product.

| Gene ID | Primer set | B. longum 35624 | B. longum AH1172 | B. longum AH0097 |
|---|---|---|---|---|
| B624_0342 | 1.01 | YES | YES | YES |
| B624_0343 | 1.02 | YES | YES | YES |
| B624_0344 | 1.03 | YES | YES | YES |
| B624_0345 | 1.04 | YES | YES | YES |
| B624_0346 | 1.05 | YES | YES | YES |
| B624_0347 | 1.06 | YES | YES | YES |
| B624_0348 | 1.07 | YES | YES | YES |
| B624_0349 | 1.08 | YES | YES | YES |
| B624_0350 | 1.09 | YES | YES | YES |
| B624_0351 | 1.10 | YES | YES | YES |
| B624_0352 | 1.11 | YES | NO | YES |
| B624_0353 | 1.12 | YES | YES | YES |
| B624_0354 | 1.13 | YES | YES | YES |
| B624_0355 | 1.14 | YES | YES | YES |
| B624_0356 | 1.15 | YES | YES | YES |
| B624_0357 | 1.16 | YES | YES | YES |
| B624_0358 | 1.17 | YES | YES | NO |
| B624_0359 | 1.18 | YES | YES | YES |
| B624_0360 | 1.19 | YES | YES | YES |
| B624_0361 | 1.20 | YES | YES | NO |
| B624_0362 | 1.21 | YES | YES | YES |

Predicted Role of eps$_{624}$ Genes to eps$_{624}$ Structure.

The eps$_{624}$ cluster encodes a number of key enzymes that are predicted to be required for EPS production, by means of the so-called Wzx/Wzy-dependent pathway, which typically employs a priming glycosyltransferase (pGT), one or more glycosyl transferases (GHs), a flippase, and a polymerase to produce an extracellular heteropolysaccharide (Schmid et al., 2015). The first gene (corresponding to locus tag BL_0342 and designated here as pgt624) of the $eps_{624}$ gene cluster is predicted to encode the pGT, which adds the first monosaccharide to a cytoplasmic, membrane-bound carrier molecule undecaprenyl as part of the oligosaccharidic subunit biosynthesis (Salazar et al., 2009). The $eps_{624}$ cluster encodes five additional GTs (corresponding to locus tags BL_0345, BL_0346, BL_0349 and BL_0352;), which are predicted to each add one monosaccharide to the carrier molecule so as to complete the oligosaccharidic subunit, prior to its export to the external side of the membrane by a flippase (predicted to be encoded by a gene corresponding to locus tag BL_0355) and its subsequent use by a polymerase (putatively specified by locus tag BL_0353) to produce the EPS polymer. Interestingly, two adjacent genes of the $eps_{624}$ cluster, corresponding to B624_0347 and 118 B624_0348, are predicted to encode a UDP-glucuronate 5'-epimerase and a UDP-glucose 6-dehydrogenase, suggesting that one of the incorporated monosaccharides of the EPS is an epimer of glucuronic acid, e.g. galacturonic acid or mannuronic acid. Three genes located within the $eps_{624}$ cluster, corresponding to locus tags B624_0360 through to B624_0362), encode enzymes known to be involved in the biosynthesis of dTDP-L-rhamnose (Marumo et al., 1992), while the deduced protein products of B624_0350 and B624_0357 are predicted to encode NAD-dependent reductase/epimerase enzymes. Such enzymes have been shown to be involved in the rerouting of the dTDP-L-rhamnose biosynthesis pathway towards the production of dTDP-D-fucose or dTDP-6-deoxy-L-talose (Gaugler and Gabriel, 1973; Nakano et al., 2000; Yoshida et al., 1999). The $eps_{624}$ cluster also encodes two predicted acetyl transferases, similar to enzymes that have previously been shown to perform O-acetylation reactions on particular sugar components (such as 6-deoxy-L-talose) in polysaccharides (Knirel et al., 2002). Furthermore, the genes with locus tags B624_0344 and B624_0366 represent putative tyrosine kinase and phosphotyrosine protein phosphatase activities, respectively, which have been associated with controlling EPS export and polymerisation (Grangeasse et al., 2012). Therefore, based on the gene content of the $eps_{624}$ cluster, we predict that the EPS produced by 35624 is composed of a repeating subunit that consists of six monosaccharides, of which one is an epimer of glucuronic acid, one or two others are either D-fucose or 6-deoxy-talose, and some of which may be O-acetylated.

The genes located within the $eps_{624}$ cluster, corresponding to locus tags B624_0342 through to B624_0366, are required for the production of the *B. longum* 35624 subsp. *longum* specific EPS. The production of an EPS by a bacterium minimally requires a priming glycosyltransferase (pGT), one or more glycosyl transferases (GHs), a flippase, and a polymerase to produce an extracellular heteropolysaccharide. The number of glycosyl transferases may vary thereby affecting the length of oligosaccharidic subunit. Additionally, the presence of acetyl transferases may result in the O-acetylation of some of the monosaccharides.

Protein-Tyrosine-Phosphatase

Reversible protein phosphorylation is a major mechanism in the regulation of fundamental signalling events in all living organisms. Tyrosine phosphorylation is today recognized as a key regulatory device of bacterial physiology, linked to exopolysaccharide production, virulence, stress response and DNA metabolism (Grangeasse et al., 2012). Tyrosine phosphatase together with tyrosine kinase are responsible for controlling polysaccharide biosynthesis and export, but the underlying mechanism remains unclear (Grangeasse et al., 2012). In the *B. longum* subsp. *longum* 35624 genome B624_0344 encodes tyrosine kinase while B624_0366 encodes tyrosine phosphatase. B624_0366 was not previously identified as being part of the $eps_{624}$ cluster in patent application PCT/IE2009/000079 published as WO2010/055499A.

Congo Red Agar Screen

A Congo red agar screen was used to phenotypically screen for EPS expressing bacterial strains. Briefly, 10 ml Modified Rogosa broth media (+0.05% cysteine) was inoculated aseptically with a freshly grown colony of the bacterial strain and incubated anaerobically at 37° C. until turbid (about 16 to about 24 hours). The broth cultures were aseptically streaked onto Congo Red Agar plates and incubated anaerobically at 37° C. for 48 hours. It is believed that EPS produced as a by-product of the growth and/or metabolism of certain strains prevents the uptake of the Congo red stain resulting in a cream/white colony morphology. Stains that produce less EPS take up the Congo red stain easily, resulting in a pink/red colony morphology. Strains that do not produce an EPS stain red and look almost transparent in the red agar background.

Figure 2:
FIG. 2 is a photograph of *B. longum* NCIMB 41714 (AH1172) grown on a Congo Red Agar plate.
Figure 3:
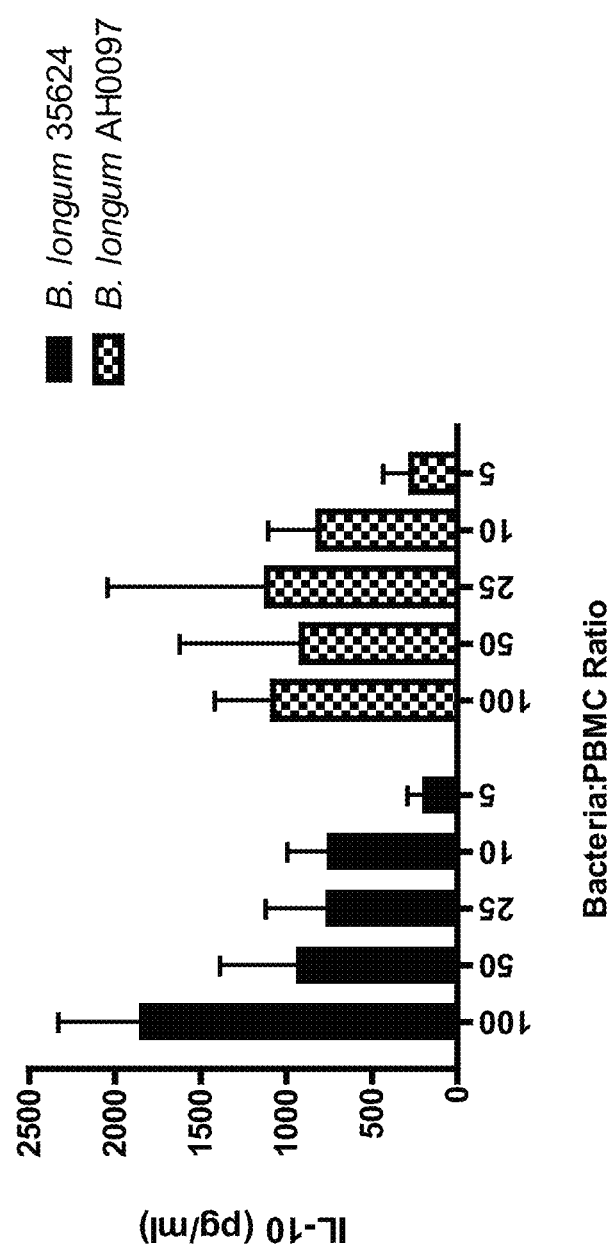
FIG. 3. is a graph of IL-10 secretion by PBMC stimulated with *B. longum* AH0097 or *B. longum* 35624 for 48 h (n=5)
Figure 4:
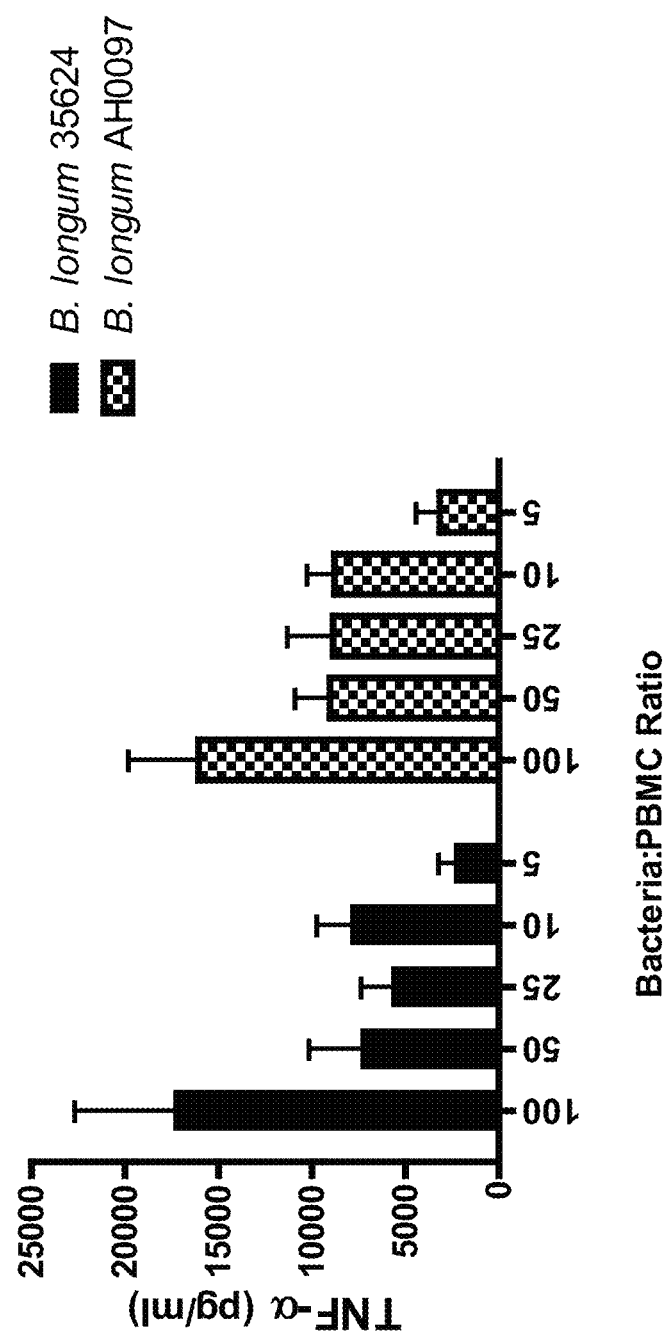
FIG. 4: is a graph of TNF-α secretion by PBMC stimulated with *B. longum* AH0097 or *B. longum* 35624 for 48 h (n=5)
Figure 5:
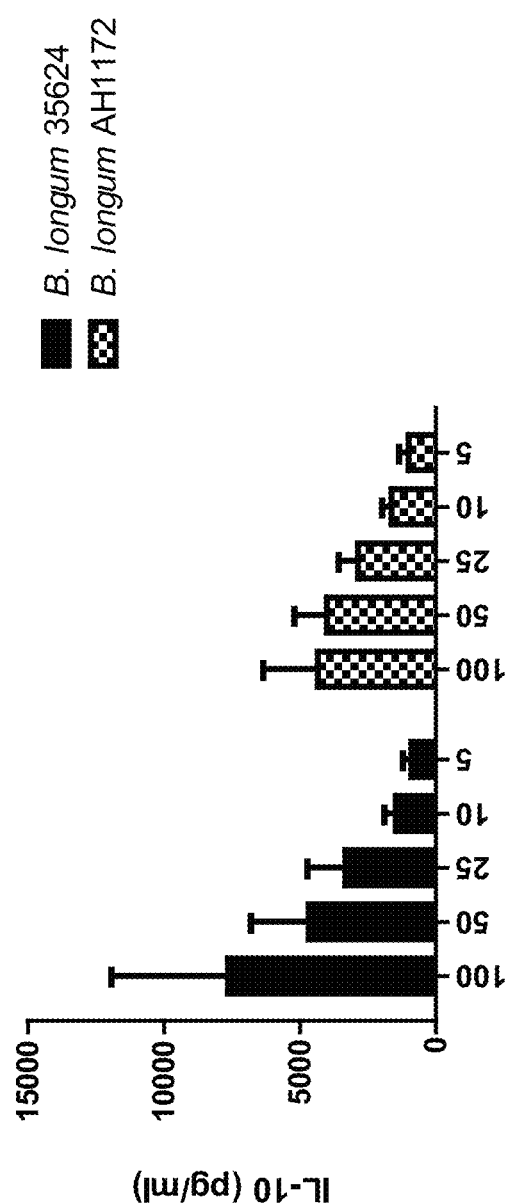
FIG. 5: is a graph of IL-10 secretion by PBMC stimulated with *B. longum* AH1172 or *B. longum* 35624 for 48 h (n=3)
Figure 6:
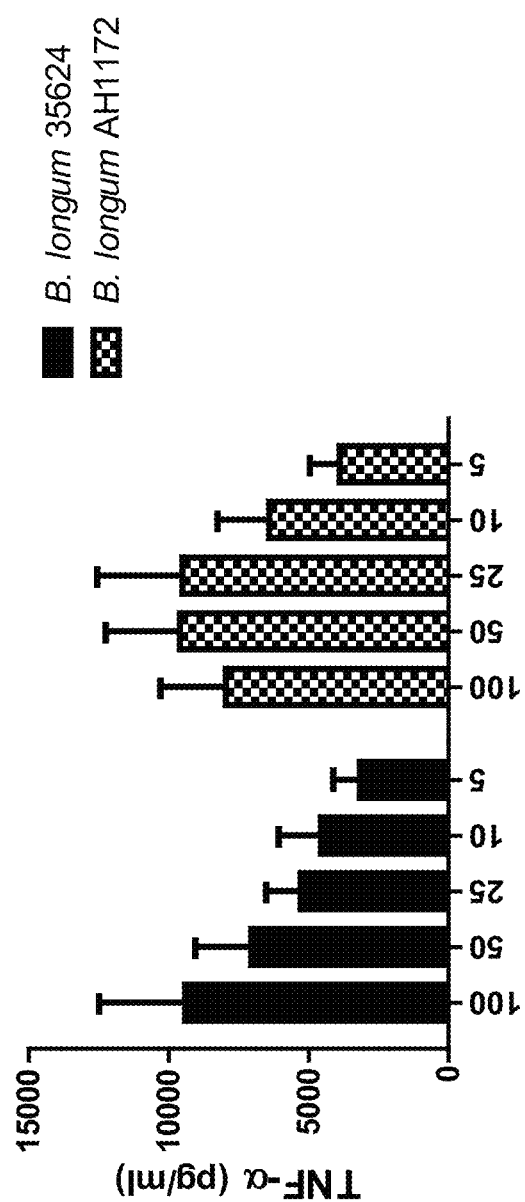
FIG. 6: TNF-α secretion by PBMC stimulated with *B. longum* AH1172 or *B. longum* 35624 for 48 h (n=4)

Referring to FIGS. 1 and 2, the following colony morphologies were observed:

TABLE 6

Colony morphologies from Congo red agar screen

| Bacterial Strain | Colony morphology |
| --- | --- |
| *B. longum* 35624 | Convex, mucoid, bright white colonies |
| *B. longum* AH0097 (FIG. 1) | Convex, mucoid, bright white colonies |
| *B. logum* AH0172 (FIG. 2) | Convex, mucoid, bright white colonies |

The control of inflammatory diseases is exerted at a number of levels. The controlling factors include hormones, prostaglandins, reactive oxygen and nitrogen intermediates, leukotrienes and cytokines. Cytokines are low molecular weight biologically active proteins that are involved in the generation and control of immunological and inflammatory responses. A number of cell types produce these cytokines, with neutrophils, monocytes and lymphocytes being the major sources during inflammatory reactions due to their large numbers at the injured site.

Multiple mechanisms exist by which cytokines generated at inflammatory sites influence the inflammatory response. Chemotaxis stimulates homing of inflammatory cells to the injured site, whilst certain cytokines promote infiltration of cells into tissue. Cytokines released within the injured tissue result in activation of the inflammatory infiltrate. Most cytokines are pleiotropic and express multiple biologically overlapping activities. As uncontrolled inflammatory responses can result in diseases such as IBD, it is reasonable to expect that cytokine production has gone astray in individuals affected with these diseases.

*B. longum* 35624, *B. longum* AH0097 and *B. longum* AH1172 Induce Nearly Identical Cytokine Profiles in PBMCs.

Peripheral blood mononuclear cells (PBMCs) were isolated from fresh human peripheral blood using BD Vacutainer CPT tubes (BD catalog 362761), as per the manufacturer's instructions. PBMCs were washed and resuspended in Dulbecco's MEM (Gibco catalog 10569-010) plus 25 mM HEPES, 10% fetal bovine serum (Sigma catalog F4135), and 1% penicillin/streptomycin (Sigma catalog P0781). $2 \times 10^5$ PBMCs (in 200 µl of DMEM) were plated into each well of a 96-well culture plate.

Bacteria were grown in Difco MRS media and harvested just after entering into stationary phase. All cells were grown under anaerobic conditions at 37° C. Growth curves (OD vs # of live cells) were constructed for each growth condition, and washed cells were normalized by cell number before addition to the PBMCs.

Bacteria (20 µl in phosphate buffered saline (PBS)) were added to each well of PBMCs to give the total number of bacteria as indicated for each experiment. Five different amounts of bacteria were tested: 2E07, 1E07, 5E6, 2E6 and 1E6 were added to separate wells of PBMCs. A no-bacteria control also was run. All assays were done in triplicate. After a 2-day incubation at 37° C., the plates were spun at 300×g, and the supernatants were removed and stored frozen at −80° C. until analysis.

Cytokines in the culture supernatants were assayed using a 96-well assay kit from Meso Scale Discovery (Gaithersburg, Md.; catalog K15008B-1). Human Interleukin 10 (Il-10), and Tumor Necrosis Factor alpha (TNFa) were quantitated and reported as picograms per milliliter. Each sample was assayed in duplicate.

FIGS. 3 to 6 show the results of a representative experiment. For each cytokine shown, *B. longum* 35624, *B. longum* AH0097 and *B. longum* AH1172 induce nearly identical levels of cytokines. These levels are very different than the levels induced by other Bifidobacterial strains that they were compared to.

The control of inflammatory diseases is exerted at a number of levels. The controlling factors include hormones, prostaglandins, reactive oxygen and nitrogen intermediates, leukotrienes and cytokines. Cytokines are low molecular weight biologically active proteins that are involved in the generation and control of immunological and inflammatory responses, while also regulating development, tissue repair and haematopoiesis. A number of cell types produce these cytokines, with neutrophils, monocytes and lymphocytes being the major sources during inflammatory reactions due to their large numbers at the injured site. They provide a means of communication between leukocytes themselves and also with other cell types. Most cytokines are pleiotrophic and express multiple biologically overlapping activities. Cytokine cascades and networks control the inflammatory response rather than the action of a particular cytokine on a particular cell type (Arai K I, et al., 1990). Waning of the inflammatory response results in lower concentrations of the appropriate activating signals and other inflammatory mediators leading to the cessation of the inflammatory response. As uncontrolled inflammatory responses can result in diseases such as IBD, it is reasonable to expect that cytokine production has gone astray in individuals affected with these diseases.

Interleukin-10 (IL-10) is an anti-inflammatory cytokine which is produced by many cell types including monocytes, macrophages, dendritic cells, mast cells and lymphocytes (in particular T regulatory cells). IL-10 down-regulates the expression of pro-inflammatory Th1 cytokines, MHC class II antigens, and co-stimulatory molecules on antigen presenting cells. It also enhances B cell survival, proliferation, and antibody production. This cytokine can block NF-κB activity, and is involved in the regulation of the JAK-STAT signaling pathway. Murine knock-out studies have demonstrated the essential role for IL-10 in immunoregulation as IL-10KO mice develop severe colitis. In addition, bacteria which are potent inducers of IL-10 have been shown to promote T regulatory cell differentiation in vivo thus contributing to immunological homeostasis (O'Mahony et al., AJP 2006; O'Mahony et al., PLoS Pathogens 2008).

Tumor necrosis factor alpha (TNFα) is a pivotal proinflammatory cytokine as it initiates a cascade of cytokines and biological effects resulting in the inflammatory state. Therefore, agents which inhibit TNFα are currently being used for the treatment of inflammatory diseases, e.g. infliximab.

Compositions and Methods for Formulating EPS Producing Strains

Compositions

The following table demonstrates compositions incorporating the freeze dried bacteria expressing the EPS.

| | Weight (%) | | | | |
|---|---|---|---|---|---|
| Material | A | B | C | D | E |
| Freeze-dried bacteria | 5.3 | 6.0 | 5.0 | 10 | 5.0 |
| Microcrystalline cellulose | 93.7 | | 72.0 | | |
| Maltodextrin | | 93.5 | | | |
| Fumed silica | | | 2.0 | | |
| Ascorbic acid | | | 10.0 | | |
| Tricalcium citrate | | | 10.0 | | |
| Potato starch | | | | 89.0 | |
| Psyllium husk | | | | | 94.0 |
| Magnesium stearate | 1.0 | 0.5 | 1.0 | 1.0 | 1.0 |
| Total | 100 | 100 | 100 | 100 | 100 |

To ensure adequate shelf life of the composition the following dry handling procedures can used. The mixing and filling operations can be performed in a humidity-controlled environment where the RH can be maintained below 50%, alternatively below 40%. The freeze-dried bacteria can be pre-concentrated to the desired CFU/g to achieve the desired total amount in each dosage unit based on the fraction of freeze-dried bacteria and total amount of mixed powder to be dosed. The freeze-dried bacterial can be added to the mixing cavity of, for example, a Pharmatech mixer along with the appropriate amount of stabilizing excipient such as microcrystalline cellulose, potato starch or the like. The stabilizing excipients can be pre-dried to have low water contents, for example, less than 10%, alternatively less than 6% water content. The head space within the mixing cavity can be flushed with a dry gas, such as nitrogen, so that the relative humidity is maintained at a low level. The powders can then be mixed for 20 minutes at a mixing speed of 60 rpm to ensure good mixing. Once mixing is completed, the powder can be handled and stored in a low Rh environment, for example, below 50% RH, or below 40% RH.

The appropriate amount of the resulting dry-blended powder to achieve the desired CFU per dosage unit can then be filled into appropriately sized capsules, for example, a gelatin or hydroxypropyl methyl cellulose (HPMC) capsule under a dry environment. Alternatively, an appropriate amount of the resulting powder can be filled into a sachet and sealed under a dry environment. The resulting capsules or sachets can be stored at room temperature (20-30° C.) or alternatively at reduced temperature (4° C.) to extend shelf life.

| Powder | Freeze-dried Bacteria (CFU) | Unit | Powder Quantity (g) | CFU/Unit |
|---|---|---|---|---|
| A | $1 \times 10^{10}$ | Gelatin capsule | 0.2 | $1.1 \times 10^8$ |
| B | $1 \times 10^{11}$ | HPMC capsule | 0.25 | $1.5 \times 10^9$ |
| C | $1 \times 10^{12}$ | Gelatin capsule | 0.18 | $9.0 \times 10^9$ |
| D | $1 \times 10^9$ | Sachet | 1.0 | $1.0 \times 10^8$ |
| E | $1 \times 10^{11}$ | Sachet | 2.0 | $1.0 \times 10^{10}$ |

Alternatively, the freeze-dried bacteria can be incorporated into a dairy product such as yogurt or into a chewable dosage form using standard techniques.

| Material | Weight (%) | |
|---|---|---|
| | Yogurt | Chewable Dose Form |
| Freeze-dried bacteria | 8 | 3 |
| Milk | 70 | |
| Sugar | 20 | |
| Starch | 2 | |
| Microcrystalline cellulose | | 15 |
| Compressible sugar | | 40 |
| Fructose | | 40 |
| Citric acid | | 0.5 |
| Magnesium stearate | | 1 |
| Flavor | | 0.5 |
| Total | 100 | 100 |

Methods of Use

The compositions described herein are intended to be used as prophylactic, therapeutic or non-therapeutic treatments to alleviate diseases and conditions that affect animals, preferably mammals and humans. The compositions may be administered to subjects as a pharmaceutical, OTC or supplement, for example DSHEA, product. Non-limiting examples of prophylactic, therapeutic or non-therapeutic treatments can be for inflammatory diseases or conditions, or modulation of the immune system. The diseases and conditions can include inflammatory bowel disease, irritable bowel syndrome, diarrhea due to a range of causes such as travel or antibiotic treatment, allergy, asthma, fever control, nutritional disorders, maintaining or improving the condition of the gastrointestinal tract or skin, and respiratory disorders or infections. In particular, these compositions can be used to treat or prevent adverse conditions of the gastrointestinal tract.

Typically, the compositions are given to a subject as part of a dose regimen. The dose regimen can be varied depending on the specific state that is being treated or prevented and the unit dose format. For example, the total amount of bacteria administered per dose can range from $1 \times 10^6$ to $1 \times 10^{12}$ CFU per dose, preferably from $ax10^8$-$1 \times 10^{10}$ CFU per dose. The unit dose, when provided as a capsule can be swallowed directly with or without fluid. The powder contained in a sachet can be ingested directly or mixed with a liquid like milk or juice or mixed with a food such as yogurt. If already incorporated into a food supplement such as yogurt or into a chewable form the dose can be taken by eating. The dose regimen can proscribe administration at least once per month, at least once per week, at least once per day or more than once per day.

The dimensions and values disclosed herein are not to be understood as being strictly limited to the exact numerical values recited. Instead, unless otherwise specified, each such dimension is intended to mean both the recited value and a functionally equivalent range surrounding that value. For example, a value disclosed as "40" is intended to mean "about 40".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCES

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-3402.

Altschul S. F., Gish W., Miller W., Myers E. W. and Lipman D. J. (1990) Basic local alignment search tool. J Mol Biol. 215: 403-410.

Bateman, A., Birney, E., Cerruti, L., Durbin, R., Etwiller, L., Eddy, S. R., Griffiths-Jones, S., Howe, K. L., Marshall, M., and Sonnhammer, E. L. (2002). The Pfam protein families database. Nucleic Acids Res 30, 276-280.

Bendtsen J. D., Nielsen H., von Heijne G. and Brunak S. (2004) Improved prediction of signal peptides: SignalP 3.0. J Mol Biol. 340: 783-795.

Bouhnik Y Survival And Effects Of Bacteria Ingested In Fermented Milk In Man Lait 73 (2): 241-247 1993

Busch W, Saier M H The Transporter Classification (TC) system, 2002 Critical Reviews In Biochemistry And Molecular Biology 37 (5): 287-337 2002

Chevalier, P. et al. (1990) *J. Appl. Bacteriol* 68, 619-624)

Coutinho & Henrissat, 1999

Delcher A L, Harmon D, Kasif S, White O, Salzberg S L Improved microbial gene identification with GLIMMER Nucleic Acids Research 27 (23): 4636-4641 Dec. 1, 1999

Eddy, S. R. The HMMER software tools.

Eddy S R A memory-efficient dynamic programming algorithm for optimal alignment of a sequence to an RNA secondary structure BMC BIOINFORMATICS 3: Art. No. 18 2002

Green, P. The Phred/Phrap/Consed system home page.

Griffiths-Jones S, Moxon S, Marshall M, Khanna A, Eddy S R, Bateman A Rfam: annotating non-coding RNAs in complete genomes Nucleic Acids Research 33: D121-D124 Sp. Iss. SI Jan. 1, 2005

Krogh A, Larsson B, von Heijne G, Sonnhammer E L L., Predicting transmembrane protein topology with a hidden Markov model: Application to complete genomes Journal Of Molecular Biology 305 (3): 567-580 Jan. 19, 2001

Kurtz S, Schleiermacher C REPuter: fast computation of maximal repeats in complete genomes Bioinformatics 15 (5): 426-427 May 1999

Lowe T M, Eddy S R tRNAscan-S E: A program for improved detection of transfer RNA genes in genomic sequence Nucleic Acids Research 25 (5): 955-964 Mar. 1, 1997

Liu M, van Enckevort F H, Siezen R J, Genome update: lactic acid bacteria genome sequencing is booming Microbiology 2005, vol 151 pp 3811-3814

McCarthy et al., 2004

O'Mahony L, McCarthy J, Kelly P, Hurley G, Luo F, Chen K, O'Sullivan G C, Kiely B, Collins J K, Shanahan F, Quigley E M.: *Lactobacillus* and *bifidobacterium* in irritable bowel syndrome: symptom responses and relationship to cytokine profiles. Gastroenterology. 2005 March; 128(3):541-51.

O'Mahony et al., AJP 2006

O'Mahony et al., PLoS Pathogens 2008

Riley, 1993

Riley, 1998a

Rutherford, K., Parkhill, J., Crook, J., Horsnell, T., Rice, P., Rajandream, M. A., and Barrell, B. (2000). Artemis: sequence visualization and annotation. Bioinformatics 16, 944-945.

Salzberg S, Delcher A L, Fasman K H, Henderson J. A decision tree system for finding genes in DNA Journal Of Computational Biology 5 (4): 667-680 WIN 1998

Suzek, B. E., Ermolaeva, M. D., Schreiber, M., and Salzberg, S. L. (2001). A probabilistic method for identifying start codons in bacterial genomes. Bioinformatics 17, 1123-1130.

Tatusov, R. L., The XUGNITOR software.

Volfovsky et al., 2001

Wheeler et al., 2005

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10519430B2). An electronic copy of the "Sequence Listing" will also be available from the USPTO upon request and payment of the fee set forth in 37 CFR 1.19(b)(3).

The invention claimed is:

1. A formulation comprising an ingestable carrier comprising a stabilizing excipient having a water content of less than about 10% and an isolated strain of *Bifidobacterium longum* AH1172 having NCIMB accession number 41714.

2. The formulation of claim 1 wherein the ingestable carrier is a pharmaceutically acceptable carrier.

3. The formulation of claim 1 wherein the carrier does not occur in nature.

4. The formulation of claim 1 wherein the formulation is in a form selected from the group consisting of a capsule, a tablet, a pellet, a powder, or combinations thereof.

5. The formulation of claim 1 wherein the strain is present in the formulation at more than $10^6$ cfu per gram of the ingestable carrier.

* * * * *